US012599572B2

(12) United States Patent
Kaur et al.

(10) Patent No.: US 12,599,572 B2
(45) Date of Patent: Apr. 14, 2026

(54) SOLID LIPID NANOPARTICLES OF CURCUMIN

(71) Applicant: REGISTRAR, PANJAB UNIVERSITY CHANDIGARH, Chandigarh (IN)

(72) Inventors: Indu Pal Kaur, Chandigarh (IN); Vandita Kakkar, Chandigarh (IN); Simarjot Kaur Sandhu, Chandigarh (IN); Tanvi Gupta, Chandigarh (IN)

(73) Assignee: Punjab University Chandigarh, Chandigarh (IN)

( * ) Notice: Subject to any disclaimer, the term of this patent is extended or adjusted under 35 U.S.C. 154(b) by 1186 days.

(21) Appl. No.: 17/439,617

(22) PCT Filed: Nov. 26, 2019

(86) PCT No.: PCT/IB2019/060162
§ 371 (c)(1),
(2) Date: Sep. 15, 2021

(87) PCT Pub. No.: WO2020/109989
PCT Pub. Date: Jun. 4, 2020

(65) Prior Publication Data

US 2022/0151945 A1 May 19, 2022

(30) Foreign Application Priority Data

Nov. 26, 2018 (IN) ............................ 201811044487

(51) Int. Cl.
*A61K 9/51* (2006.01)
*A61K 31/12* (2006.01)
(Continued)

(52) U.S. Cl.
CPC .......... *A61K 9/5123* (2013.01); *A61K 9/5192* (2013.01); *A61K 31/12* (2013.01); *A61K 36/9066* (2013.01); *B82Y 5/00* (2013.01)

(58) Field of Classification Search
CPC .... A61K 9/5123; A61K 9/5192; A61K 31/12; A61K 36/9066; A61K 9/51; B82Y 5/00
See application file for complete search history.

(56) References Cited

U.S. PATENT DOCUMENTS

2011/0229532 A1* 9/2011 Nair ........................ A61P 29/00
977/773

FOREIGN PATENT DOCUMENTS

WO 2007103435 A2 9/2007
WO 2011116963 A2 9/2011
WO 2014135967 A1 9/2014

OTHER PUBLICATIONS

Lipoid, "Soybean Phospholipids and Formulations", retrieved 2024 from https://lipoid.com/en/products/raw-material-sources/soybean-phospholipids-formulations/ (Year: 2024).*
(Continued)

*Primary Examiner* — Marianne C Seidel
*Assistant Examiner* — Joshua A Atkinson
(74) *Attorney, Agent, or Firm* — Patent Law Works LLP

(57) ABSTRACT

Provided herein is a process for preparing solid lipid nanoparticles of curcumin. Also provided herein are solid lipid nanoparticles of curcumin having a particle size in the range of 20-800 nm. The solid lipid nanoparticles of curcumin show a very high entrapment efficiency of curcumin in the range of 50-100% in terms of actual curcumin content of the formulation. The solid lipid nanoparticles of curcumin show increased efficacy of the curcumin.

20 Claims, 22 Drawing Sheets

(51) Int. Cl.
*A61K 36/9066* (2006.01)
*B82Y 5/00* (2011.01)

(56) References Cited

OTHER PUBLICATIONS

Das et al. "Encapsulation of Curcumin into Poly -¿- Caprolactone Nanoparticles and its Physicochemical Characterization ", Int J Bio Sci Eng, 2011, vol. 2, No. 1, pp. 1-8 (Year: 2011).*
Liu et al., "Solid lipid nanoparticles for transdermal delivery of diclofenac sodium: preparation, characterization and in vitro studies", J Microencapsulation, 2010, 27(8), pp. 726-734 (Year: 2010).*
Pubchem, "Precirol", retrieved 2024 from https://pubchem.ncbi.nlm.nih.gov/compound/Precirol#section=InChl (Year: 2024).*
PCT International Search Report and Written Opinion; Application No. PCT/IB2019/0060162 Registrar, Panjab University Chandigarh, International filing date of Nov. 26, 2019, date of mailing Feb. 25, 2020, 9 pages.
"Shelat, Pragna, et al. Formulation of Curcuminoid Loaded Solid Lipid Nanoparticles in Order to Improve Oral Bioavailability," International Journal of Pharmacy and Pharmaceutical Sciences, Innovare Academic Sciences, vol. 7, No. 6, Apr. 28, 2015, pp. 278-282.

* cited by examiner (a)

(b)

(a)

(b)

(c)

(a)

(b)

(c)

SOLID LIPID NANOPARTICLES OF CURCUMIN

CROSS-REFERENCE TO RELATED APPLICATIONS

This application is a national phase entry under 35 U.S.C. § 371 of International Patent Application PCT/IB2019/060162, filed Nov. 26, 2019, designating the United States of America and published in English as International Patent Publication WO 2020/109989 on Jun. 4, 2020, which claims the benefit under Article 8 of the Patent Cooperation Treaty to Indian Patent Application number 201811044487, filed Nov. 26, 2018, the entireties of which are hereby incorporated by reference.

FIELD OF INVENTION

The present invention relates to a method for preparing solid lipid nanoparticles of curcumin. More particularly, the invention relates to an efficient entrapment of curumin within the core of these nanoparticles in a solubilised form that increases its efficacy.

Background of the Invention and Prior Art

Turmeric, *Curcuma longa* L. (Zingiberaceae family) rhizomes, has been widely used for centuries in indigenous medicine for the treatment of a variety of inflammatory conditions and other diseases (Ammon and Wahl, 1991). Its medicinal properties have been attributed mainly to the curcuminoids and the main component present in the rhizome includes curcumin (diferuloylmethane)-(1,7-bis(4-hydroxy-3-methoxyphenyl)-1,6-hepadiene-3,5-dione) of the following formula:

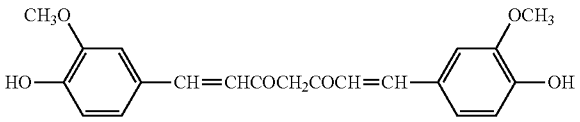

Traditionally, turmeric has been put to use as a foodstuff, cosmetic, and medicine. As a spice, it is used to provide curry with its distinctive yellow color and flavour (Govindarajan, 1980). It is used as a coloring agent in cheese, butter, and other foods (Ammon and Wahl, 1991). In Ayurvedic medicine, curcumin is a well-documented treatment for various respiratory conditions (e.g., asthma, bronchial hyperactivity, and allergy) as well as for liver disorders, anorexia, rheumatism, diabetic wounds, runny nose, cough, and sinusitis (Araujo and Leon, 2001). In traditional Chinese medicine, it is used to treat diseases associated with abdominal pain (Aggarwal et al., 2004). In ancient Hindu medicine, it was used to treat sprains and swelling (Aggarwal et al., 2004). Throughout the Orient, it has traditionally been used as an anti-inflammatory (Aggarwal et al., 2003). Many of its therapeutic effects have been confirmed by modern scientific research. Such effects include antioxidant (Sharma, 1976: Sreejayan and Rao, 1997), anti-inflammatory (Srimal and Dhawan, 1973; Satoskar et al., 1986; Ammon and Wahl, 1991: Brouet and Ohshima, 1995; Dikshit et al., 1995), anti-carcinogenic and antimicrobial (Kiso et al., 1983; Rao et al., 1995: Limtrakul et al., 1997), hepatoprotective (Kiso et al., 1983: Singh et al., 2014), thrombosuppressive (Srivastava et al., 1985), cardiovascular (i.e., as protection against myocardial infarction) (Dikshit et al., 1995: Nirmala and Puvanakrishnan, 1996; Venkatesan, 1998), hypoglycemic (Srinivasan, 1972: Babu and Srinivasan, 1995; Arun and Nalini, 2002), wound healing (Sidhu et al., 1998; Agrawal and Kaur, 2010) and anti-arthritic (i.e., as protection against rheumatoid arthritis (Deodhar et al., 1980). The other salient feature of turmeric/curcumin is that despite being consumed daily for centuries in Asian countries, it has not been shown to cause any toxicity (Ammon and Wahl, 1991).

Further, it is a wonderful natural treatment inside and out for a variety of skin ailments (Nguyen and Friedman, 2013: Thangapazham et al., 2013) including acne, blemishes (Lee et al., 2010; Tu et al., 2012: Arct et al., 2014), hyperpigmentation (Lee et al., 2010; Tu et al., 2012; Arct et al., 2014), black heads, dark circles and other cosmetic applications like fine lines and wrinkles (Demirovic and Rattan, 2011: Lima et al., 2011), skin brightening and lightening.

Although turmeric has been used for thousands of years in alternative medicine, curcumin is yet to emerge as a component of our mainstream dermatologic therapeutic armamentarium. However, in spite of the promising multivariate activities of curcumin, its poor aqueous solubility, poor stability at physiological pH, alkaline pH, photolability as well as its rapid metabolism and systemic elimination, have limited its clinical application.

Over the years, a number of studies have tried addressing the pharmacokinetic issues of curcumin. Latter is poorly absorbed from intestine after oral administration of different doses of 3H-curcumin in rats (Ravindranath and Chandrasekhara, 1980, 1981, 1982). It was shown that oral consumption of curcumin in rats resulted in approximately 75% being excreted in the feces and only traces appeared in the urine (Wahlstrom and Blennow, 1978). Similarly intraperitoneal (i.p) administration accounted for high levels of curcumin excretion in the faeces, with only 11% found in bile (Holder et al., 1978) suggesting poor absorption of curcumin from the intestine. Pharmacokinetic studies in humans have generally produced similar data. Oral dosing of curcumin even at high dose of 4-8 g in one study resulted in very low peak plasma levels of 0.41-1.75 μM in humans (Cheng et al., 2001). In a small study of 15 patients given oral curcumin (36-180 mg) daily for up to 4 months, metabolites were not detected in the blood or urine (Sharma et al., 2001). Garcea et al., 2004 (Garcea et al., 2004) reported only negligible levels of curcumin in blood and liver after daily administration of 3.6 gms of curcumin (as a standard powder extract capsule supplied by Sabinsa Corporation) to the patients. It has been suggested that a person is required to consume large doses (about 12-20 g/day) of curcumin in order to achieve its therapeutic effects on the human body. That means one has to swallow 24 to 40 curcumin capsules of 500 mg each which is practically impossible for human consumption. Such doses are not feasible to be incorporated in clinical trials due to unbearable after-taste to the palate, possibility of giving rise to nauseatic feeling and perceived toxicity issues.

In an effort to address these limitations, various curcumin delivery systems have been investigated. Piperine, a known inhibitor of hepatic and intestinal glucoronidation was combined with curcumin resulting in 154% and 2000% increase in the oral bioavailability of curcumin in rats and humans respectively (Shoba et al., 1998). However, piperine was shown to be toxic in animal studies. Piperine increases curcumin bioavailability by inhibiting glucuronidation which can cause serious health risks. Glucuronidation is protective against many toxins and involved in the metabolism of commonly used drugs. Most elderly patients are on multiple drugs, at levels likely to be unsafely altered by inhibition of glucuronidation. Few attempts have been made to improve solubility of curcumin by its chemical derivatisation (Maing and Miller, 1981: Hergenhahn et al., 2003: Parvathya et al., 2010), complexation or interaction with macromolecules, e.g. gelatin (Schranz, 1981), polysaccharides and protein (Todd, 1991), and cyclodextrin (Tonnesen et al., 2002: Yadav et al., 2010). But slow process of complexation, high molecular weight of cyclodextrins and pH of the processing medium may limit their practical utility. Paradkar et al., 2004 (Paradkar et al., 2004) have reported curcumin-PVP solid dispersion but problem with reproducibility of its physicochemical properties, its formulation into dosage forms and the scale up of manufacturing processes limits it commercial applicability. Liposomes of curcumin are also widely reported by (Li et al., 2005: Karewicz. et al., 2013; Ranjan et al., 2013; Hasan et al., 2014), however, these systems have issues of low stability, drug leakiness, and low encapsulation capability. Nanoemulsions of curcumin is another approach used to enhance bioavailability of curcumin. Wang et al., 2008: Yu and Huang 2012 (Wang et al., 2008: Yu and Huang, 2012) have developed nanoemulsions for improved bioavailability of curcumin. However, use of a large concentration of surfactant and co-surfactant for stabilizing the nano droplets limits this system. A number of polymeric materials including chitosan (Das et al., 2010). poly(ethyleneglycol) monoacry late (PEG-A) (Bisht et al., 2007), poly(D,L-lactic-co-glycolic acid) (Shaikh et al., 2009; Anand et al., 2010), poly (N-vinylcaprolactam) (Rejinold et al., 2011) have been used for the preparation of curcumin loaded nanoparticles. However, the only USFDA approved polymers are chitosan and PLGA. Latter is a costly polymer. Furthermore, these polymers are soluble in organic solvents and hence the latter are almost always involved in their preparation. Complete removal of these organic solvents cannot be ensured and several of them may have toxic implications, even when present in small amounts. Anuchapreeda et al., 2012 (Anuchapreeda et al., 2012) have reported the lipid nanoemulsion of curcumin but the possibility of controlled drug release from lipid nanoemulsions is limited due to the small size and the liquid state of the carrier. For most drugs, a rapid release of the drug will be observed.

Solid lipid nanoparticles (SLNs) represent a relatively novel type of colloidal drug delivery system that combines the merits of liposomes and polymeric nanoparticles. Therefore, SLNs provide both stability of the solid matrix and biological compatibility of the lipid carriers while avoiding the shortcomings of liposomes, which include undesired stability problems, and polymeric nanoparticles, which are subject to the potential toxicity of the materials. Other advantages over other colloidal carriers, include possibility of controlling drug release, drug targeting. significant drug loading (whether hydrophilic or lipophilic) and easy large scale production. In addition, due to their nano size range, SLNs tend to enhance absorption, improve bioavailability, prolong the retention time, and provide a sustained drug release profile. Other advantages offered by SLNs include biodegradability, safety, low cost. simple production techniques, and most importantly, free dispersibility in aqueous media. The use of solid lipids instead of liquid oils is a very attractive idea to achieve controlled drug release, because drug mobility in a solid lipid should be considerably lower compared with liquid oil. Various attempts have been made for the preparation of solid lipid nanoparticles of curcumin using different methods of preparation.

Kakker et al., 2011 (Kakkar and Kaur, 2011) have reported curcumin loaded solid lipid nanoparticles with microemulsification method with high amount of Tween 80 such that the total amount consumed/day may exceed $LD_{50}$ or limits of safety. Curcumin loaded solid lipid nanoparticles have also been prepared by solvent injection method as reported by Wang et al., 2012, Chen et al., 2013, Wang et al., 2013 (Chen et al., 2013: Wang et al., 2013) but organic solvents are employed in this method. High pressure homogenisation has also been employed in the preparation of solid lipid nanoparticles. Sun et al., 2013 (Sun et al., 2013) have prepared solid lipid nanoparticles of curcumin using Dynasan 1148, Sefsol-218 as lipid phase with very low drug loading i.e. 0.74%. Similarly curcumin loaded solid lipid nanoparticles with low drug loading have also been reported by Tiyaboonchai et al., 2007 and Noack et al., 2013 (Tiyaboonchai et al., 2007: Noack et al., 2012)

CN102949344A discloses application of curcumin solid lipid nano-particles for effectively treating asthma. The syringeability of curcumin can be improved, the bioavailability of curcumin can be improved by about 30 times, and the lung targeting of curcumin can be improved by loading curcumin with solid nano-lipisome.

CN103655519A discloses a curcumin solid lipid nanoparticle with a P-gp inhibiting effect, and a preparation method and application thereof. The curcumin solid lipid nanoparticle comprises the following components according to mass ratio: 0.05-1% of curcumin, 5-15% of lipid material, 5-15% of an emulgator and the balance of water. The preparation method of the curcumin solid lipid nanoparticle is the emulsification evaporation and low temperature solidification method which is simple and convenient and suitable for being used in a laboratory, and has low requirements for an apparatus. Organic solvent is used in the above patent.

CN103784421A discloses curcumin and piperine carried solid lipid nanoparticles. The curcumin and piperine carried solid lipid nanoparticles are prepared from 0.1-5% of curcumin, 0.1-5% of piperine, 10%-70% of solid lipid material, 5%-30% of liquid oil phase, 10%-60% of emulsifier and the balance of water by weight percentage. A preparation method of the curcumin and piperine carried solid lipid nanoparticles can be a thin film dispersion method, a microemulsion method or an emulsifying evaporation-low temperature solidification method.

The document teaches use of PiperineandOrganic solvent.

CN103989659A discloses a formula of a lipid carrier of curcumin in a nano structure and a preparation method of the lipid carrier. The lipid carrier of curcumin in the nano structure extremely overcomes the deficiencies that curcumin is difficult to be dissolved in water, low in oral bioavailability, fast in metabolism and the like, provides a novel selectable transfer system for curcumin. Liquid lipids are used in the above patent whereas polyethylene glycol 600 is not covered.

CN 201310723889 relates to a method for preparing a curcumin lipid nano-particle suspension or nano-particles, and belongs to the technical field of medicinal preparations. The method comprises the steps of: dissolving 1 part by weight of curcumin and 5-20 parts by weight of amphoteric degradable high-molecular polymer into an organic solvent to form a lipid phase solution: dissolving 5-20 parts by weight of surfactant in water to form an aqueous phase solution: injecting the lipid phase solution and the aqueous phase solution into a micro-passage of a passage reactor to mix the lipid phase solution and the aqueous phase solution into particles, wherein the aqueous phase flow velocity is 0.65-0.75 mL/min, and the lipid phase flow velocity is 0.2-0.5 mL/min: removing the organic solvent to obtain the curcumin lipid nano-particle suspension. This patent document uses organic solvent.

US 2009/0324703A1 discloses curcuminoid formulations having enhanced bioavailability are provided and comprise a curcuminoid, antioxidant, glucuronidation inhibitor, and water-soluble, pharmaceutically acceptable inhibitor. The curcuminoid formulations can be in the form of a solid lipid nanoparticle. However, polyethylene glycols are not used in preparation of solid lipid nanoparticles in the patent.

WO2014135967A1 discloses solid lipid particles comprising a lipid hydrophobic matrix and from about 5 wt. % to about 30 wt. % of curcumin, and methods of making and treatment thereof.

US 2013/0017239A1 discloses a delivery system for active ingredients which comprises lipid nanoparticles, such as solid lipid nanoparticles (SLN) or nanostructured lipid carriers (NLC), polymerically coated, and their use in the preparation of pharmaceutical, cosmetic and/or alimentary compositions. The prepared solid lipid nanoparticles are coated with a polymer in the above patent.

There remains a need for the preparation of a solid lipid nanoparticle for curcumin which shows high entrapment efficiency of the curcumin and also results in higher bioavailability of the curcumin.

OBJECT OF THE INVENTION

Accordingly, it is an object of the present invention to provide a simple and convenient process for preparing curcumin loaded solid lipid nanoparticles using Generally Recognised as Safe (GRAS) components, which has improved bioavailability and stability.

It is another object of the present invention to prepare solid lipid nanoparticle with high total drug content and drug loading.

It is another object of the present invention to provide a controlled release formulation of curcumin leading to reduction in dose and frequency of administration.

It is another object to provide a curcumin in a solubilised form as an aqueous dispersion.

It is a further object of the present invention to achieve effective delivery of curcumin via oral, aerosol, parenteral, vaginal, intranasal, buccal, dental, transdermal and topical administration.

It is another object of the present invention to develop a formulation which can be sterilised by autoclaving, if needed for specific application viz wound dressing, ocular, implants and parenteral.

It is another object to formulate a water washable system so that curcumin if stains the skin or cloth following application/administration can be easily rinsed off with water.

SUMMARY OF THE INVENTION

In an aspect of the present invention, there is provided a process for preparing solid lipid nanoparticles of curcumin, the process comprising the steps of:

a. dissolving curcumin in a co-solvent to obtain a solution and maintaining the solution at temperature 10° C. above lipid melting point temperature;
b. adding melted lipid or mixture of lipid selected form group consisted of glycerides and fatty acids to the solution obtained in step (a) to obtain a hot lipid phase;
c. preparing an aqueous surfactant phase comprising water, surfactant and co surfactant and maintaining the aqueous surfactant phase at a temperature 10° C. above lipid melting temperature;
d. adding the hot lipid phase of step (b) to the aqueous surfactant phase of step (c) and mixing at high speed of4000-15000 rpm for 5-10 min to obtain a primary coarse emulsion; and
e. subjecting the primary coarse emulsion of step (d) to two to six cycles of homogenization at 500 to 1200 bars to obtain solid lipid nanoparticles of curcumin.

In another aspect of the present invention there is provided Solid lipid nanoparticles of curcumin as prepared by the process as described herein.

BRIEF DESCRIPTION OF ACCOMPANYING DRAWINGS

Figure 3:
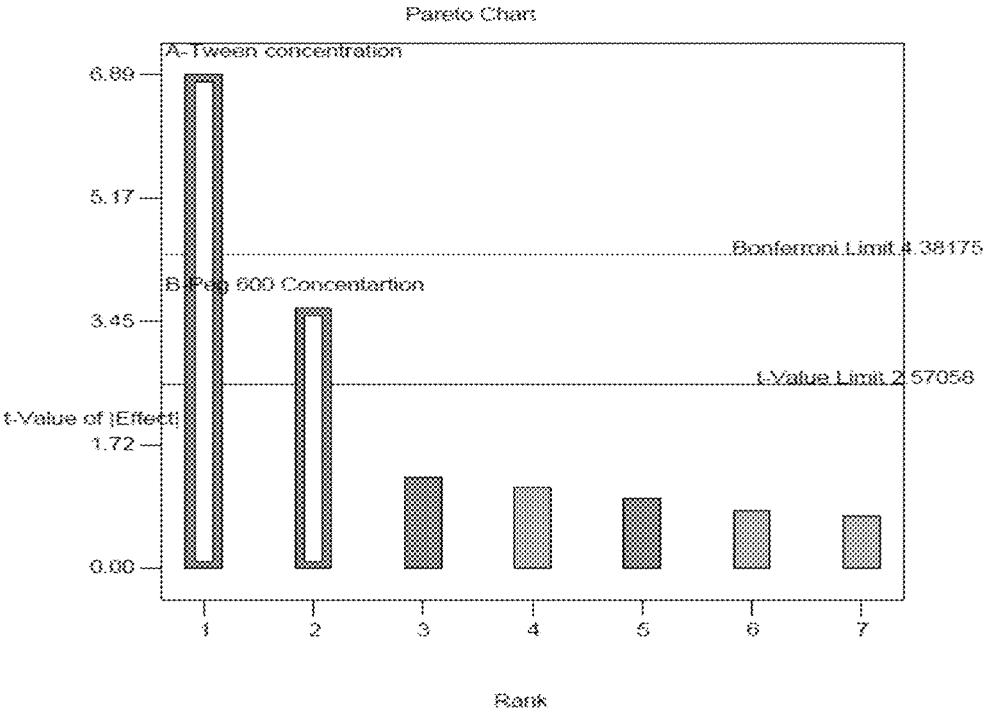

FIG. 3 illustratesPareto chart for PDI

Figure 4:
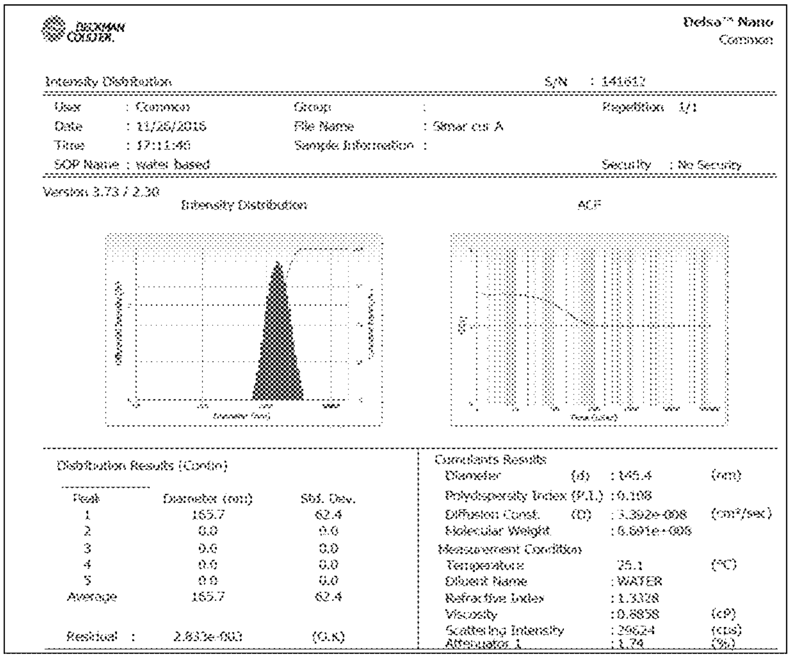

FIG. 4 illustratesParticle size and PDI of C-SLNs

Figure 5:
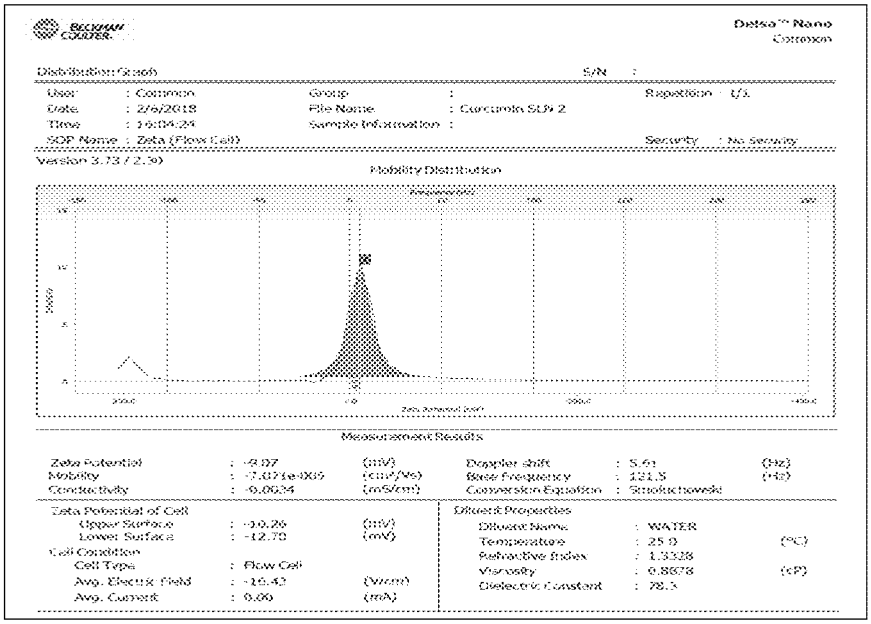

FIG. 5 illustrates Zeta potential of optimised formulation

Figure 6:
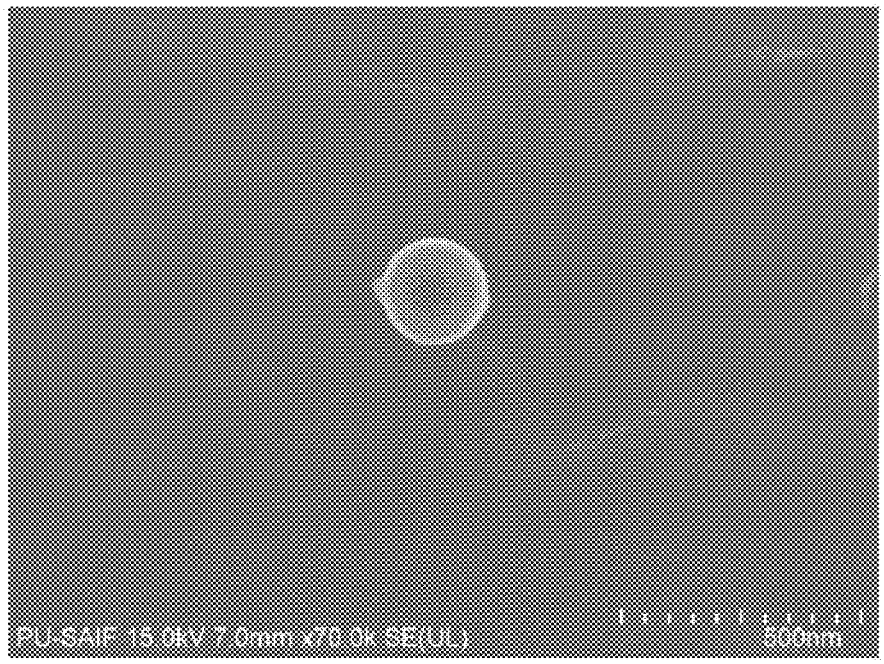

FIG. 6 illustrates FESEM of C-SLNs

Figure 7:
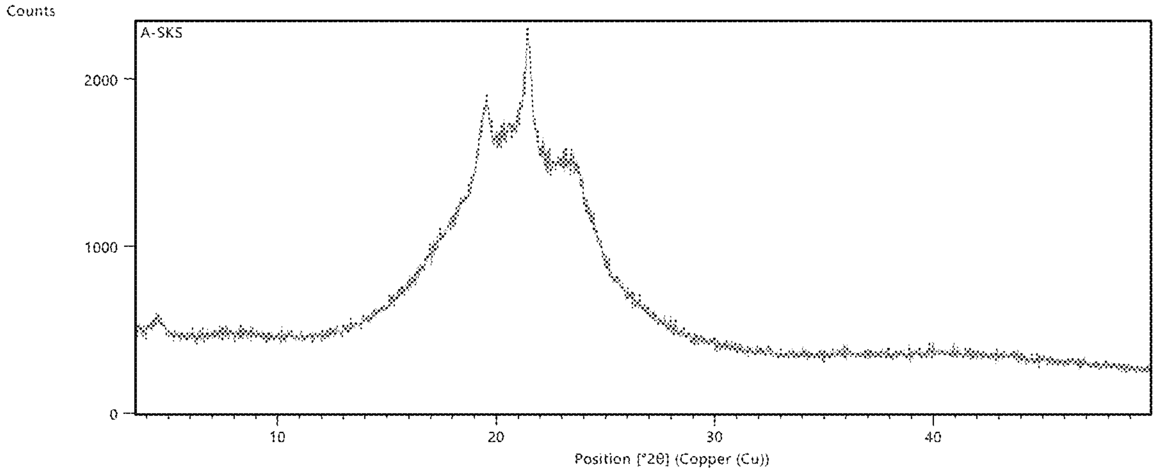
Figure 7:
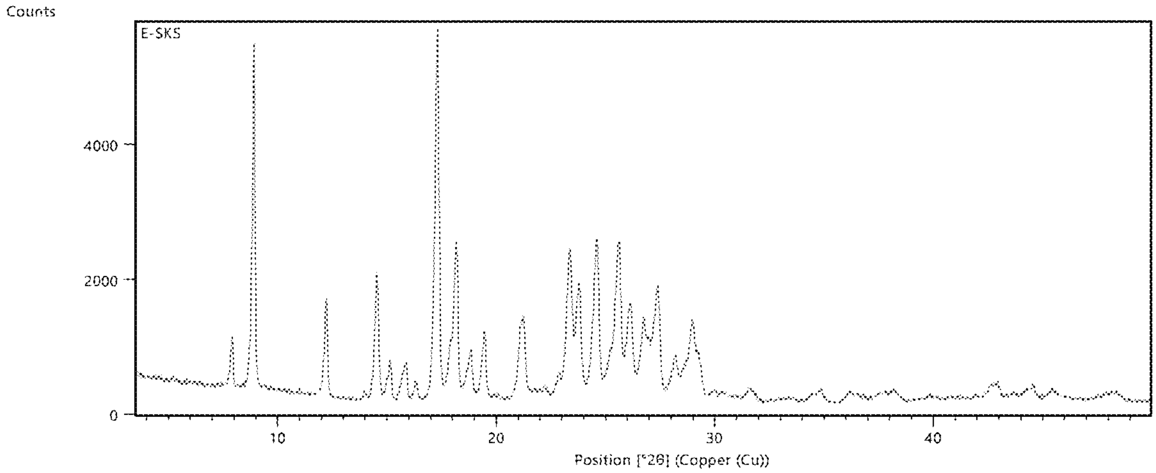

FIG. 7 illustrates PXRD pattern of (a) CSLNs and (b) free curcumin

Figure 8:
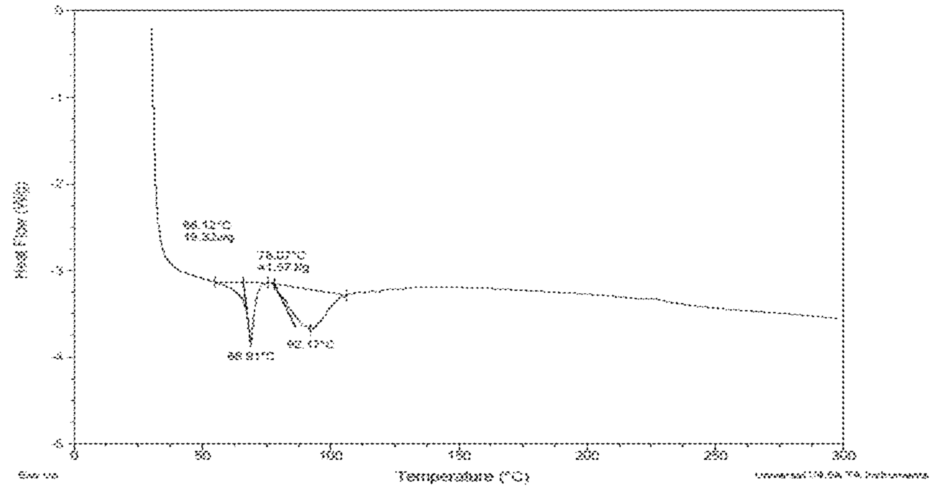
Figure 8:
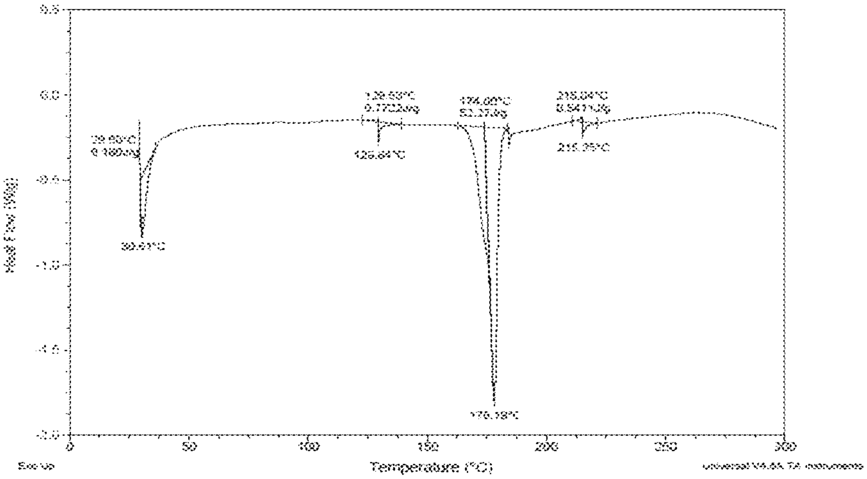
Figure 8:
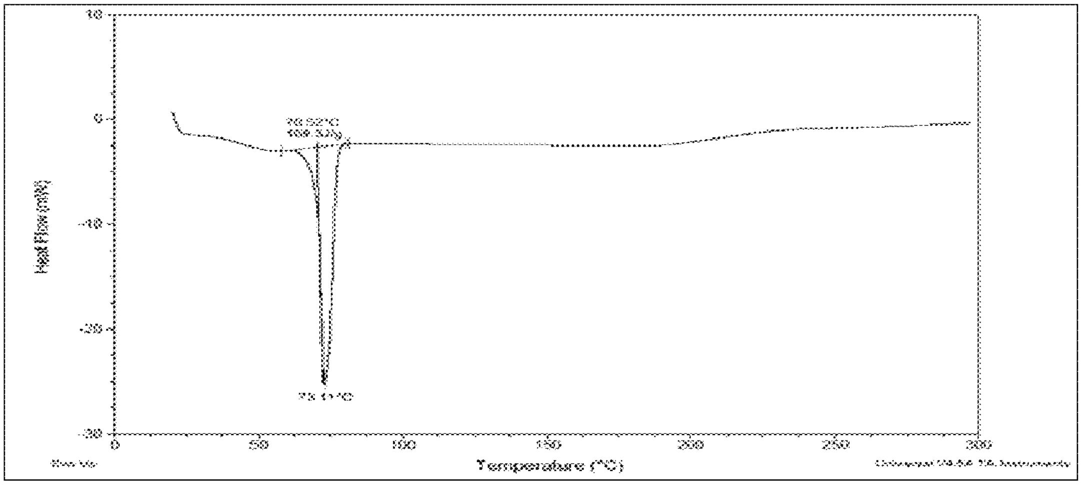

FIG. 8 illustrates DSC of (a) CSLNs, (b) free curcumin and (c) Compritol ATO 888

Figure 9:
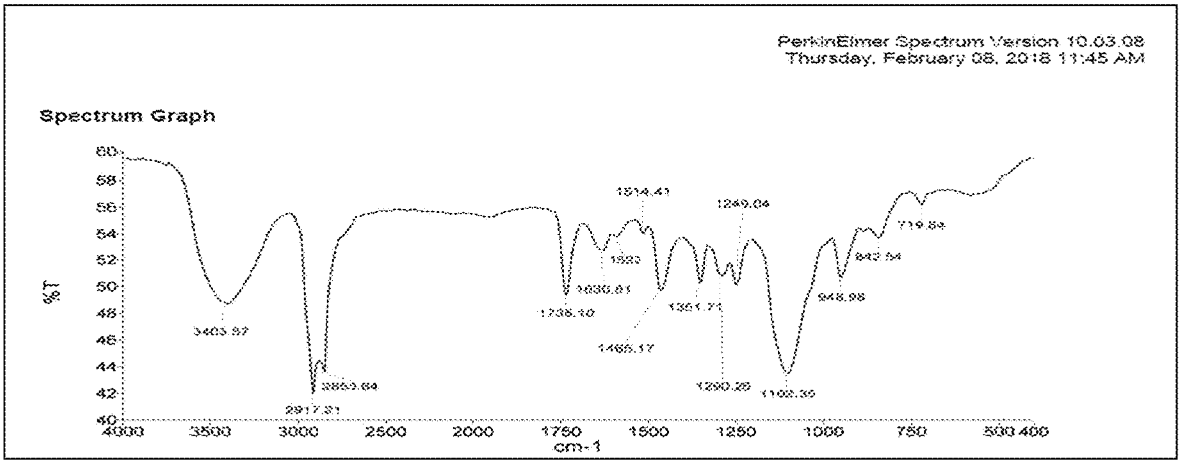
Figure 9:
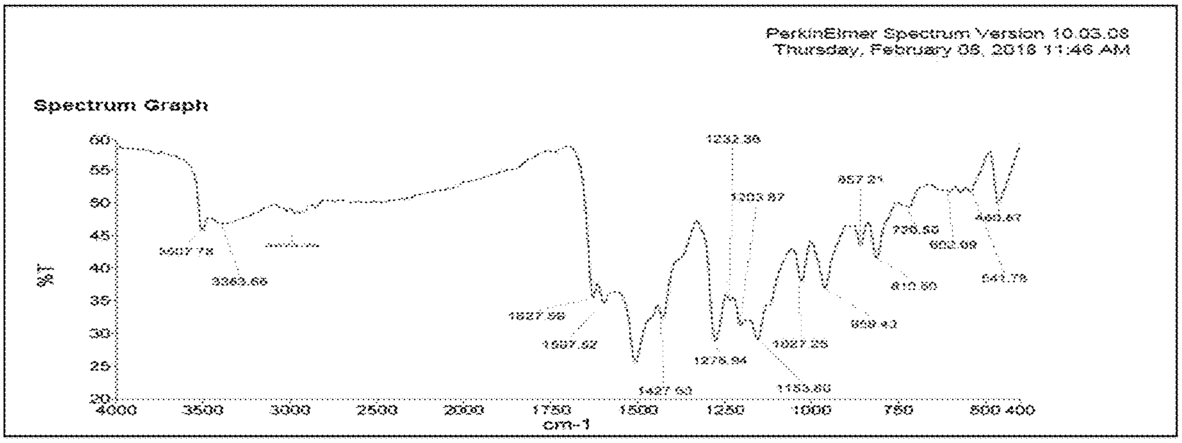
Figure 9:
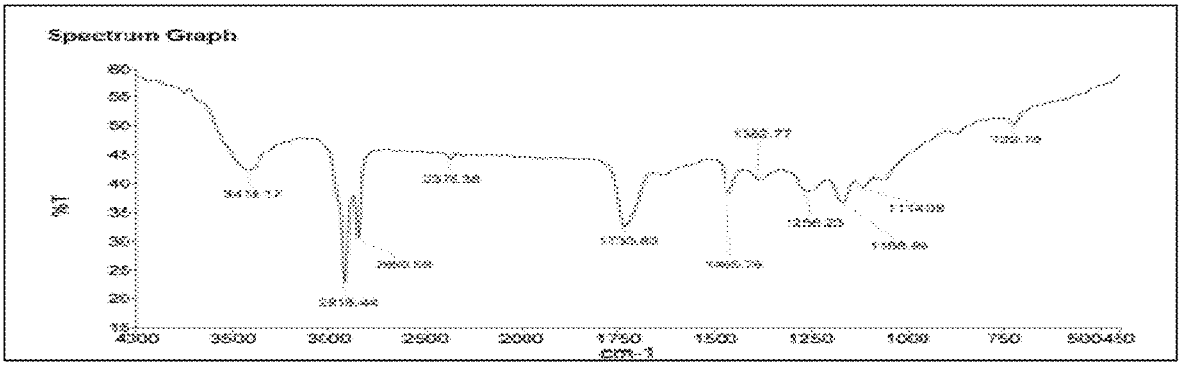
Figure 10:
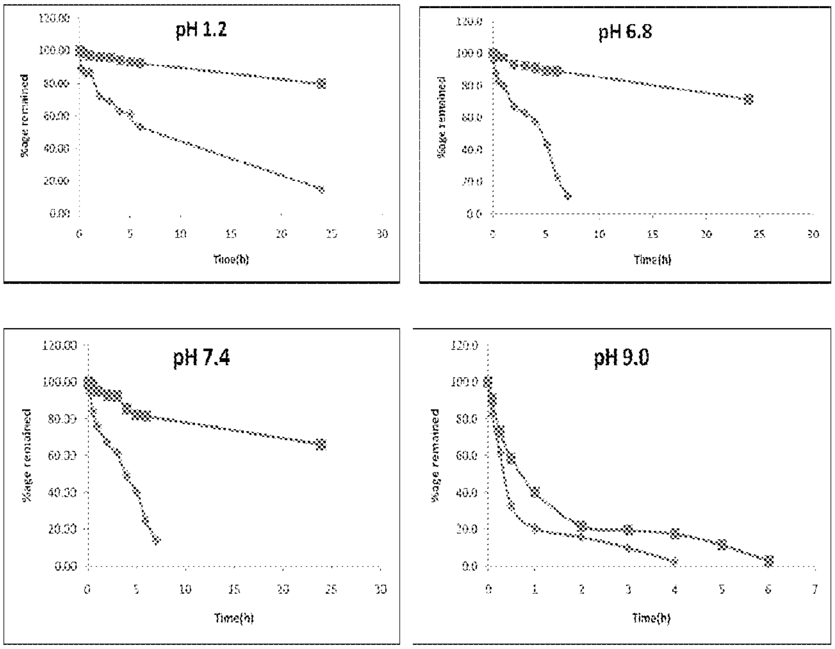
Figure 11:
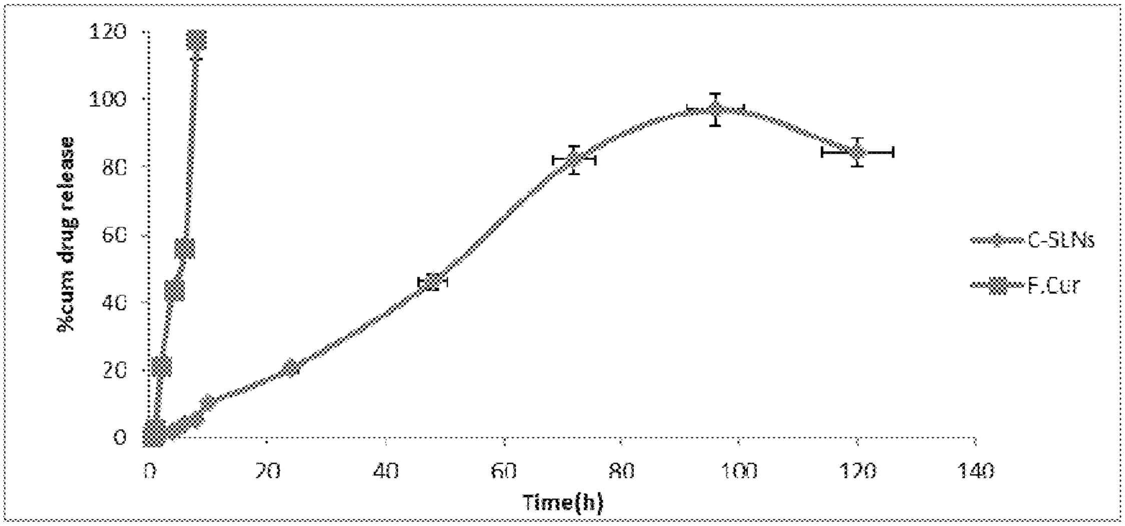
Figure 12:
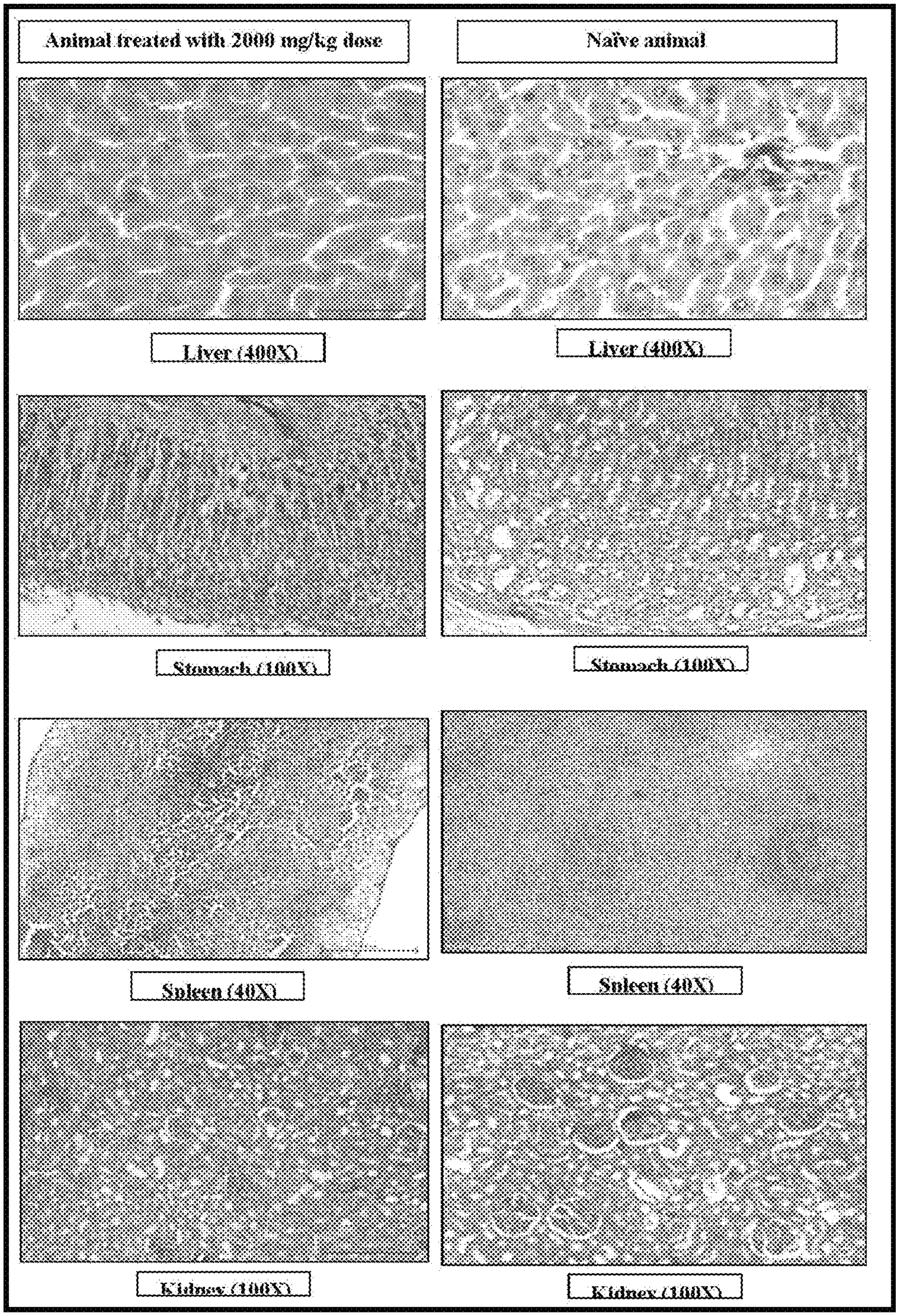
Figure 12:
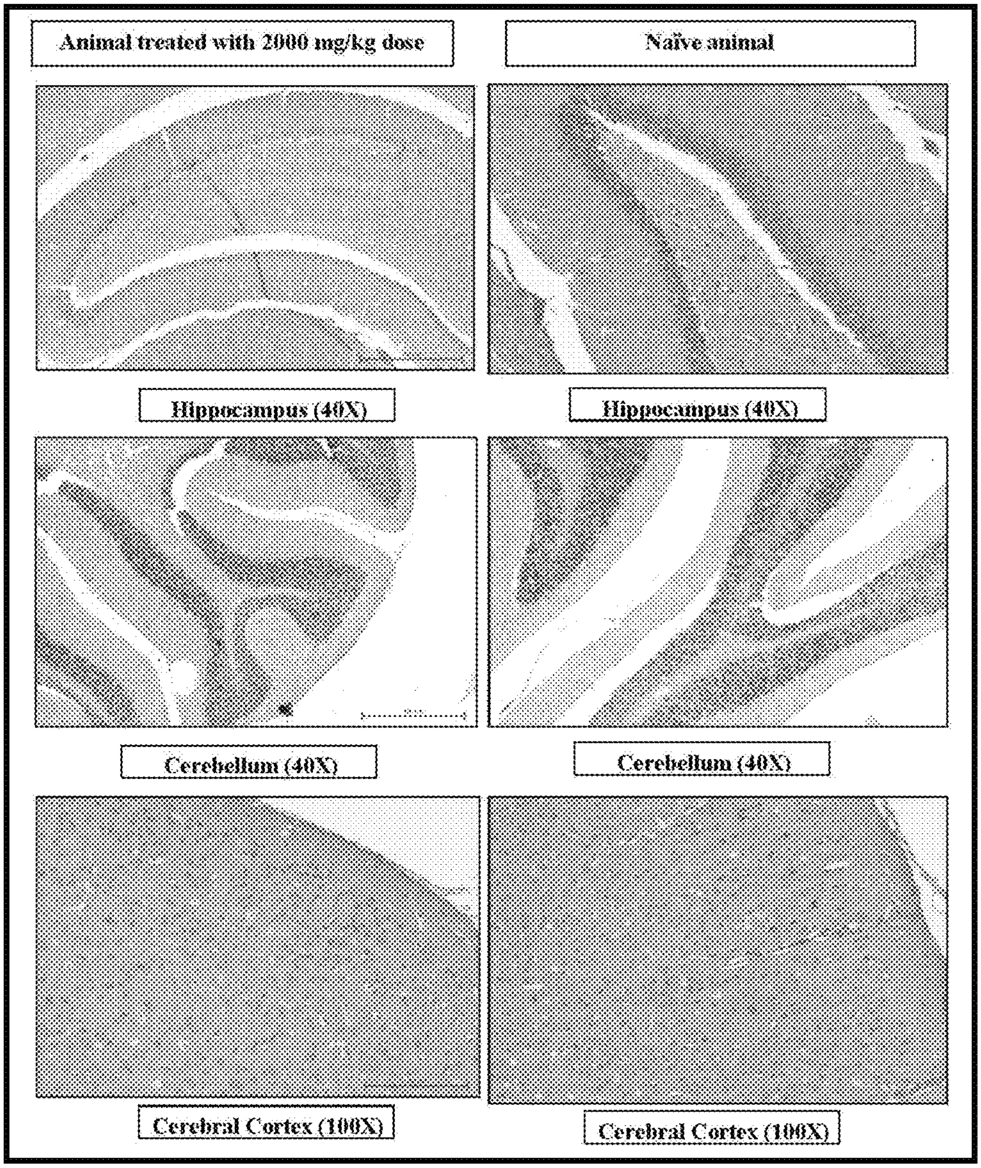
Figure 13:
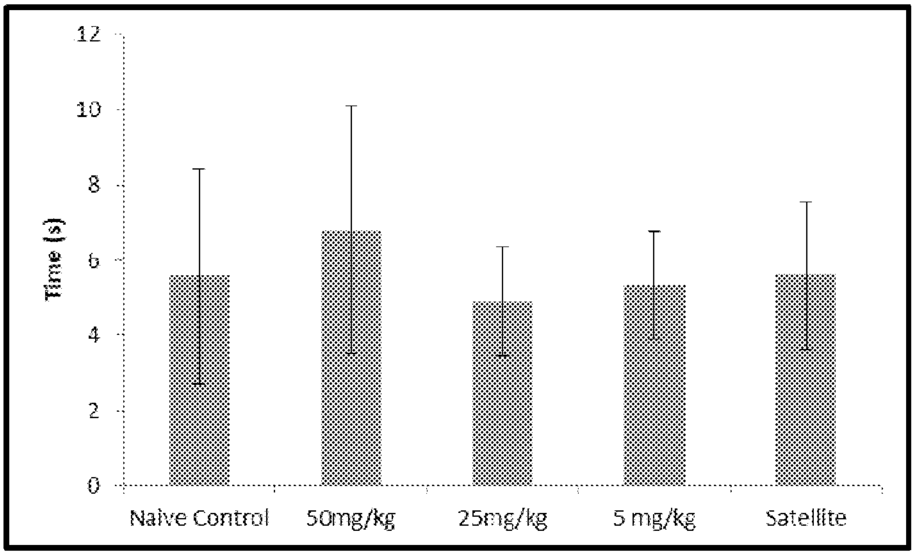
Figure 14:
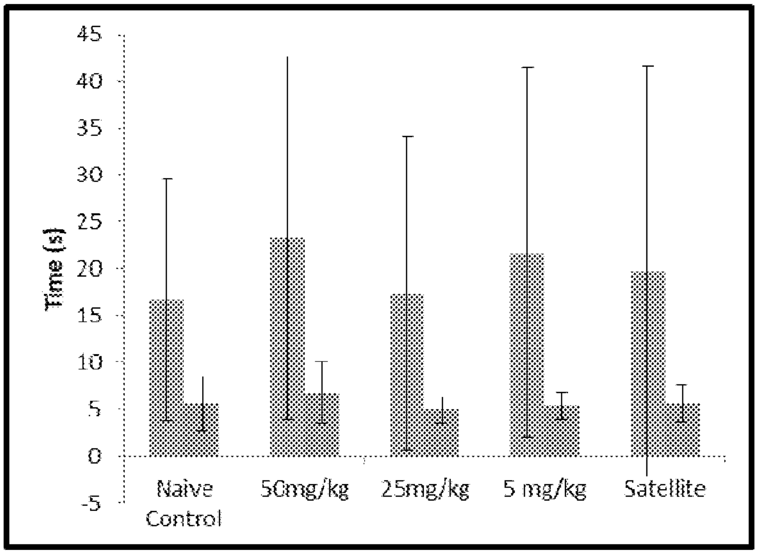
Figure 15:
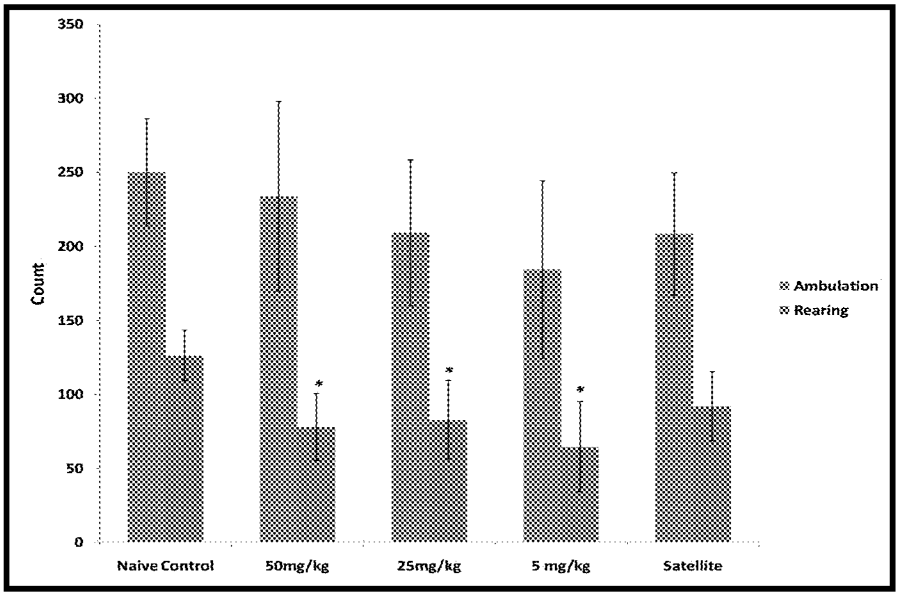
Figure 16:
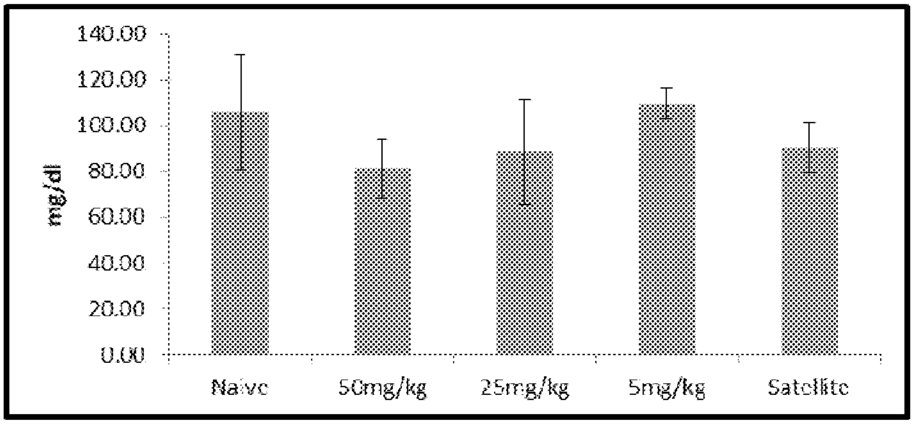
Figure 17:
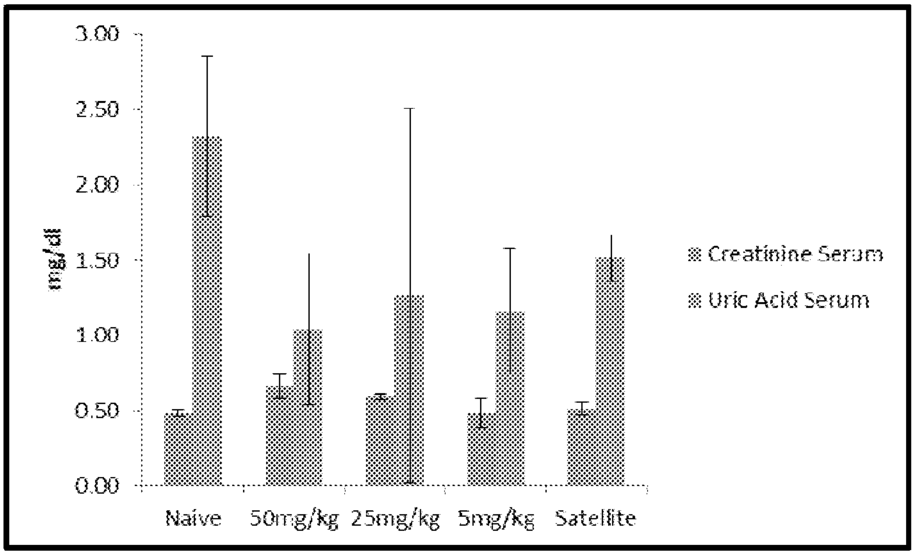
Figure 18:
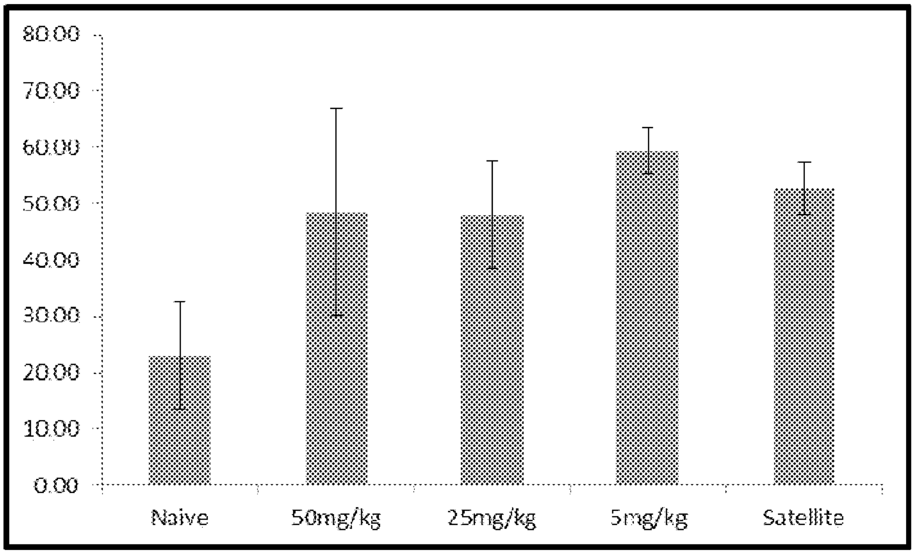
Figure 19:
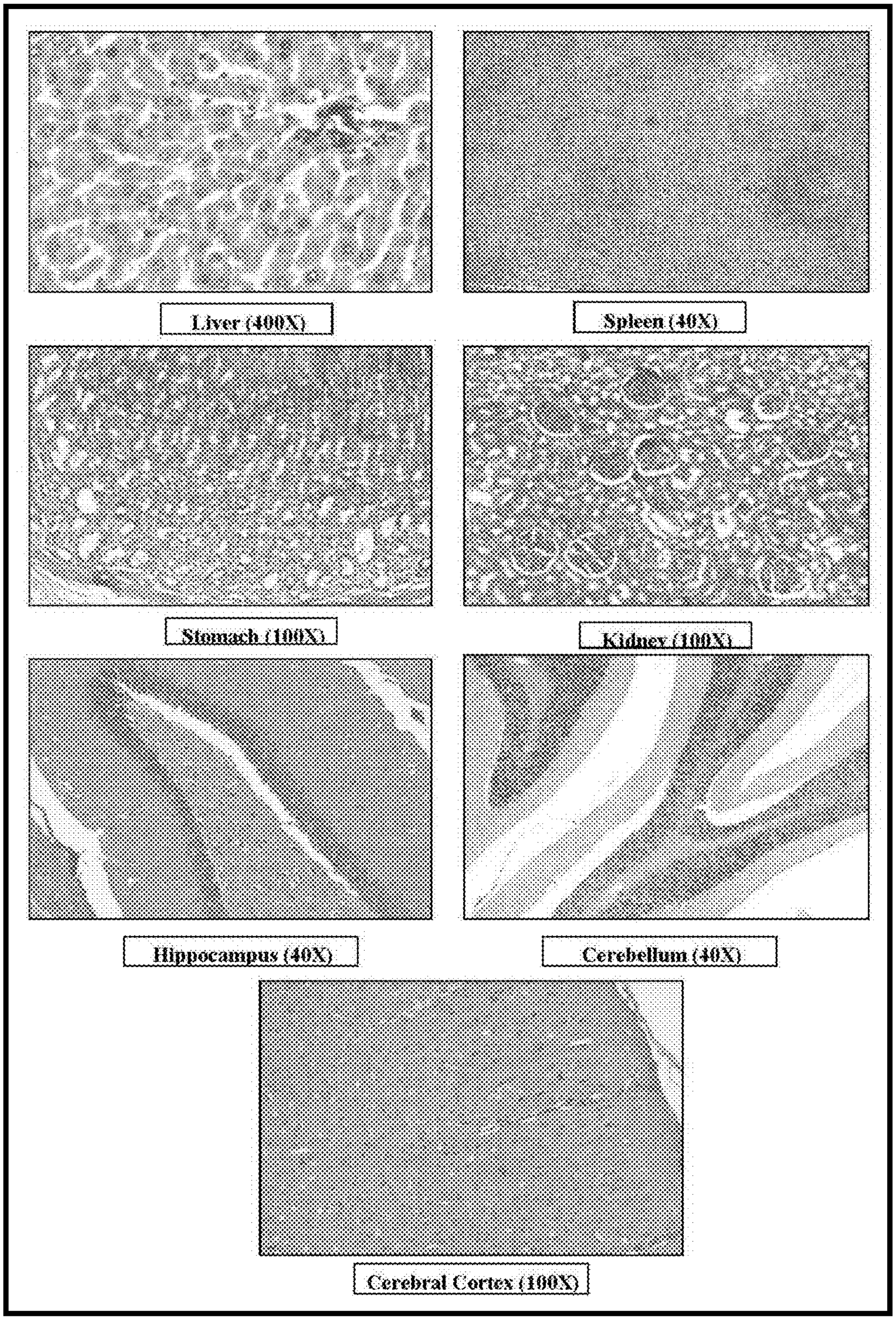
Figure 20:
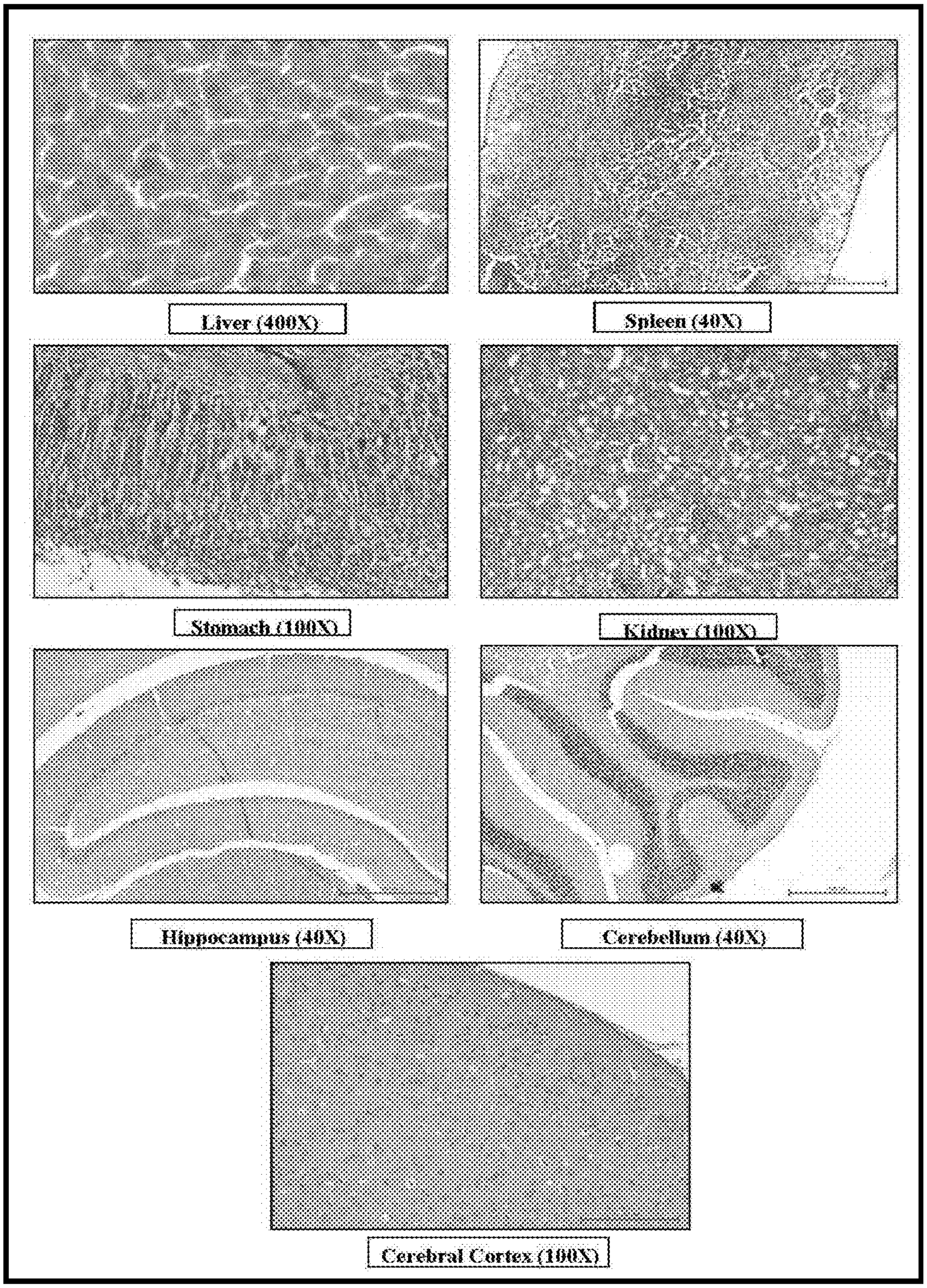
Figure 21:
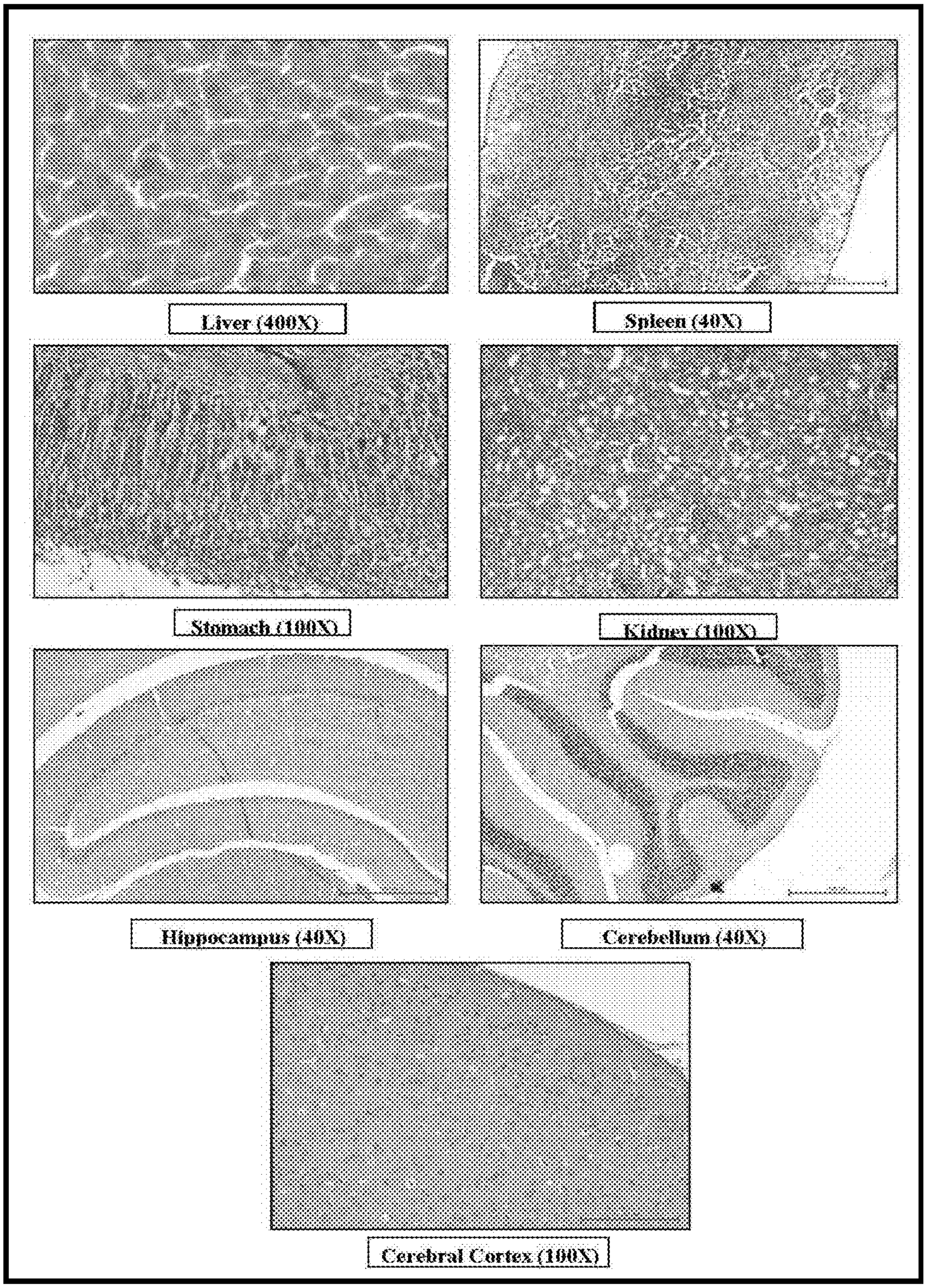
Figure 22:
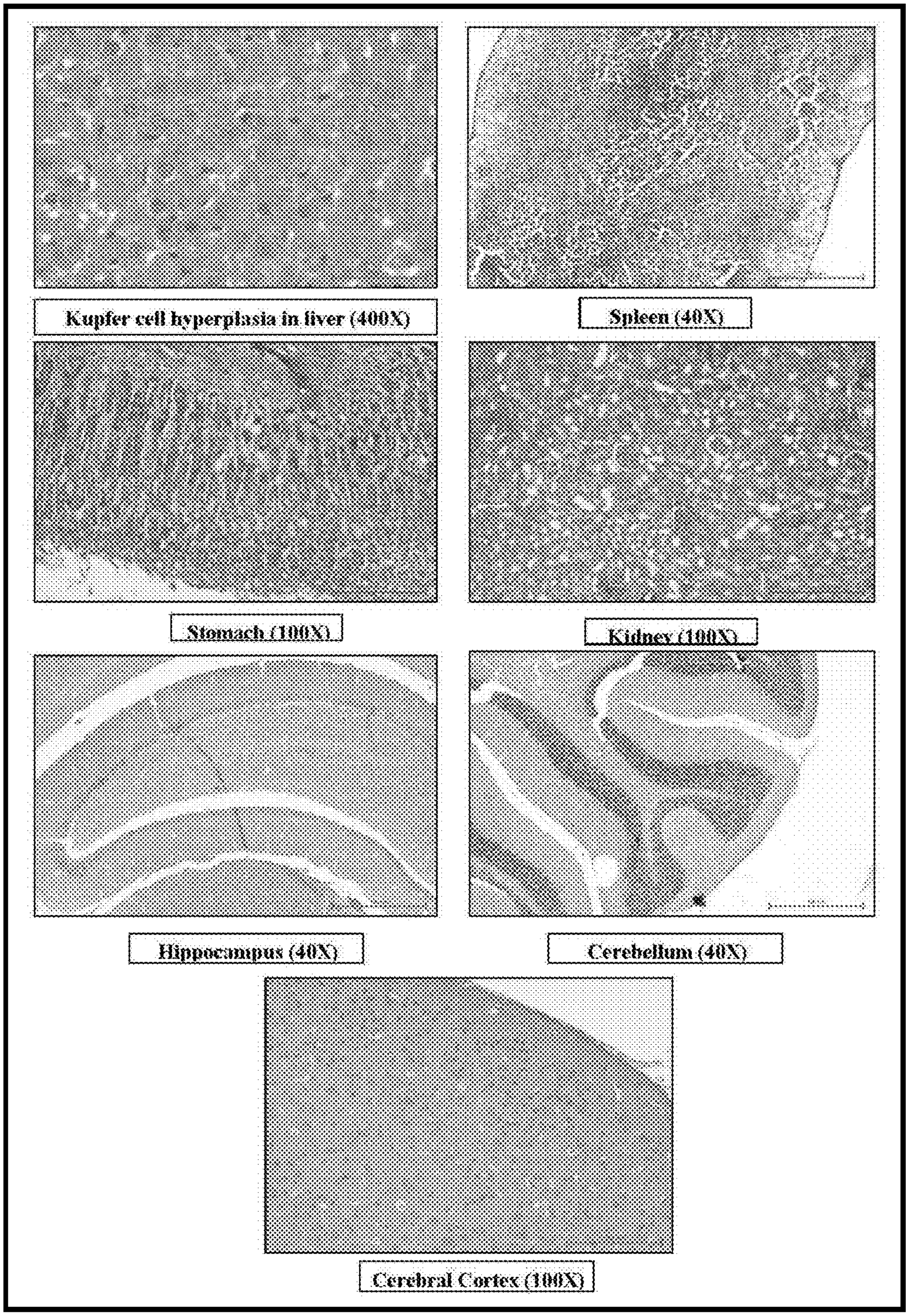
Figure 23:
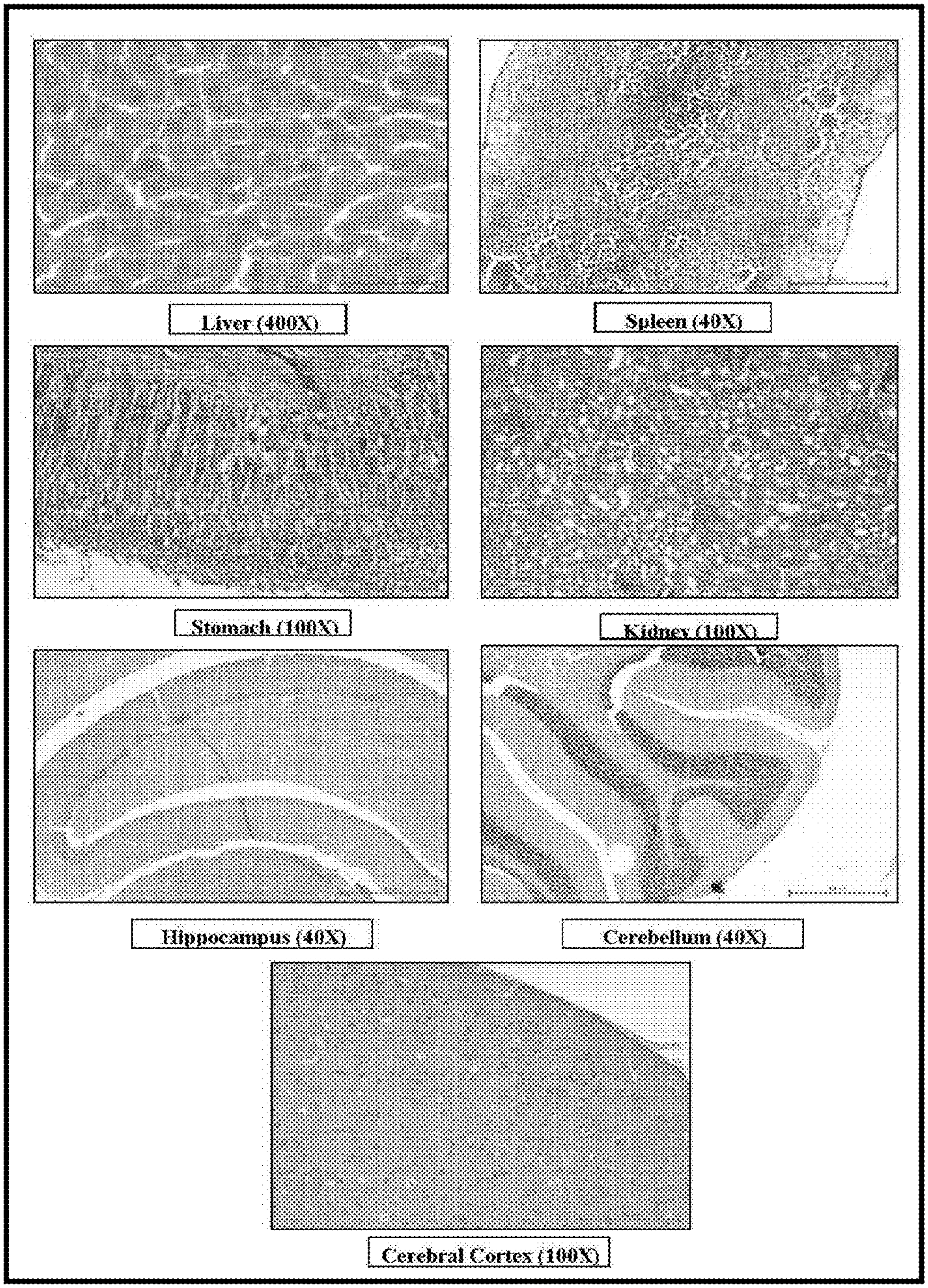
Figure 24:
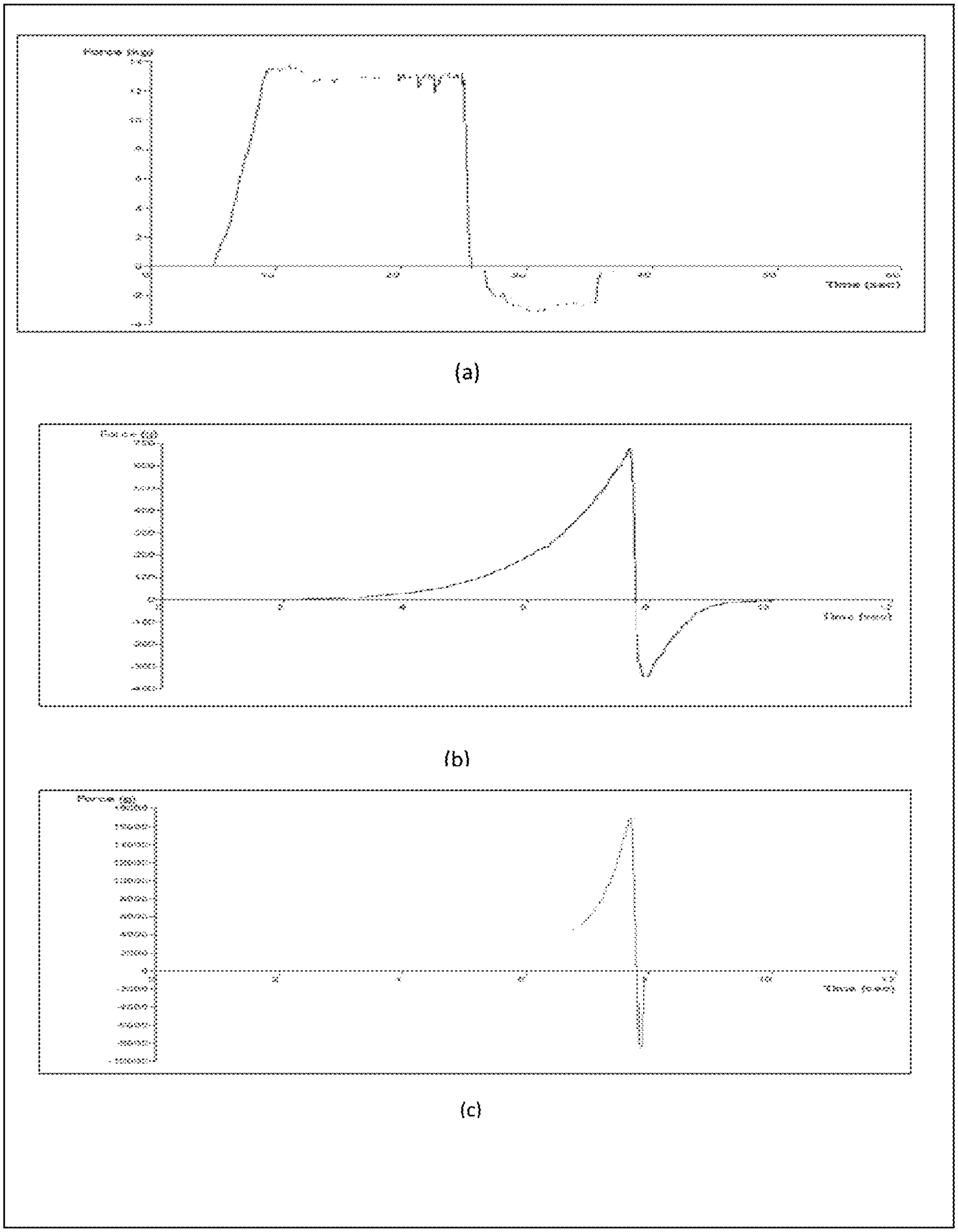
Figure 25:
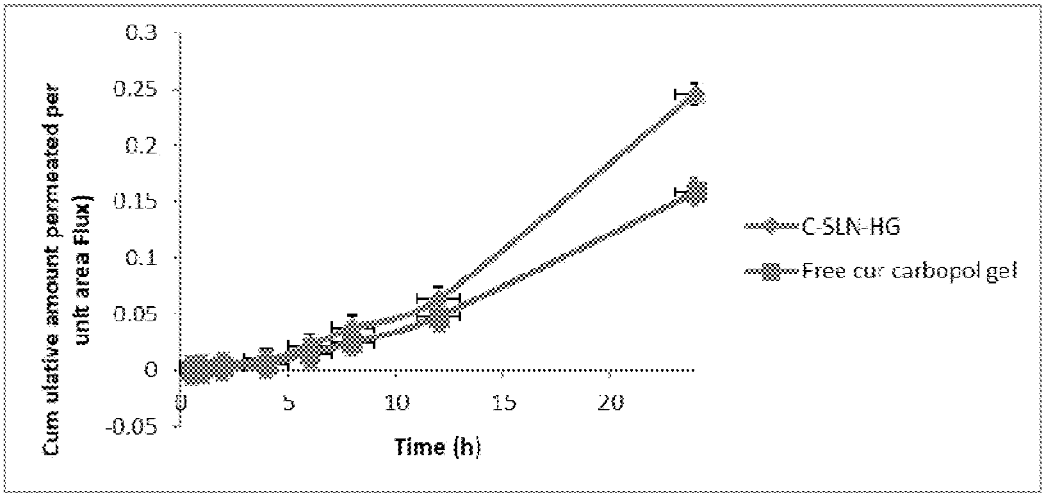
Figure 26:
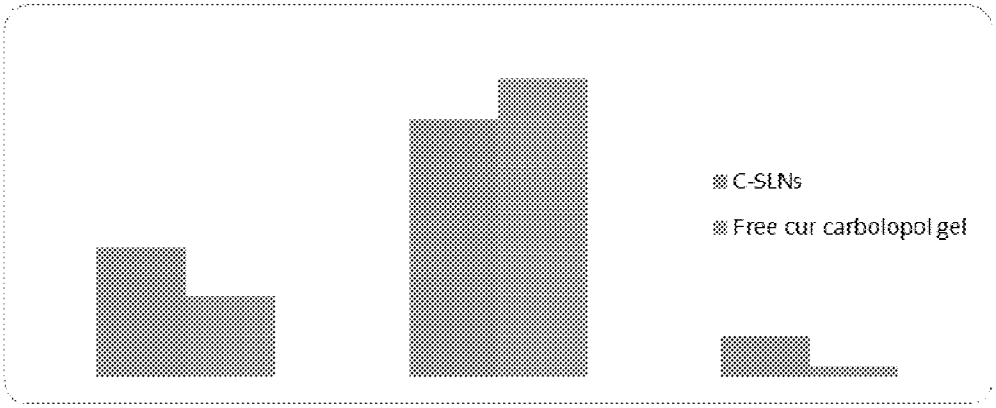
Figure 27:
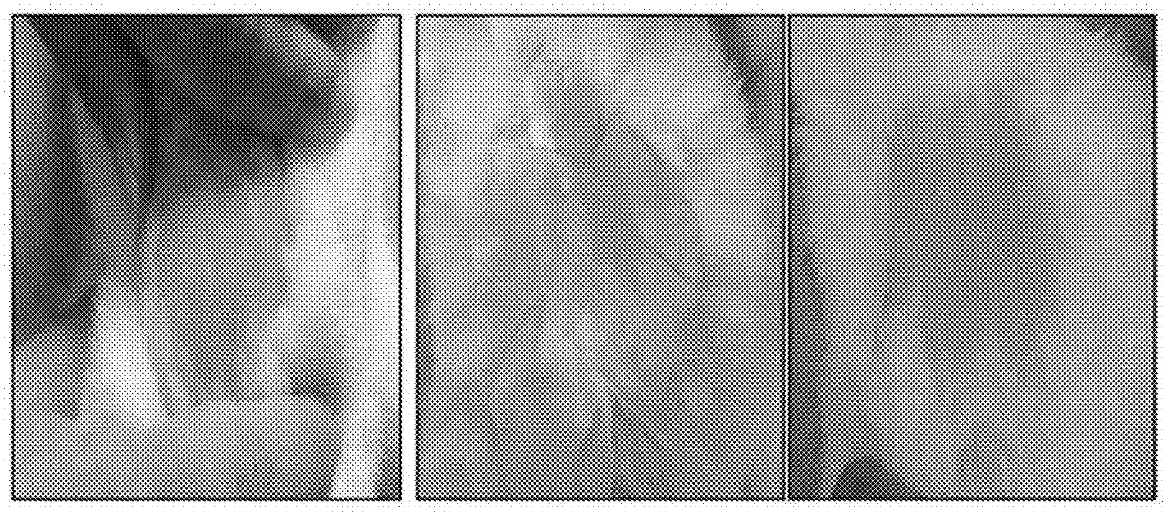
Figure 28:
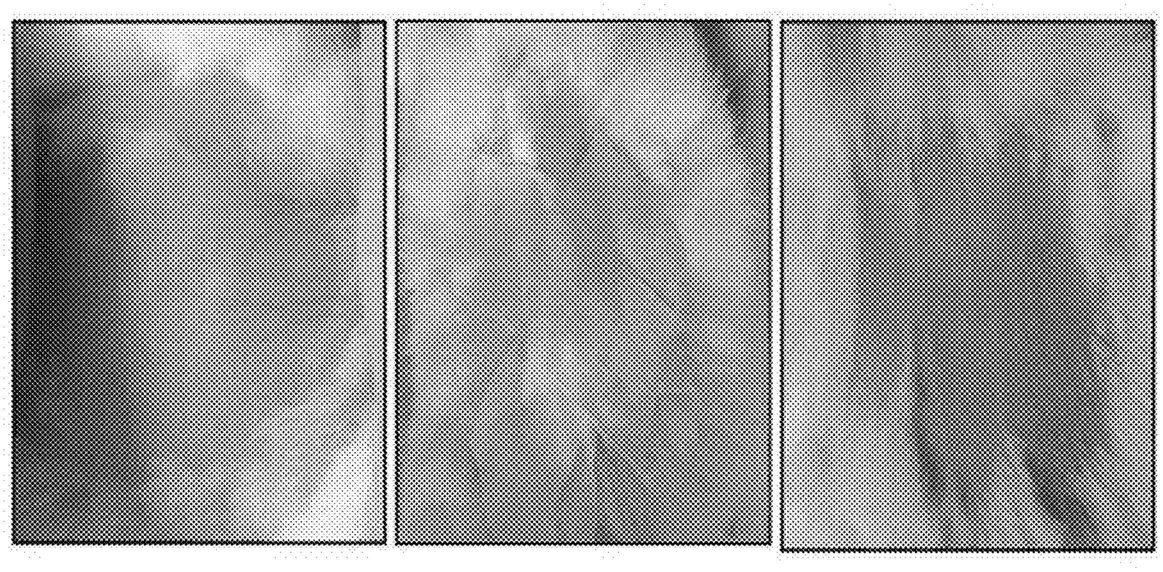
Figure 29:
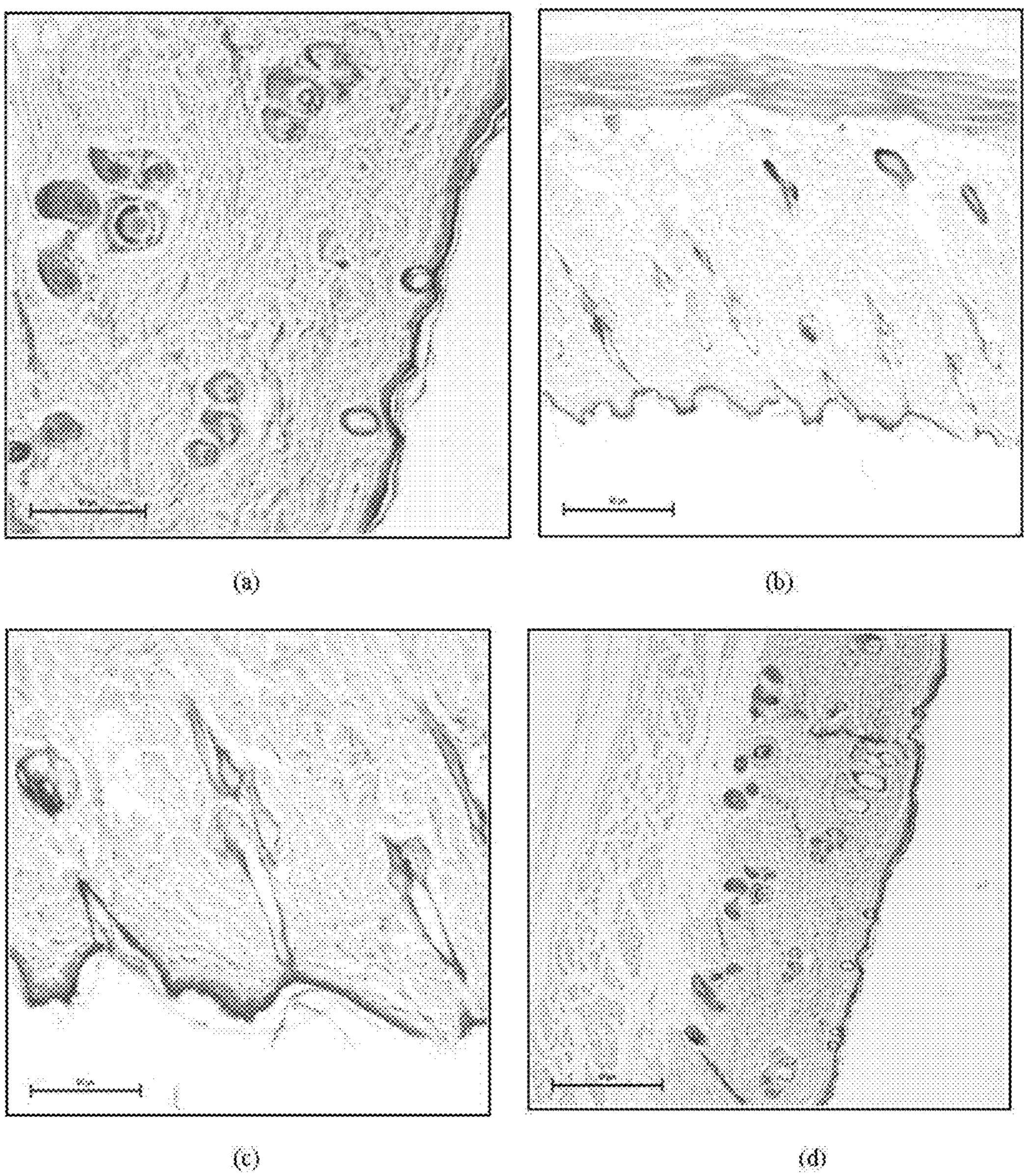

FIG. 9 illustrates FTIR spectra of (a) CSLNs, (b) free curcumin and (c) compritol ATO FIG. 10 illustrates % remaining of curcumin versus time plot at various pH FIG. 11 illustrates in vitro release profile of curcumin, from C-SLNs and free curcumin FIG. 12 illustrates (a) Histological sections of various organs of animals undergoing acute toxicity studies at 2000 mg/kg versus naive control animal, (b) illustrates Histological sections of various organs of animals undergoing acute toxicity studies at 2000 mg/kg versus naive control animal FIG. 13 illustrates Paw withdrawal latency of animals FIG. 14 illustrates Time taken by animals on rota rod FIG. 15 illustrates Locomotor activity of animals FIG. 16 illustrates Blood sugar of animals of various dose groups FIG. 17 illustrates Creatinine serum and uric acid serum levels of various dose groups FIG. 18 illustrates Urea blood level of animals of various dose groups FIG. 19 illustrates Histological report of animal of naive control group FIG. 20 illustrates Histological report of animal at 5 mg/kg FIG. 21 illustrates Histological report of animal at 25 mg/kg FIG. 22 illustrates Histological report of animal at 50 mg/kg FIG. 23 illustrates Histological report of animal of satellite group at 50 mg/kg FIG. 24 illustrates (a) Graph showed backward extrusion of C-$SLN_{HG}$ (b) spreadability of C-$SLN_{HG}$ and (c) spreadability of C-$SLN_{bent}$ FIG. 25 illustrates Cumulative amount permeated per unit area of rat skin (n=6) versus time FIG. 26 illustrates average amount of % absorbed, unabsorbed and amount retained in the skin following C-$SLN_{HG}$ and free cur in carbopol gel at 24 h post application FIG. 27 illustrates skin of animals before, with and after the application of CSLNhg FIG. 28 illustratesskin of animals before, with and after the application of CSLNben FIG. 29 illustrates histology of skin applied with (a) and (b) CSLNhg and (c) and (d) CSLNbent.

Figure 30:
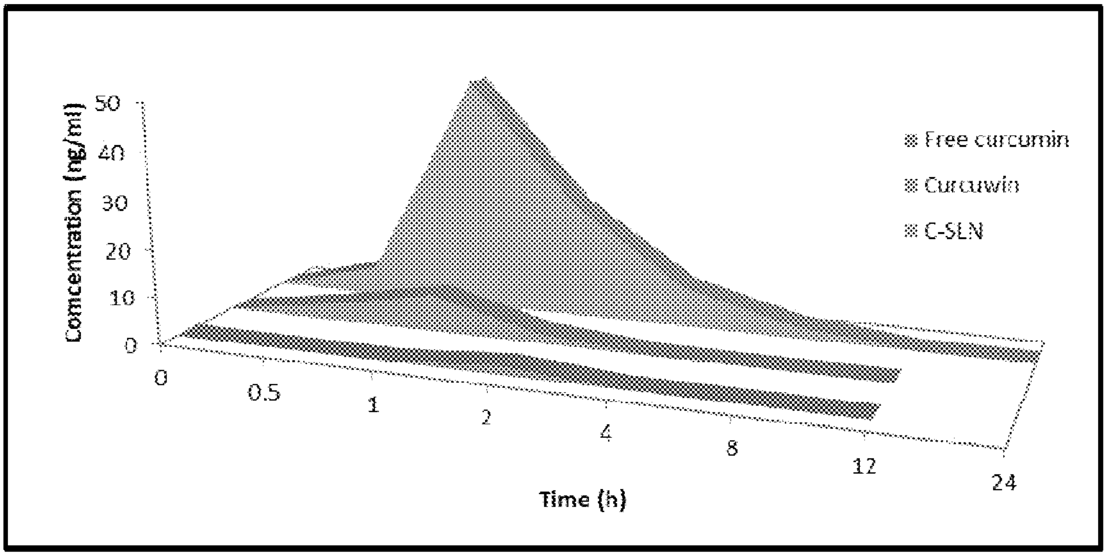

FIG. 30 illustrates mean concentration-time area curve of curcumin in rat after single oral dose of free curcumin, CurcuwinR and C-SLNs

DESCRIPTION OF THE INVENTION

The present invention deals with development of solid lipid nanoparticles (SLNs) of curcumin.

The following description with reference to the accompanying drawings is provided to assist in a comprehensive understanding of exemplary embodiments of the invention. It includes various specific details to assist in that understanding but these are to be regarded as merely exemplary. Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

As used herein, the "curcumin" refers to curcumin, desmethoxycurcumin and bisdesmethoxycurcumin, tetrahydrocurcumin, curcumin analogues, curcumin complexes, curcumin derivatives including but not limiting to polymorphs, solvates, enantiomers, stereoisomer, salts, esters, amides, hydrates and any combination thereof.

The present invention relates to a process for preparing solid lipid nanoparticles of curcumin, the process comprising the steps of:

a. dissolving curcumin in a co-solvent for lipid to obtain a solution and maintaining the solution at temperature 10° C. above lipid melting point temperature;
b. adding melted lipid or mixture of lipid selected form group consisting of glycerides and fatty acids to the solution obtained in step (a) to obtain a hot lipid phase;
c. preparing an aqueous surfactant phase comprising water, surfactant and co surfactant and maintaining the aqueous surfactant phase at a temperature 10° C. above lipid melting temperature;
d. adding the hot lipid phase of step (b) to the aqueous surfactant phase of step (c) and mixing at high speed of 4000-15000 rpm for 5-10 min to obtain a primary coarse emulsion; and
e. subjecting the primary coarse emulsion of step (d) to two to six cycles of homogenization at 500 to 1200 bars to obtain solid lipid nanoparticles of curcumin.

In the process as described herein, the co-solvent for lipid having very high affinity to the aqueous phase will move towards the aqueous phase and curcumin will be effectively encapsulated in lipid core.

In a preferred embodiment of the process, the mixture of the hot lipid phase of step (b) and the aqueous surfactant phase of step (c) is homogenized at 8000 rpm for 8 min to obtain a primary coarse emulsion. The primary coarse emulsion is then subjected to three cycles of homogenization at 1000 barsto obtain solid lipid nanoparticles of curcumin.

In one embodiment of the present invention, the co-solvent for lipid is selected from polyethylene glycol, PVP, PVA, glycerol, transcutol, labrafac, gelucire, hydrogenated vegetable glycerides, glyceryl citrate/lactate/lincolate/oleate, polyglyceryl-4-cocoate, polyglyceryl-3-carprate and capoylate and their derivatives, polypropylene glycol, and propylene glycol.

In a preferred embodiment of the present invention, the co-solvent for lipid is polyethylene glycol.

In one embodiment of the present invention, the glyceride is selected from the group consisting of mono-glycerides, di-glycerides, tri-glycerides or mixtures thereof. In one embodiment, the glyceride is selected from the group consisting of glyceryl behenate, tricaprin, trilaurin, trimyristin, tripalmitin, tristearin, 1,2-dioctanoyl-sn-glycerol, 1,2-didecanoyl-sn-glycerol, 1,2-dilauroyl-sn-glycerol, 1,2-dimyristoyl-sn-glycerol, 1,2-dipalmitoyl-sn-glycerol, 1-palmitoyl-2-oleoyl-sn-glycerol, 1-stearoy 1-2-linoleoyl-sn-glycerol, 1-stearoyl-2-arachidonoyl-sn-glycerol, 1-stearoyl-2-docosahexaenoyl-sn-glycerol, 1-oleoyl-2-acetyl-sn-glycerol, 1,2-di-O-phytanyl-sn-glycerol, 1,2-dipalmitoyl ethylene glycol, 1-2-dioleoyl ethylene glycol, glyceryl monostearate, behenoyl polyoxyl-8 glycerides, glyceryl palmitostearate, 1-O-hexadecyl-sn-glycerol, 1-O-hexadecyl-2-acetyl-sn-glycerol, 1-O-hexadecyl-2-O-methyl-sn-glycerol, 1,2-diacyl-3-O-(α-D-glucopyranosyl)-sn-glycerol, stearoyl macrogol-32 glycerides, stearoyl polyoxyl-32 glycerides, lauroyl macrogol-32 glycerides, lauroyl polyoxyl-32 glycerides, lauroyl macrogol-6 glycerides, lauroyl polyoxyl-6 glycerides, oleoyl macrogol-6 glycerides, oleoyl polyoxyl-6 glycerides, linoleoyl macrogol-6 glycerides, polyglyceryl-3 dioleate, glycerol monolinoleate, glyceryl monolinoleate, glycerol monooleates, diethylene glycol monoethyl ether, glyceryl dibehenate, glycerol distearate, glyceryl distearate, glyceryl dipalmitostearate, linoleoyl polyoxyl-6 glyceride, behenyl alcohol, cetyl alcohol, and potassium cetyl alcohol. In a preferred embodiment, the glyceride is glyceryl behenate.

In one embodiment of the present invention, the fatty acid is selected from the group consisting of saturated C4-C28 fatty acids and unsaturated C4-C28 fatty acids. In one embodiment of the present invention, the fatty acid is stearic acid.

In one embodiment of the present invention, the surfactant is selected from the group consisting of ethylene oxide copolymers, propylene oxide copolymers, poloxamers, sorbitan ethylene oxide/propylene oxide copolymers, polysorbate 20, polysorbate 60, polysorbate 80, sorbitan esters, span 20, span 40, span 60, span 80, alkyllaryl polyether alcohol polymers, tyloxapol, bile salts, cholate, glycocholate, taurocholate, taurodeoxycholate, gemini surfactants, alcohols, diethylene glycol monoethyl ether, propanediol, capryl glucoside, decy glucoside, kolliwax or mixtures thereof. In a preferred embodiment of the present invention, the surfactant is polysorbate 80.

In one embodiment of the present invention, the co-surfactant is selected from the group consisting of soy lecithin, egg lecithin, phosphatidylcholine, cholate, glycocholate, taurocholate, taurodeoxycholate, or mixtures thereof. In a preferred embodiment of the present invention, the co-surfactant is soy lecithin.

In one embodiment, the curcumin is added to a co-solvent for lipid in an amount in the range of 0.6 to 1.5% w/w of the solid lipid nanoparticle. In a preferred embodiment, the curcumin is added to a co-solvent for lipid in an amount of 0.6% w/w of the solid lipid nanoparticle. In a preferred embodiment, the curcumin is added to a co-solvent for lipid in an amount of 1.5% w/w of the solid lipid nanoparticle. In one embodiment, the amount of co-solvent in the solid lipid nanoparticle formulation is 5% to 8% w/w, preferably 8%. In one embodiment, the lipid or the lipid mixture is in the range of 4%-10% w/w of the solid lipid nanoparticle. In one embodiment, the surfactant is in the range of 8% to 12% w/w, preferably 12% w/w of the solid lipid nanoparticle. In one embodiment, the co-surfactant is in the range of 0.4% w/w of the solid lipid nanoparticle.

The amounts of the components are not limiting and only representative of particular embodiments. The amounts of the components will change with increase or decrease of surfactant and lipid concentration. SLNs will not form below a specific concentration of the surfactant and lipid.

The selection of the components was made to complement the activity of curcumin viz. polyethtlene glycol acts as a co-solvent penetrating enhancer, plasticizer, muco-penetrating agent and osmotic agent, polysorbates are surfactant and also effective Pgp efflux inhibitors thus improving absorption/permeation and bioavailability of curcumin and phospholipid as a surfactant and antioxidant.

The present invention provides polyethylene glycol as a cosolvent to dissolve curcumin in lipidic phase considering following characteristics:

1) High solubility of curcumin in PEG 600 results in solubilisation of curcumin in lipidic phase resulting in high drug loading.
2) High hydrophilicity of PEG 600 drives it out of curcumin lipidic phase into aqueous phase precipitating curcumin, which being lipophillic is encapsulated within the lipidic globule resulting in high entrapment.

Further, any curcumin which is carried by PEG 600 into the aqueous phase is also in the dissolved/amorphous state because of the specific composition of the aqueous phase.

Hence, whole system (lipidic phase as well as aqueous phase) will result in solubilisation of curcumin in aqueous phase.

The process as defined in the present invention results in a curcumin content in the solid lipid nanoparticles is high and in the range of 0.5 to 10% w/v of the aqueous SLN dispersion and upto 50% w/w with respect to the lipid matrix. In one embodiment, curcumin content in the solid lipid nanoparticles is in the range of 0.5 to 2.5% w/v of the aqueous SLN dispersion. The entrapment efficiency of curcumin in the solid lipid nanoparticles is in the range of 50-100% by weight of curcumin added.

The present invention also relates to solid lipid nanoparticles of curcumin as prepared by the process defined herein.

The solid lipid nanoparticles of curcumin comprise a. a lipid phase comprising mixture of lipid selected from group consisting of glycerides and fatty acids, and a co-solvent;
b. an aqueous phase comprising water, surfactant and co surfactant, wherein curcumin is entrapped in lipid phase and is present in a solubilised form in the aqueous phase.

The solid lipid nanoparticles of curcumin have a particle size in the range of 20 to 800 nm. Preferably, the particle size is in the range of 170-250 nm. The solid lipid nanoparticles of curcumin prepared by the process of the present invention have a uniform particle size distribution.

The solid lipid nanoparticles of curcumin as prepared by the process of the present invention have a spherical, ellipsoid, oblong, anisotropic and rod shape.

The SLNs of curcumin have an antimicrobial, antioxidant, anti-inflammatory, analgesic, anti-ageing, neurotonic, memory enhancing effect, health tonic, anticancer, wound healing, anti sepsis, anti-depressant, obsessive compulsive disorder, cardiotonic, hepatoprotective, immunomodulator, antacid, antiulcer, effectiveness for the treatment of Inflammatory bowel disease, crohn's disease, irritable bowel syndrome, skin whitening, skin brightening, anti-hyperpigmentation anti-wrinkle effect, anti blemish, anti acne, activity against metabolic disorders including diabetes and obesity, and use in the management of dental disorders including gingivitis, periodentitis and general hygieneand use in rheumatoid arthritis. Further, SLNs exhibit any property that is exhibited by free curcumin.

The SLNs of curcumin also show high permeation. The solid lipid nanoparticles prepared by the process of the present invention therefore can be used for efficient drug delivery. The SLNs of curcumin are in the form of a dispersion for oral, parenteral, ocular, intranasal, vaginal, rectal, otic, transdermal and topical delivery.

The solid lipid nanoparticles of curcumin are non-toxic in nature. When introduced in a living system for example a rat, the nanoparticles do not have any effect on the body weight, feed and water consumption or behavioural pattern for about a month. The solid lipid nanoparticles of curcumin can be given in the doses of 500 to 1 mg/kg by weight of the body. $LD_{50}$ of the dispersion was found to be more than 2000 mg/kg weight of the body.

In one embodiment, the solid lipid nanoparticles of curcumin are in the form of a dispersion. In another embodiment, the solid lipid nanoparticles are combined with a carbopol gel to be in the form of a hydrogel. In yet another embodiment, the solid lipid nanoparticles of curcumin are combined with clays viz. bentonite, kaolin, pink clay, french clay, fullers earth and rhassoul clay and titanium dioxide. In a preferred embodiment, the solid lipid nanoparticles of curcumin are in the form of a dispersion.

In one embodiment, the SLNs of curcumin are combined with a suitable excipient to result in gel, hydrogel, organogel, syrup, paste, cream, facewash, mouthwash, oral rinse, ointment, liquid ampoule, dispersion, aerosol spray, powder, orthotic aid, liquid oral, facemask, film, implant, tablet, lozenges, capsules, suppositories, pessaries, patch and gummies.

The SLNs as obtained by the process of the present invention are autoclavable and water washable.

In one embodiment, the solid lipid nanoparticles of curcumin increase the relative bioavailability of curcumin by 5 to 250 times. In another embodiment, the solid lipid nanoparticles of curcumin increase the relative bioavailability of curcumin by 41 times.

In another embodiment, the solid lipid nanoparticles of curcumin may be spray dried or lyophilised. The SLNs are lyophilised using 2 to 25% of mannitol, trehalose, sucrose, lactose or lactulose.

The lyophilised solid lipid nanoparticles of curcumin can be used directly or suitably modified to incorporate into tablets, capsules, microsphers, beads, emulsions, gel, hydrogel, organogel, paste, cream, facewash, mouthwash, ointment, liquid oral, facemask, film, implant, tablet, lozenges, capsules, suppositories, pessaries, patch and gummies.

The solid lipid nanoparticles of curcumin show controlled release of curcumin up to 9 days, more specifically 5 days.

The solid lipid nanoparticles of curcumin show photostability and protection to pH degradation at pH 1.2, 6.8, 7.4 and 9 with increase in t1/2 of curcumin by 2 to 20 times, more specifically 4 to 15 times.

Also, solid lipid nanoparticles of curcumin show stability at room temperature up to 6 months and under refrigeration for more than one year.

The present process achieved high loading of curcumin (15% with respect to the lipid phase: high concentration >5 mg/ml of curcumin in the aqueous SLN dispersion whereas aqueous solubility of curcumin is 0.6 microg/ml), significant entrapment efficiency (77%), and small size (average particle size 248 nm: PDI-0.161). Resulting formulation was nanosized (100-300 nm), with uniform particle size distribution (Polydispersity index≤0.3) and a capacity for solubilisation, high permeation across biological membranes, photoprotection and protection against degradation at alkaline and physiological pH, of curcumin, thereby increasing its oral and topical bioavailibility. The lipid core provides protection to curcumin against oxidation, and hydrolytic and photo-degradation in addition to providing curcumin in a bioavailable and controlled manner. Biocompatible, cheap, FDA approved easily available components including a lipid, non-ionic surfactants and surfactant supporting agents/co-solvents have been used. The efficient entrapment of curcumin within the core of these nanoparticles in a solubilised form increases its efficacy. The formulation is an aqueous dispersion of curcumin which is water soluble and washable.

The Advantages of the Present Invention Include:

1. Method of preparation ensures that curcumin is stabilised.
2. High entrapment efficiency>70%
3. High solubilization of curcumin (10,000 times)
4. Water soluble and washable system
5. High drug loading (15%)
6. Method is easy, scalable, and commercially viable and uses equipment such as homogenizer which are normally present in any pharmaceutical industry.
7. All the employed components are GRAS.
9. Process is suitable for effective delivery via oral and topical route, including mucosal application and in cosmetics

EXAMPLES

The curcumin used in the present invention is procured from Sunpure Extracts Pvt. Ltd.

1. Preparation of Curcumin Loaded Solid-Lipid Nanoparticles (SLNs)

A. Preparation of Curcumin Loaded Solid Lipid Nanoparticles (C-SLNs) with 0.6% w/w Curcumin Solid lipid nanoparticles of Curcumin were prepared by hot homogenization method. 0.6% w/w curcumin was dissolved in 8% PEG 600 followed by addition of molten 4% w/w Compritol® 888 ATO (glyceryl behenate). Then a primary crude emulsion was prepared by emulsifying hot lipid phase containing 0.6% curcumin, 4% Compritol® 888 ATO and 8% PEG 600 in the aqueous surfactant phase containing 12% Tween 80 and 0.4% Phospholipon 90 G (soya lecithin) maintained at a temperature above melting point of Compritol® 888 ATO (70° C. to 75° C.) using high-speed stirrer (WiseTis HD 15D, Germany) at 8,000 rpm for 8 min. The dispersion was then subjected to high pressure homogenization (HPH) using Emulsiflex C3 Avestin (Canada) homogenizer at 1000 bars and three cycles. The dispersion thus obtained was allowed to cool to room temperature, forming lipid nanoparticles by re-crystallization of the hot dispersed lipid.

COMPARATIVE EXAMPLE

Independent Variables and their Highest and Lowest Concentrations

A number of formulations with 0.6% w/w/of curcumin using fixed amount of lipid and phosholipon 90G and with varying type and concentration of surfactants were prepared by above procedure (Table 1). The formulations were observed for stability (no separation of phases), drug expulsion and crystallisation.

TABLE 1

Various formulations prepared with varying type and concentration of surfactants

| S No | Surfactant Type A | B | C | D | Drug (%) | Manual observation |
|---|---|---|---|---|---|---|
| F1 | 8.9 | — | — | — | 0.6 | Settling of drug on keeping overnight. Crystals seen in microscope |
| F2 | 8.9 | 5 | — | — | 0.6 | Settling of drug on keeping overnight. Crystals seen in microscope |
| F3 | 8.9 | 8 | — | — | 0.6 | No settling of drugs. Crystals seen under microscope |
| F4 | 8.9 | — | 5 | — | 0.6 | Settling |
| F5 | 8.9 | — | 8 | — | 0.6 | No settling of drugs. Crystals seen under microscope. Gelucire expelled out |
| F6 | 8.9 | 5 | 5 | — | 0.6 | No settling of drugs. Crystals seen under microscope. Gelucire expelled out |

TABLE 1-continued

Various formulations prepared with varying type and concentration of surfactants

| | Surfactant Type | | | | Drug | |
| S No | A | B | C | D | (%) | Manual observation |
| --- | --- | --- | --- | --- | --- | --- |
| F7 | 8.9 | 5 | 8 | — | 0.6 | No settling of drugs. Crystals seen under microscope. Gelucire expelled out |
| F8 | 8.9 | — | — | 5 | 0.6 | Settling |
| F9 | 8.9 | — | — | 8 | 0.6 | Settling |
| F10 | 8.9 | 5 | | 8 | 0.6 | Crystals observed under microscope |
| F11 | 8.9 | 5 | | 10 | 0.6 | Crystals observed under microscope |
| F12 | 8.9 | 8 | | 10 | 0.6 | No Crystals observed under microscope |
| F13 | 12 | 5 | — | — | 0.6 | Crystals observed under microscope |
| F14 | 12 | 8 | — | — | 0.6 | Crystals observed under microscope |
| F15 | 12 | — | — | 5 | 0.6 | Crystals observed under microscope |
| F16 | 12 | — | — | 8 | 0.6 | No Crystals observed under microscope till 4 weeks |

A = Tween 80,
B = PEG 400,
C = Gelucire14/44,
D = Polyethylene glycol 600 (PEG 600)

Most of the formulations prepared either showed formation of crystals or settling of the drug. F12 did not show any drug crystals but the total concentration of surfactant used was very high (26.9%). Only, F16 (present formulation) did not show drug crystal formation for 4 weeks and also used less surfactant and only two surfactants, Tween 80 and PEG 600.

Significant Factors

A number of formulation and processing variables influence the overall performance of nanoparticles. Taguchi design was employed for seven factors at two levels each as given in Table 2 to study the effect of each variable and interaction among them through the conventional approach.

TABLE 2

Designed formulations for the evaluation of curcumin loaded solid lipid nanoparticles using Taguchi design

| Sr. No. | Stirring speed (rpm) | Stirring time (min) | No. of cycle | Tween 80 (% w/w) | Peg 600 (% w/w) | Lipid (% w/w) | Phospholipon 90G (% w/w) | Particle size (nm) | Entrapment efficiency (%) | PDI |
| --- | --- | --- | --- | --- | --- | --- | --- | --- | --- | --- |
| 1 | 6000 | 5 | 3 | 8 | 5 | 3 | 0.4 | 694.1 | 45.6 | 0.256 |
| 2 | 6000 | 5 | 3 | 12 | 8 | 5 | 1 | 349.9 | 76.8 | 0.132 |
| 3 | 6000 | 10 | 6 | 8 | 5 | 5 | 1 | 501.9 | 50.6 | 0.275 |
| 4 | 6000 | 10 | 6 | 12 | 8 | 3 | 0.4 | 138.4 | 74.1 | 0.109 |
| 5 | 10000 | 5 | 6 | 8 | 8 | 3 | 1 | 378.3 | 60.2 | 0.186 |
| 6 | 10000 | 5 | 6 | 12 | 5 | 5 | 0.4 | 214.5 | 63.7 | 0.140 |
| 7 | 10000 | 10 | 3 | 8 | 8 | 5 | 0.4 | 416 | 64.8 | 0.218 |
| 8 | 10000 | 10 | 3 | 12 | 5 | 3 | 1 | 233.8 | 61.5 | 0.174 |

Figure 1:
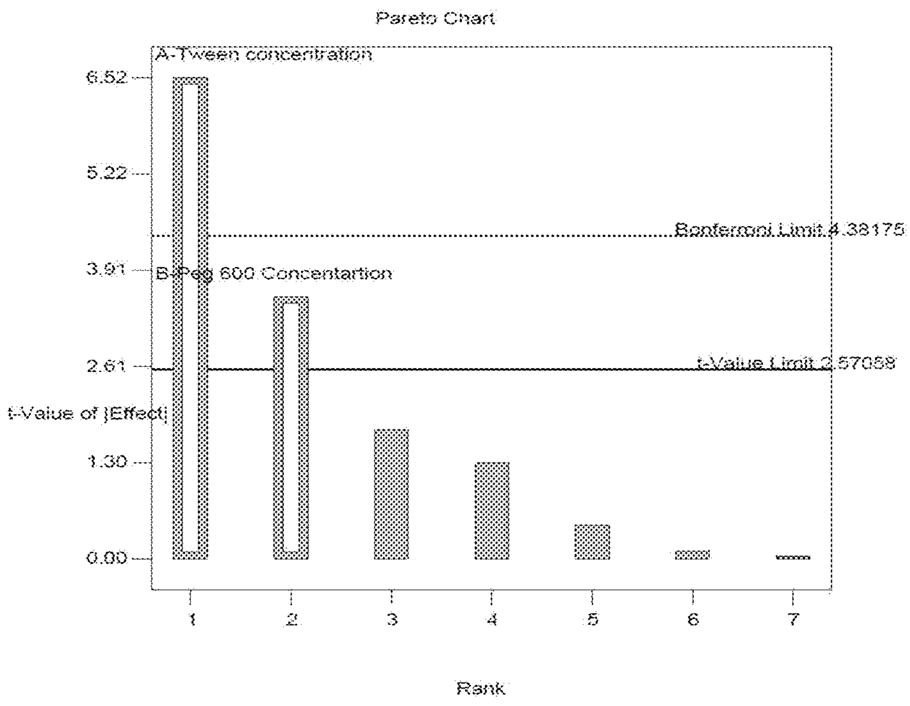
FIG. 1 illustrates Pareto chart for entrapment efficiency.
Figure 2:
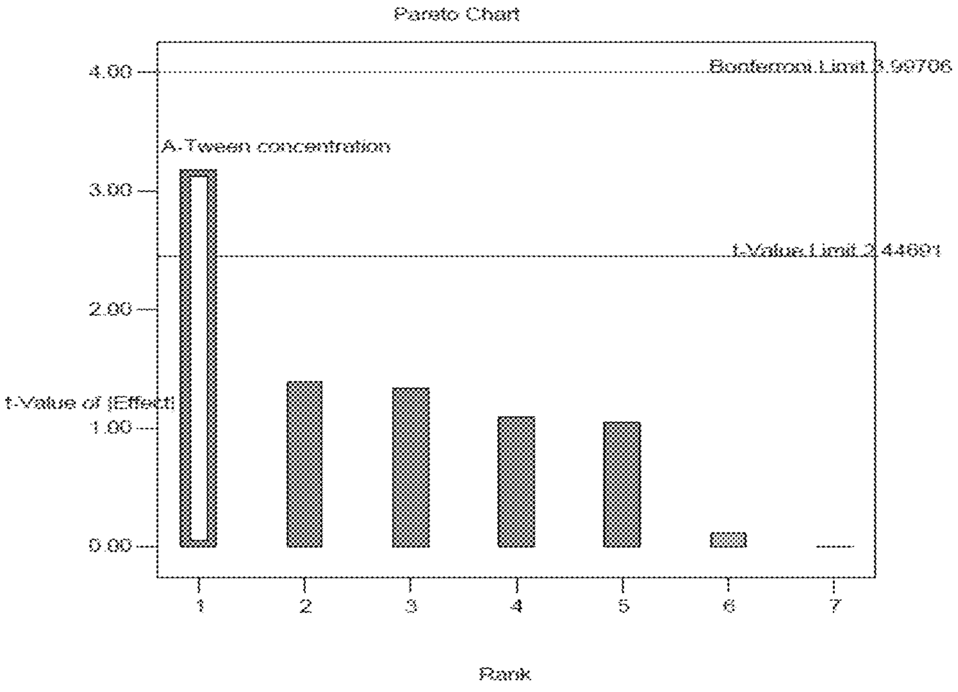
FIG. 2 illustrates Pareto chart for particle size

Each response coefficient was studied for its statistical significance by Pareto charts as shown in FIG. 1, 2, 3. FigureIillustrates Pareto chart for entrapment efficiency, FIG. 2 illustrates Pareto chart for particle size and FIG. 3 illustrates Pareto chart for PDI. Pareto charts establish t value of effect that is studied by two limit lines namely the Bonferroni limit line and t limit line. Coefficients with t value of effect above the Bonferroni line are designated as certainly significant coefficient, coefficients with t value of effect between Bonferroni line and t limit line are termed as coefficients likely to be significant, while t value of effect below the t limit line is statistically insignificant coefficient and should be removed from the analysis. Pareto charts indicates that the effect of Tween 80 is the only significant factor in case of particle size while both Tween 80 and Polyethylene glycol 600 have significant effects in case of entrapment efficiency and PDI.

Similarly following examples were prepared by the same procedure but by changing the concentration of tween 80 and PEG 600 to reach the final formulations Comparative Example 1

Curcumin: 0.6% w/w
Peg 600: 5% w/w
Compritol® 888 ATO (glyceryl behenate): 4% w/w
Tween 80: 8% w/w
Phospholipon 90G (soya lecithin): 0.4% w/w
Particle size: 598 nm
Entrapment efficiency: 45.9%

Comparative Example 2

Curcumin: 0.6% w/w
Peg 600: 8% w/w
Compritol® 888 ATO (glyceryl behenate): 4% w/w
Tween 80: 8% w/w
Phospholipon 90G (soya lecithin): 0.4% w/w
Particle size: 350 nm
Entrapment efficiency: 60.3%

Comparative Example 3

Curcumin: 0.6% w/w
Peg 600:4.37868% w/w
Compritol® 888 ATO (glyceryl behenate): 4% w/w
Tween 80: 10% w/w Phospholipon 90G (soya lecithin): 0.4% w/w
Particle size: 400 nm
Entrapment efficiency: 47.6%

Comparative Example 4

Curcumin: 0.6% w/w
Peg 600:6.5% w/w
Compritol® 888 ATO (glyceryl behenate): 4% w/w
Tween 80:7.17157% w/w
Phospholipon 90G (soya lecithin): 0.4% w/w
Particle size: 559.3 nm
Entrapment efficiency: 49.6%

Comparative Example 5

Curcumin: 0.6% w/w
Peg 600:6.5% w/w
Compritol® 888 ATO (glyceryl behenate): 4% w/w
Tween 80: 10% w/w
Phospholipon 90G (soya lecithin): 0.4% w/w
Particle size: 290 nm
Entrapment efficiency: 67.5%

Comparative Example 6

Curcumin: 0.6% w/w
Peg 600:8.62132% w/w
Compritol® 888 ATO (glyceryl behenate): 4% w/w
Tween 80: 10% w/w
Phospholipon 90G (soya lecithin): 0.4% w/w
Particle size: 200 nm
Entrapment efficiency: 71.9%

Comparative Example 7

Curcumin: 0.6% w/w
Peg 600: 5% w/w
Compritol® 888 ATO (glyceryl behenate): 4% w/w
Tween 80: 12% w/w
Phospholipon 90G (soya lecithin): 0.4% w/w
Particle size: 220.3 nm
Entrapment efficiency: 69.5%

Comparative Example 8

Curcumin: 0.6% w/w
Peg 600:6.5% w/w
Compritol® 888 ATO (glyceryl behenate): 4% w/w
Tween 80:12.8284% w/w
Phospholipon 90G (soya lecithin): 0.4% w/w
Particle size: 190 nm
Entrapment efficiency: 73.9%

The comparative examples indicate that this system is highly influenced by the concentration of Tween 80 and PEG 600 which resulted in high entrapment efficiency and small particle sizes for the preparation of SLN.

It is seen that on increasing the amount of Tween 80 and PEG 600 in the formulation decreased the particle size. Similarly, increasing Tween 80 and PEG 600 concentration in the formulation increased entrapment efficiency.

B. Preparation of Curcumin Loaded Solid Lipid Nanoparticles (C-SLNs) with 1.5% w/w Curcumin Curcumin SLNs were prepared using high pressure hot homogenization technique. Aqueous phase was prepared by adding tween 80, phospholipon 90 G and water in a beaker and heated to around 80° C. Lipid (8% w/w of Compritol 888 ATORand 2% w/w/of Glyceryl monostearate (GMS) was melted at 70-75° C. and curcumin, dissolved in polyethylene glycol 600 was added to it. The obtained lipid mix was added to the aqueous phase under high speed homogenization (8000 rpm for 8 minutes) to obtain a coarse emulsion. The emulsion was then passed through high pressure homogenizer (3 cycles) and the SLNs were formed by cooling the obtained dispersion to room temperature.

COMPARATIVE EXAMPLES

Various formulations, starting with a C-SLNs (with 6 mg curcumin per ml) incorporating 10-15 mg (1-1.5%) of curcumin per ml of SLN dispersion were prepared, as described in part A. Most of these SLN systems however showed settling of curcumin crystals at the bottom of the SLN formulation within 24 h of preparation.

Compritol 888 ATOR was combined with Glyceryl monostearate (GMS) (lipid mixture) in different ratios to prepare C-SLN formulation and the prepared formulations were observed for settling of curcumin (table 3). It has been reported that curcumin showed maximum solubility in GMS when a panel of lipids were evaluated (Shrotriya et al., 2018). Formulations with combination of GMS with Compritol 888 ATOR is shown in Table 4 and their respective TDC, entrapment efficiency, particle size and PDI are shown in Table 4

TABLE 3

Formulation development of C-SLNs using lipid mixture

| Formulation Code | Compritol 888 ATO ® (%) | GMS (%) | Tween 80 (%) | PEG 600 (%) | Phospholipon 90 G (%) | Curcumin (%) | Drug Settling |
|---|---|---|---|---|---|---|---|
| F8 | 3 | 3 | 12 | 8 | 0.4 | 1.5 | x |
| F9 | 4 | 2 | 12 | 8 | 0.4 | 1.5 | x |
| F10 | 6 | 2 | 12 | 8 | 0.4 | 1.5 | x |
| F11 | 8 | 2 | 12 | 8 | 0.4 | 1 | x |
| F12 | 8 | 2 | 12 | 8 | 0.4 | 1.2 | x |
| F13 | 8 | 2 | 12 | 8 | 0.4 | 1.5 | x |

TABLE 4

Characterization of C-SLNformulations

| Formulation code | Particle size (nm) | PDI | TDC (mg/ml) | Entrapment efficiency(%) |
|---|---|---|---|---|
| F8 | 975.2 | 0.376 | 13.87 | 82.29 |
| F9 | 556.5 | 0.315 | 13.78 | 84.83 |
| F10 | 598.2 | 0.373 | 13.83 | 87.76 |
| F11 | 473.5 | 0.087 | 9.29 | 82.13 |

TABLE 4-continued

| Characterization of C-SLNformulations | | | | |
|---|---|---|---|---|
| Formulation code | Particle size (nm) | PDI | TDC (mg/ml) | Entrapment efficiency(%) |
| F12 | 564.1 | 0.354 | 11.4 | 85.6 |
| F13 | 538.8 | 0.369 | 14.35 | 82.9 |

Formulations (F8-F10) showed presence of curcumin crystals when observed under light microscope, indicating that drug is present in undissolved/undispersed form. The remaining three formulations (F11, F12 and F13) showed no drug settling or formation of crystals. However, F13 (present invention) showed highest drug loading (~15 mg/ml).

C. Preparation of curcumin loaded solid lipid nanoparticles (C-SLNs) with 2.5% w/v, 5% w/v and 10% w/v of curcumin Similar to the previous examples curcumin loaded solid lipid nanoparticles (C-SLNs) with 2.5% w/v, 5% w/v and 10% w/v of curcumin. The curcumin loaded solid lipid nanoparticles showed the properties as follows:

Curcumin: 2.5% w/v
Tween 80: 12% w/v
Polyethylene glycol 600: 8% w/v
Compritol 888 ATO: 8% w/v
Glyceryl monostearate: 2% w/v
Phospholipon 90 G: 0.4% w/v
Polaxamer 188: 1% w/w
Particle size: 289.2 nm
Entrapment efficiency: 78%
Curcumin: 5% w/v
Tween 80: 12% w/v
Polyethylene glycol 600: 8% w/v
Compritol 888 ATO: 8% w/v
Glyceryl monostearate: 2% w/v
Phospholipon 90 G: 0.4% w/v
Polaxamer 188: 1% w/w
Particle size: 275 nm
Entrapment efficiency: 78%
Curcumin: 10% w/v
Tween 80: 12% w/v
Polyethylene glycol 600: 8% w/v
Compritol 888 ATO: 8% w/v
Glyceryl monostearate: 2% w/v
Phospholipon 90 G: 0.4% w/v
Polaxamer 188: 1% w/w
Particle size: 298.5 nm
Entrapment efficiency: 76%

2. Characterization of Prepared Solid Lipid Nanoparticles

Total Drug Content (TDC)

SLN dispersion was treated with a mixture of chloroform: methanol (1:1). Chloroform helps to dissolve the lipid matrix and disrupt formed SLNs. Absorbance of the obtained solution was determined spectrophotometrically at 427 nm to confirm TDC. A >90% TDC ensures efficient production process with minimal losses.

A total drug content of 5.8±0.2 mg/ml was observed. High values approaching 100% of TDC confirm that insignificant losses occurred during the process of preparation of SLNs by high-pressure homogenization (n=6).

Entrapment Efficiency (EE)

EE was determined by dialyzing ATS-SLN dispersion in a dialysis bag (7k Da MW cut off) immersed in 100 ml methanol, stirred magnetically (100 rpm). After 30 min SLNs was removed from the bag, disrupted with suitable quantity of chloroform:methanol (1:1). Entrapment efficiency was determined spectrophotometrically as:

$$\frac{\text{Amount of drug } \textit{remainig} \text{ in the bag}}{\text{Total } \textit{amaount} \text{ loaded}} \times 1000 \times 10$$

An entrapment efficiency of 75.55±2.31% was observed.

Particle Size and PDI

Mean diameter of SLNs in the dispersion (10× dilution) and PDI was determined using laser diffraction (Beckman Coulter, Delsa™ Nano C, Switzerland).

A particle size of 170.1±26.6 nm and PDI of 0.143±0.026 was observed (FIG. 4)

Zeta Potential

The zeta potential of the prepared formulation (10× dilution) was measured by (Beckman Coulter, Delsa™ Nano C, Switzerland) using a flow cell.

The zeta potential of the prepared formulation was found to be9.67±1.47 (n=6) as shown in FIG. 5

Field Emission Scanning Electron Microscopy (FESEM)

C-SLNs were observed microscopically using FESEM (H-7500, Hitachi Ltd., Japan) for uniformity of size, shape and physical stability characteristic i.e. aggregation or irregularity. FESEM has narrower probing beams at low and high electron energy, so it provides improved spatial resolution while minimizing sample damage. It provides topographical information at magnifications of 250-1,000,000× with ion-free images. The drop of the sample appropriately diluted (10 times) was placed on a carbon-coated cooper grid to leave a thin film on the grid. Excess of the solution was drained off with a filter paper. The grid was air dried thoroughly and samples were viewed under FESEM.

The FESEM of the C-SLN (figure6) formulation showed that particles are nearly spherical in shape and were present as individual entities rather than agglomerates confirming their stability. A coat of surfactant on the outside of SLN covering the entire surface of the particle uniformly is clearly visible in the figure. The coat of surfactant will assign it with stability to aggregation.

Powder X-Ray Diffraction (PXRD)

The crystalline/amorphous nature of formulated nanoparticles was confirmed by X-ray diffraction measurements carried out with an X-ray diffractometer. PXRD studies were performed by exposing the samples to $CuK_\alpha$ radiation (45 kV, 40 mA) and scanning from 5° to 50°, 2θ at a step size of 0.017° and scan step time of 25 second. The instrument measures interlayer spacing d which is calculated from the scattering angle θ, using Bragg's equation $n\lambda=2d \sin 0$, where is the wavelength of the incident X-ray beam and n is the order of the interference. SLNs were lyophilized prior to analysis. Obtained PXRD patterns were compared with the characteristic drug peak intensity obtained for the pure drug.

PXRD pattern of curcumin and C-SLNs are shown in FIG. 7, PXRD pattern of curcumin exhibited sharp peaks at 20 scattered angles of 10.64, 18.79, 23.43 and 29.51 indicating its crystalline nature. In case of lyophilised C-SLNs, all these characteristic peaks are missing, indicating that curcumin is present in a soluble and thus amorphous form in a lipid enclosure of SLNs.

Differential Scanning Calorimeter (DSC)

DSC was performed with a Q20 Differential scanning calorimeter (TA system, USA). DSC is a tool to investigate the melting and recrystallization behaviour of crystalline materials like the lipid and the other component including drug of the presently prepared SLNs. The breakdown or fusion of the lipid crystal lattice by heating or cooling the samples yields information about the internal polymorphisms, crystal ordering or glass transition process (Uner, 2006). It uses the fact that different lipid modifications have different melting points and enthalpies. The thermal analysis of curcumin, physical mixture of the components and C-SLNs was done to observe any significant changes in the pattern of the peaks (Orecchioni et al., 2003: Reddy and Venkateshwarlu, 2004b). Samples were placed in conventional aluminium pan and heated from 10° C. to 250° C. at a scan speed of 10° C./min. Liquid samples were placed in special hermetic pans.

DSC is a thermoanalytical technique in which the differences in the amount of heat required to maintain the sample and reference at same temperature is measured as a function of temperature and time as shown in FIG. 8. In case of pure curcumin (FIG. 8*b*), a melting endotherm appeared at 178.19° C. corresponding to its melting point at 180-183° C. The C-SLNs however show a broad endotherm starting from almost 78° C.-116° C. with a peak at 1.15° C. (FIG. 8*a*). Another sharp peak was also observed at 117.72° C. Broadening of peaks indicate amorphous nature of C-SLNs while shift to a lower temperature indicates a nano nature. The peak corresponding to Compritol®888 ATO at 73.11° C. (FIG. 8*c*) is not observed C-SLNs. Thismeans significant or complete loss of its crystal lattice so as to generate significant spaces for efficient encapsulation (~ 80%) of curcumin within the lipid matrix.

Fourier Transform Infra Red (FTIR)

FTIR spectra of pure curcumin, lipid and curcumin SLNs were recorded using KBr pellet technique on an IR spectrophotometer over a range 4000-400 cm-1. The peaks obtained with free drug and the C-SLN formulation were compared for any significant changes.

The IR peaks obtained with the developed formulation of C-SLNs (FIG. 9) reveal an intermolecular stretching of the—OH groups (3400-3200 cm-1) of curcumin when compared with the peaks of free curcumin and the lipid. In case of pure drug, a broad peak at 3293 cm-1 and the sharp one at 3508 cm-1 indicate the presence of—OH group. This may be regarded as direct indication of the formation of SLNs as the stretching could not be observed in case of curcumin or Compritol® 888 ATO.

Autoclavability

The prepared formulation was autoclaved at 120° C. for 15 mins and observed for any change in total drug content, entrapment efficiency, particle size, PDI and zeta potential.

The developed C-SLNs were found to be stable on autoclaving with no change in entrapment efficiency. Slight increase in particle size was observed as given in table 5.

TABLE 5

Parameters before and after autoclaving (n = 6)

| Autoclaving | TDC (mg/ml) | Entrapment efficiency (%) | Particle size (nm) | PDI | Zeta potential |
|---|---|---|---|---|---|
| Before | 5.8 ± 0.2 | 75.55 ± 2.31 | 170.1 ± 26.6 | 0.143 ± 0.026 | −9.67 ± 1.47 |
| After | 5.7 ± 0.3 | 74.24 ± 3.6 | 253.7 ± 28.0 | 0.182 ± 0.032 | −9.50 ± 1.86 |

Degradation Studies of C-SLN

The hydrolytic stability of C-SLN and free curcumin was investigated at pH 1.2, phosphate buffer pH 6.8, phosphate buffer pH 7.4 and alkaline borate buffer pH 9 (I.P., 2014). The stock solution of free curcumin (100 μg/ml) was prepared in methanol by dissolving 5 mg of curcumin in 50 ml of methanol. It was further diluted to 5 μg/ml with respective buffers (pH 1.2, pH 6.8, pH 7.4 and pH 9). In case of C-$SLN_{aq}$, Iml dispersion was placed in a dialysis bag and dialyzed against methanol (100 ml) at room temperature for 45 minutes to remove unentrapped drug. Total drug content of the dialysed C-SLNs was determined and diluted suitably to prepare a 100 μg/ml of stock which was diluted further to 5 μg/ml with respective buffers. The stock solution and sample solution were prepared in amber coloured volumetric flasks to avoid photodegradation. The solutions were prepared and incubated at 37° C. The samples were withdrawn at varying times, viz. 0, 0.5, 1, 2, 4, 6, 8, 10, 12 and 24 h. Initially the samples were analysed spectrofluorimetry at 425 nm as excitation Amax and 535 nm as emission Amax but curcumin exhibits weak fluorescence in aqueous systems. Presence of water quenches the fluorescent intensity of curcumin. The samples were thus analysed subsequently using the UV/Visible spectrophotometer at $\lambda_{max}$425 nm. The absorbance read at zero time was considered as 100% and change in concentration and % degradation was determined accordingly.

The graph between concentration versus time, log concentration versus time and percent drug remaining versus time were plotted. The degradation constant (k) for the first order was calculated by multiplying the slope of log concentration versus time plot with 2.303.

The aim of the study was to investigate if encapsulation of curcumin within SLNs provides protection against hydrolytic degradation. Data from free curcumin was compared with those for C-SLNs (Table 6, FIG. 10). The samples were initially analysed by spectrofluorimetry at 425 nm as excitation Amax and 535 nm as emission Amax but there was a quenching in the intensity of curcumin in the aqueous system. It has been documented that curcumin has weak fluorescence in aqueous solutions which can be enhanced by increasing the concentration of apolar solvents (Began et al., 1999). It has been observed that the presence of more than 0.01% (v/v) water in the curcumin-acetone solution increases its emission Amax from 504 to 520 nm, and causes quenching which increases with the increase in water content. Water has however no effect on excitation Amax (Jasim and Ali, 1992).

TABLE 6

| Percentage remaining of free curcumin and C-SLNs with time at various pH (n = 6) | | | | | | | | |
|---|---|---|---|---|---|---|---|---|
| Time | pH 1.2 | | pH 6.8 | | pH 7.4 | | pH 9 | |
| (h) | F. Cur | C-SLNs | F. Cur | C-SLNs | F. Cur | C-SLNs | F. Cur | C-SLNs |
| 0 | 100.00 ± 0.06 | 100.00 ± 0.03 | 100.00 ± 0.04 | 100.00 ± 0.06 | 100.0 ± 0.060 | 100.00 ± 0.06 | 100.00 ± 0.004 | 100.00 ± 0.03 |
| 0.08 | 89.23 ± 0.02 | 99.49 ± 0.04 | 94.93 ± 0.06 | 99.80 ± 0.01 | 96.33 ± 0.02 | 99.49 ± 0.05 | 82.59 ± 0.009 | 90.45 ± 0.004 |
| 0.25 | 88.29 ± 0.01 | 98.87 ± 0.03 | 87.63 ± 0.04 | 99.49 ± 0.02 | 93.81 ± 0.04 | 98.87 ± 0.04 | 61.43 ± 0.004 | 72.87 ± 0.006 |
| 0.5 | 85.60 ± 0.01 | 98.25 ± 0.03 | 81.95 ± 0.08 | 98.08 ± 0.02 | 84.17 ± 0.04 | 98.25 ± 0.07 | 32.76 ± 0.006 | 58.39 ± 0.006 |
| 1 | 87.24 ± 0.001 | 97.12 ± 0.03 | 79.72 ± 0.06 | 97.06 ± 0.01 | 75.92 ± 0.04 | 95.07 ± 0.07 | 20.48 ± 0.001 | 40.13 ± 0.003 |
| 2 | 72.37 ± 0.02 | 96.20 ± 0.03 | 66.73 ± 0.05 | 93.22 ± 0.03 | 67.20 ± 0.03 | 92.60 ± 0.06 | 15.70 ± 0.002 | 21.66 ± 0.005 |
| 3 | 68.74 ± 0.03 | 95.79 ± 0.03 | 62.68 ± 0.07 | 92.21 ± 0.03 | 61.01 ± 0.03 | 92.29 ± 0.05 | 9.90 ± 0.003 | 19.53 ± 0.005 |
| 4 | 62.76 ± 0.01 | 94.35 ± 0.03 | 57.81 ± 0.05 | 90.79 ± 0.02 | 49.08 ± 0.04 | 85.51 ± 0.07 | 2.39 ± 0.004 | 17.41 ± 0.006 |
| 5 | 61.01 ± 0.01 | 93.11 ± 0.03 | 43.61 ± 0.08 | 89.37 ± 0.03 | 40.60 ± 0.03 | 82.32 ± 0.06 | — | 11.46 ± 0.003 |
| 6 | 53.40 ± 0.02 | 92.39 ± 0.04 | 23.12 ± 0.04 | 89.07 ± 0.02 | 24.31 ± 0.01 | 81.50 ± 0.05 | — | 2.76 ± 0.006 |
| 24 | 15.76 ± 0.01 | 79.86 ± 0.08 | 11.36 ± 0.04 | 71.56 ± 0.02 | 13.99 ± 0.01 | 66.08 ± 0.05 | — | — |

From the data, it has been observed that at acidic pH 1.2, C-SLNs did not show any significant degradation (approximately 8%) upto 6 h ($p<0.05$). However almost 20% of curcumin entrapped within the SLNs degraded at 24 h ($P<0.001$). In contrast, a degradation of upto 50% and 85% is observed in 6 and 24 h, respectively for free curcumin. At pH 6.8, 77% free curcumin degraded within 6 h and 89% degraded within 24 h whereas in case of entrapped drug (C-SLNs), only a 10% degradation upto 6 h and 30% degradation upto 24h was observed. Similarly, at physiological pH 7.4, significant amount (75%) of free curcumin degraded within 6 h and 77% degraded in 24 h and at extreme pH 9, free curcumin showed approximately 98% degradation at 4 h while the same amount of curcumin degraded at 6 h. The presented data demonstrate that SLNs significantly protect the encapsulated curcumin against hydrolytic degradation (figure10: red for C-SLNs and blue for free-cur).

The degradation kinetics of curcumin under various pH conditions and the stability of curcumin in physiological matrices were investigated by Wang et al. (Wang et al., 1997). It was reported that when curcumin was added to 0.1 M phosphate buffer (pH 7.2), more than 90% of curcumin was degraded (Wang et al., 1997). The absorbance at 426 nm decreased to approximately 50% after 5 min, and after 10 min the remaining absorbance was only about 10%. However, we presently do observe an almost 40% degradation at 4h in pH 1.2 medium.

The order of kinetics of free curcumin was zero order at all investigated pH conditions, while in case of C-SLN the order was first order except at pH 9 (zero order). However even at pH 9, $t_{1/2}$ increased 5 times and rate constant of C-SLN was 80% less than that for free curcumin. Very interestingly at physiological pH of 7.4, an almost 90% decrease in k value and a 10 times increase in tin was observed. Similarly, protection provided by the other two pH buffers was also substantial and similar increase in $t_{1/2}$ (13.3 times at pH 1.2 and 104 times at pH 6.8) and decrease in k was observed in comparison to free curcumin (table 7).

TABLE 7

| Various degradation kinetics parameters for free curcumin and CSLNs (n = 6) | | | | | | | |
|---|---|---|---|---|---|---|---|
| | | Free cur | | | C-SLNs | | |
| Order | pH | k value | $t_{1/2}$ | $r^2$ | k value | $t_{1/2}$ | $r^2$ |
| zero order | pH 1.2 | 0.039 | 17.34 | 0.934 | — | — | — |
| | pH 6.8 | 0.52 | 1.32 | 0.967 | — | — | — |
| | pH 7.4 | 0.073 | 9.4 | 0.984 | — | — | — |
| | pH 9 | 0.95 | 0.669 | 0.994 | 0.195 | 3.55 | 0.891 |
| First order | pH 1.2 | — | — | — | 0.003 | 231 | 0.98 |
| | pH 6.8 | — | — | — | 0.005 | 138 | 0.962 |
| | pH 7.4 | — | — | — | 0.007 | 99 | 0.89 |

In-Vitro Release of C-SLNs

Jacketed franz-diffusion cells were used for the determination of in-vitro release of free curcumin and curcumin from C-$SLN_{aq}$. These cells consist of the donor and the receptor chamber between which dialysis membrane is positioned. The dialysis membrane was soaked in double distilled water for 12 h prior to use. The whole system was water jacketed and thermostatically controlled by an external circulating water bath at 37° C.±1° C. The used receptor media consisted of 50% ethanol in distilled water. Initially we used different buffer systems i.e., pH 1.2, pH 6.8, pH 7.4 but it resulted in simultaneous degradation of curcumin so that estimations could not be made correctly. 0.6 ml each of C-$SLN_{aq}$ and free curcumin dispersed in 1% (w/v) CMC was poured evenly on the donor side of the dialysis membrane and the cells were covered with paraffin film to avoid evaporation of the loaded sample and with aluminium foil to prevent photodegradation of curcumin. The receptor media was stirred throughout the experiment, using a magnetic stirrer. Iml aliquots were withdrawn regularly from the receptor compartment at various times starting at 30 min and replaced by an equal volume of fresh receptor medium. The samples were analysed, immediately, spectrophotometrically at 425 nm.

Solubility of curcumin in water at room temperature was determined to be 0.003±0.002 μg/ml. Thus to provide sink condition, 50% (v/v) ethanol in which solubility of curcumin is 0.693 mg/ml was chosen as the receptor medium. The drug release from C-SLNs (n=6) and free curcumin is shown in FIG. 11. The release of curcumin from C-SLN was extended upto 96 h (4 days) with 97±17.49% release and a zero order of release (i.e. controlled release). A first order release was observed in case of free drug, which was completely released within 8 h. C-SLN followed Korsmeyerpeppas model whereas free curcumin appeared to follow Hixon model (table 8).

TABLE 8

Linear correlation coefficients obtained for in vitro release data from various models

| Model | Formulations: C-SLNs | Free curcumin |
| --- | --- | --- |
| Zero order ($r^2$) | 0.992 | 0.936 |
| First order ($r^2$) | 0.912 | 0.990 |
| Higuchi ($r^2$) | 0.937 | 0.878 |
| Korsmeyerpeppas model ($r^2$) | 0.991 | 0.692 |
| Hixon-crowell model ($r^2$) | 0.946 | 0.995 |

3. Toxicity Studies of C-$SLN_{aq}$

A. Acute Oral Toxicity Studies (OECD Guideline 425)

Selection of Animals

Healthy young adult nulliparous and nonpregnant female Wistar rats were procured from Central Animal House of Panjab University, Chandigarh, India. A total of 5 animals were randomly selected and kept in their cages for 7 days prior to dosing to allow for their acclimatization to the laboratory conditions. The animals were supplied with drinking water and food daily. Clean paddy husk bedding was provided to the animals which was changed every $3^{rd}$ day. Animals were marked suitably and their individual weights were taken.

Experimental Design

Acute toxicity studies were performed in accordance with the OECD guideline 425. In accordance to the OECD guidelines, for any formulation, if information is not available for estimates of the $LD_{50}$, a starting dose of 175 mg/kg is used. Further, using half-log units (corresponding to a dose progression factor of 3.2) between doses, three sequential doses of 175, 550, 2000 mg/kg were selected for conducting the test. Animals, one at a time, were dosed in sequence, usually at 24h intervals. Next animal was treated with sequentially higher dose only when we were confident of the survival of the previously dosed animal and if no untoward signs were observed during this period. The highest dose (2000 mg) was administered to two more animals after the first animal survived the dose. All animal protocols were approved by the institutional animal ethics committee vide letter number 107/IAEC/18 and approval number PU/45/99/CPCSEA/IAEC/2017/89.

Observations

Animals were observed individually during the first 30 minutes after completing the dosing and periodically thereafter during the first 24 hours and then daily, for a period of 14 days. All observations were systematically recorded with individual records being made for each animal. Observations included change in skin, fur, eyes and mucous membranes. Individual weights of animals were recorded before the administration of drug on 1st day of the study and thereafter on the 7th and 14th day of the experiment.

Average Body Weight

The body weights of individual animals at all the tested doses are given in table 9.

TABLE 9

Body weight of animals on day 0, day 7 and day 14 after administration of single oral doses in ascending order

| Dose (mg/kg) | Body weight (g): 0 day | 7th day | 14th day |
| --- | --- | --- | --- |
| 175 | 143 | 145 | 148 |
| 550 | 186 | 186 | 188 |
| 2000 | 204 | 200 | 203 |
| 2000 | 194 | 189 | 192 |
| 2000 | 147 | 154 | 150 |

Feed and Water Consumption

The animals did not show any change in feed and water consumption during the study period.

Wellness Parameter

Skin, fur, eyes, mucous membrane, behavioral pattern and sleep of the animals was normal in all the groups. No convulsion, lethargy or reduced activity was observed.

Mortality and Morbidity

None of the animals showed any mortality and morbidity.

Gross Necropsy

All the organs of the treated animals were normal with no signs of necrosis and their average weights are given in table 10.

TABLE 10

Weight (grams) of organs of rats treated with different doses of C-SLNs

| Organ | Organ weight of various dose groups of rats: 175 mg/kg | 550 mg/kg | 2000 mg/kg (n = 3) | naïve |
| --- | --- | --- | --- | --- |
| Liver | 6.39 | 6.43 | 6.57 ± 0.38 | 6.56 |
| Stomach | 2.05 | 2.18 | 2.03 ± 0.14 | 2.22 |
| Kidney | 0.88 | 0.93 | 0.83 ± 0.05 | 0.85 |
| Spleen | 0.28 | 0.37 | 0.30 ± 0.07 | 0.32 |
| Brain | 1.19 | 1.27 | 1.19 ± 0.12 | 1.26 |

Histological Examination of Various Organs

After 14 days, the animals were sacrificed by cervical dislocation. The liver, kidney, spleen, brain and stomach were stripped out and immediately dipped in 10% v/v formalin for histological examination.

From histological report, it was observed that all the vital organs i.e., liver, kidney, stomach, brain and spleen of animals dosed with the highest dose of 2000 mg/kg were normal. No degeneration or abnormality of any kind was found in any of the organsin comparison to the naive animal (FIGS. 12 (*a*) and (*b*)).

B. Repeated Dose 28-Day Oral Toxicity Study (OECD Guideline 407)

Selection of Animals

Young male and female (nulliparous and non pregnant) Wistar Rats were procured from Central Animal house of Panjab University. Animals were selected randomly and kept in their cages for 7 days, prior to dosing, to allow acclimatization to the laboratory conditions. Five Animals were housed per cage with natural day/night cycles. All animals were supplied with clean drinking water and food daily. Clean paddy husk bedding was provided to the animals which was changed every $3^{rd}$ day. All animal protocols were approved by the institutional animal ethics committee vide letter number 107/IAEC/18 and approval number PU/45/99/CPCSEA/IAEC/2017/89.

Selection of Doses

OECD TG 407 requires that the highest dose level should be selected with the aim of inducing toxic effects but not death or severe suffering. Thereafter, a descending sequence of doses should be selected with a view of demonstrating any dosage related response and no-observed-adverse effects at the lowest dose level (NOAEL). Since an oral therapeutic dose of 1-2.5 mg/kg is proposed for C-SLNs hence it was considered to fix the highest dose at a 20 times higher level of 50 mg/kg. Accordingly, 25 mg/kg and 5 mg/kg were taken as the middle and the lower dose respectively. Each dose group had a total of 10 animals (5 males and 5 females). For reversibility, persistence or delayed occurrence of toxic effects due to treatment, an additional satellite group of 10 animals in the top dose was also included in the study.

Administration of Doses

C-SLNs were administered orally using an oral feeding canula. The animals were dosed daily for a period of 28 days, as a single dose at 10.00 am each day.

Observations

The animals were observed throughout the dosing period. General clinical observations were made each day before administering the dose. Animals in the satellite group were observed for another 14 days post treatment. Detailed clinical observations once before the first exposure and weekly thereafter were made on individual animals at a standard arena outside the home cage between 3 PM to 4 PM on each occasion. The observation included change in skin, fur, eyes, occurrence of secretions and excretions and autonomic activity (e.g. piloerection, unusual respiratory pattern) as well as change in gait, posture and response to handling as well as the presence of tonic or clonic movements, stereotypes (e.g. excessive grooming, repetitive circling) or bizarre behaviour (e.g. self mutilation, walking backwards).

Body Weight and Feed/Water Consumption

Rats in all groups were given free access to both drinking water and food throughout the study. Their body weights were measured weekly. Dose volume to be administered was reviewed every week considering that the body weight tends to change over such long study period.

The animals in various groups did not show any significant alteration in feed and water consumption.

Weekly body weights of all the animals of various dose groups, along with their means are listed in table 11.

TABLE 11

| Weekly body weight | | | | | | | | | | | | | |
|---|---|---|---|---|---|---|---|---|---|---|---|---|---|
| Day | Dose | Weight (grams) | | | | | | | | | | Mea | S.D. |
| Day 0 | 50 | 161 | 152 | 158 | 184 | 197 | 198 | 238 | 203 | 240 | 223 | 195 | 32 |
| | 25 mg/k | 159 | 176 | 163 | 264 | 182 | 168 | 191 | 170 | 204 | 168 | 184 | 31 |
| | 5 mg/kg | 158 | 143 | 167 | 187 | 198 | 183 | 174 | 200 | 150 | 174 | 173 | 19 |
| | Satellit | 154 | 193 | 180 | 159 | 157 | 170 | 132 | 154 | 160 | 145 | 160 | 17 |
| Day 7 | 50 mg/k | 170 | 168 | 170 | 193 | 210 | 230 | 210 | 240 | 215 | 256 | 206 | 31 |
| | 25 mg/k | 161 | 182 | 179 | 247 | 189 | 184 | 202 | 176 | 208 | 160 | 188 | 26 |
| | 5 mg/kg | 165 | 145 | 178 | 199 | 210 | 200 | 186 | 220 | 160 | 196 | 185 | 24 |
| | Satellit | 146 | 200 | 199 | 165 | 168 | 200 | 170 | 240 | 190 | 180 | 185 | 26 |
| Day 14 | 50 mg/k | 163 | 188 | 184 | 212 | 198 | 247 | 215 | 262 | 223 | 240 | 213 | 31 |
| | 25 mg/k | 173 | 190 | 182 | 257 | 196 | 200 | 218 | 187 | 230 | 178 | 201 | 26 |
| | 5 mg/kg | 172 | 150 | 184 | 193 | 215 | 206 | 196 | 229 | 163 | 204 | 191 | 24 |
| | Satellit | 152 | 197 | 204 | 170 | 173 | 204 | 170 | 174 | 186 | 192 | 182 | 17 |
| Day 21 | 50 mg/k | 162 | 194 | 179 | 200 | 219 | 243 | 208 | 273 | 218 | 251 | 214 | 34 |
| | 25 mg/k | 168 | 174 | 188 | 241 | 195 | 196 | 208 | 182 | 235 | 174 | 196 | 25 |
| | 5 mg/kg | 178 | 163 | 192 | 187 | 220 | 214 | 202 | 221 | 170 | 210 | 195 | 201 |
| | Satellit | 158 | 204 | 212 | 176 | 179 | 208 | 167 | 182 | 196 | 199 | 188 | 18 |
| Day 28 | 50 mg/k | 160 | 200 | 195 | 237 | 184 | 203 | 219 | 195 | 224 | 259 | 207 | 28 |
| | 25 mg/k | 175 | 187 | 199 | 248 | 202 | 204 | 200 | 191 | 228 | 180 | 201 | 22 |
| | 5 mg/kg | 188 | 170 | 199 | 193 | 224 | 222 | 195 | 230 | 173 | 219 | 201 | 22 |
| | Satellit | 167 | 208 | 220 | 184 | 173 | 215 | 178 | 192 | 189 | 206 | 193 | 18 |
| Day 35 | Satellit | 173 | 215 | 211 | 190 | 182 | 220 | 183 | 201 | 197 | 212 | 198 | 16 |
| Day 42 | Satellit | 180 | 220 | 218 | 197 | 189 | 214 | 185 | 202 | 204 | 220 | 202 | 15 |

It was observed that all of the treated groups were normal. There was no change in fur skin colour, eyes and mucous membranes. None of the animals showed tremors, convulsions, salivation, lethargy, sleep and coma.

No mortality was observed in any of the animals at any dose.

Behavioural Observations

Sensory Functioning: Hot Plate

Rats were placed inside a fiber glass cylinder (15 cm diameter, 30 cm height), one at a time, with a thermally controlled metal base maintained at 55±2° C. Rats responded by jumping on the plate or licking their paws. A cut-off time of 15 seconds was set to prevent injury to rat paws. The responses were recorded on day 29 (post 28th day daily dosing) and 14 days thereafter for satellite group.

No significant difference was observed between any dose group ($p<0.05$) as seen from FIG. 13.

Muscle Strength: Rota Rod

The muscle strength was measured using rota rod. The apparatus consisted of a horizontal metal rod of 7 cm diameter coated with rubber and attached to a motor whose speed is adjusted to 20 rotations per minute. The rod, 75 cm in length, is divided into three sections by plastic discs, thereby allowing the simultaneous testing of 3 rats. The height of the rod is adjusted at about 50 cm above the table top, to discourage animals from jumping off the roller. When a rat falls off from the rotating rod onto the plate below, the plate trips and the corresponding counter is disconnected, thereby recording the time that the animal spent on the rota rod. A cut-off time of 300 seconds was observed to prevent injury to rat paws. The responses were recorded on day 29 (post 28th day daily dosing) and 14 days thereafter for satellite group.

No significant difference was observed between any dose group ($p<0.05$) versus the naive animals as seen from FIG. 14.

Locomotor Activity: Actophotometer

The locomotor activity can be easily measured using an actophotometer which operates on photoelectric cells which are connected in circuit with a counter. When the beam of light falling on the photocell is cut off by the animal, a count is recorded. The actophotometer presently used had square area in which the animal can move freely. Each animal was placed for 5 minutes in the activity cage and its activity was noted. The responses were recorded on day 29 (post 28th day daily dosing) and 14 day thereafter for satellite group.

There was a significant decrease ($p<0.05$) in rearing of 50, 25 and 5 mg/kg dose groups versus naive (FIG. 15). However, no significant difference was observed between naive versus satellite group ($p\leq0.05$). Howsoever, in case of ambulation all groups were similar ($p\leq0.05$).

Clinical Biochemistry

Clinical biochemical estimations are recommended to investigate major toxic effects in tissues and specifically, to determine any detrimental effects in kidney and liver. The blood samples were collected from randomly selected animals, post treatment (day 28 for all groups and day 42 for the satellite group) and were calculated for changes in complete blood count, liver function test, renal function test, total lipid profile and sugar, in comparison to the values obtained for the control group. For haematological and biochemical studies, three animals per sex were randomly selected.

Haematology

No significant difference was found in various haematological parameters of different dose groups of rats in comparison to the naive control group ($p\leq0.05$) (table 12).

TABLE 12

Complete blood count of animals of various dose groups

| Test | Groups | | | | |
|---|---|---|---|---|---|
| | Naive | 5 mg/kg | 25 mg/kg | 50 mg/kg | Satellite |
| Haemoglobin | 14.26 ± 2.51 | 13.30 ± 0.70 | 15.00 ± 0.85 | 14.13 ± 0.62 | 14.13 ± 0.40 |
| Neutrophils | 30.70 ± 5.43 | 68.63 ± 0.99 | 68.83 ± 4.80 | 46.70 ± 25.91 | 67.83 ± 1.82 |
| Lymphocytes | 62.23 ± 5.75 | 24.90 ± 1.30 | 23.37 ± 3.10 | 44.23 ± 24.30 | 26.28 ± 2.13 |
| Monocytes | 7.07 ± 1.57 | 6.47 ± 1.23 | 7.80 ± 1.82 | 9.07 ± 3.01 | 5.93 ± 1.30 |
| RBC | 6.81 ± 0.95 | 6.77 ± 0.40 | 7.30 ± 0.93 | 7.21 ± 0.32 | 6.89 ± 0.28 |
| PCV (Packed cell volume) | 35.77 ± 4.44 | 34.63 ± 0.86 | 40.33 ± 3.86 | 36.80 ± 2.39 | 37.23 ± 1.67 |
| MCV (Mean corpuscular volume) | 52.57 ± 1.06 | 51.20 ± 1.80 | 55.47 ± 3.29 | 51.05 ± 1.38 | 54.03 ± 0.38 |

Blood Sugar

No significant difference was observed in blood sugar levels of dosed animals in comparison to naive control group ($p<0.05$) as seen from FIG. 16.

Renal Function Test

C-SLN treatment at all the doses did not show any significant change in serum uric acid and creatinine levels ($p<0.05$) (table 13; FIG. 17). However, there was a significant increase in the urea blood levels of all the dose groups in comparison to naive control group ($p\leq0.05$) (table 13; FIG. 18).

TABLE 13

Renal function test of animals of various dose groups

| Test | Groups | | | | |
|---|---|---|---|---|---|
| | Naive | 5 mg/kg | 25 mg/kg | 50 mg/kg | Satellite |
| Urea Blood Level | 23.00 ± 9.54 | 59.33 ± 4.04 | 48.00 ± 9.54 | 48.50 ± 18.29 | 52.67 ± 4.62 |
| Creatinine Serum | 0.48 ± 0.03 | 0.49 ± 0.10 | 0.59 ± 0.02 | 0.66 ± 0.08 | 0.51 ± 0.04 |
| Uric Acid Serum | 2.32 ± 0.53 | 1.16 ± 0.42 | 1.26 ± 0.02 | 1.04 ± 0.50 | 1.51 ± 0.16 |

Liver Function Test

No significant change ($p<0.05$) in SGPT and ALP was observed in animalstreated with different doses of C-SLNs. A significant increase in the SGOT levels in 50 mg/kg and 5 mg/kg dose groups versus naive control group ($p\leq0.05$) but not satellite group and 25 mg/kg dose group (table 14) was however observed. Further, changes produced at 50 mg/kg dose group were reversed completely in the satellite group.

TABLE 14

| Liver function test of animals of various dose groups | | | | | |
|---|---|---|---|---|---|
| | Groups | | | | |
| Liver function test | Naive | 5 mg/kg | 25 mg/kg | 50 mg/kg | Satellite |
| Aspartate Amonitransferase (SGOT) | 135.67 ± 49.32 | 183.00 ± 41.77* | 199.17 ± 61.80 | 234.33 ± 25.04* | 150.33 ± 14.28 |
| Alanine Amonitransferase (SGPT) | 70.17 ± 18.21 | 68.20 ± 9.83 | 89.33 ± 16.06 | 75.67 ± 22.30 | 65.33 ± 7.97 |
| Alkaline Phosphatase (ALP) | 195.33 ± 69.08 | 276.67 ± 245.96 | 351.33 ± 158.90 | 350.67 ± 134.43 | 169.33 ± 21.01 |

Total Lipid Profile

No significant difference ($p \leq 0.05$) was observed in any of the lipid profile parameters observed for various dose groups of C-SLNs in comparison to the naive control group (table 15).

TABLE 15

| Lipid profile of animals of various dose groups of C-SLNs | | | | | |
|---|---|---|---|---|---|
| | Groups | | | | |
| Test | naive | 5 mg/kg | 25 mg/kg | 50 mg/kg | Satellite |
| Cholesterol Total | 54.00 ± 4.58 | 53.33 ± 4.51 | 47.00 ± 7.94 | 53.33 ± 10.03 | 46.33 ± 7.02 |
| High Density Lipoprotein | 12.33 ± 3.51 | 13.33 ± 3.06 | 12.00 ± 1.00 | 13.33 ± 4.23 | 13.67 ± 3.21 |
| Low Density Lipoproteins | 23.33 ± 12.50 | 17.67 ± 7.57 | 15.67 ± 4.73 | 14.83 ± 11.82 | 8.00 ± 6.24 |
| Very Low Density Lipoprotein | 18.33 ± 13.65 | 22.33 ± 2.08 | 19.33 ± 7.09 | 25.17 ± 6.05 | 24.67 ± 2.31 |
| Triglycerides Serum | 93.00 ± 67.91 | 112.33 ± 9.87 | 96.00 ± 35.38 | 124.83 ± 30.20 | 123.67 ± 12.86 |
| Total/HDL Cholestrol Ratio | 4.60 ± 1.15 | 4.17 ± 1.10 | 3.93 ± 0.90 | 4.12 ± 0.62 | 3.43 ± 0.42 |
| LDL/HDL Cholestrol Ratio | 2.20 ± 1.51 | 1.47 ± 0.85 | 1.33 ± 0.51 | 1.05 ± 0.73 | 0.53 ± 0.32 |

Gross Necropsy

All the animals in the study were subjected to a full, detailed gross necropsy which included the careful examination of the external surface of the body, all orifices and cranial, thoracic and abdominal cavities and their contents.

No significant difference ($p < 0.05$) was observed between the weight of organs of various dose groups with respect to naive control animals (table 16).

TABLE 16

| Average organ weights (grams) of rats exposed to C-SLNs | | | | | |
|---|---|---|---|---|---|
| Organ | Naive Weight (g) | 5 mg/kg Weight (g) | 25 mg/kg Weight (g) | 50 mg/kg Weight (g) | Satellite Weight (g) |
| Liver | 6.48 ± 0.74 | 6.95 ± 0.77 | 6.69 ± 0.67 | 6.64 ± 0.64 | 6.59 ± 0.48 |
| Stomach | 2.05 ± 0.17 | 2.09 ± 0.24 | 2.05 ± 0.27 | 2.11 ± 0.24 | 2.05 ± 0.21 |
| Kidney | 0.84 ± 0.06 | 0.82 ± 0.07 | 0.84 ± 0.09 | 0.81 ± 0.07 | 0.81 ± 0.09 |
| Spleen | 0.36 ± 0.05 | 0.35 ± 0.05 | 0.35 ± 0.05 | 0.34 ± 0.05 | 0.36 ± 0.05 |
| Brain | 1.35 ± 0.27 | 1.26 ± 0.11 | 1.26 ± 0.11 | 1.31 ± 0.15 | 1.32 ± 0.12 |

Histology

The animals were sacrificed by cervical dislocation after 28 days (42 days for satellite group). The liver, kidney, brain, spleen and stomach were removed and stored in 10% v/v formalin till histological examination. Histology of one representative animal of each dose group was conducted and compared with naive control rats.

From histological reports, it was observed that in 50 mg/kg dose, the liver showed hyperplasia of Kupffer cells, possibly due to a toxic reaction which was reversed as no such hyperplasia was observed in satellite group. Kidney showed normal glomeruli and tubules and stomach showed normal gastric mucosa in all the dose groups. Spleen and brain were also normal in all the dose groups (FIGS. 19, 20, 21, 22 and 23).

4. Antimicrobial Activity of Prepared Curcumin Loaded Solid Lipid Nanoparticles Against *Staphylococcus aureus* 9144

The effect of free curcumin dissolved in DMSO, curcumin loaded solid lipid nanoparticles, blank nanoparticles and curcumin dispersed in 0.5% w/v CMC on the planktonic growth of *Staphylococcus aureus* 9144 was studied using the CLSI M27-A2 methodology as per the Clinical Laboratory Standards Institute (CLSI) guideline. The MH medium containing varying (i.e., 16 to 2048 μg/ml) concentrations of curcumin loaded solid lipid nanoparticles was added into 96-well plates. Wells without the test molecule served as a control. The inoculum was added to the repective test molecule dilutions so that 200 μl of the assay system in each well contained the particular concentration of the test molecule and the cell density of $5 \times 10^5$ cfu/ml. The plates were incubated at 37° C. for 24 h. After 24 h of incubation antimicrobial activity was evaluated by plate count method.

The lowest concentration of the test molecule that caused ≥50% reduction of the cells in comparison with the control was noted as the MIC.

Antimicrobial effect of prepared curcumin loaded solid lipid nanoparticles against *Staphylococcus aureus* ATCC 9144 is given in table 17. MIC of curcumin SLNs was found at 64 μg/ml whereas no inhibition was found in case of curcumin suspension.

TABLE 17

Antimicrobial effect of curcumin loaded solid lipid nanoparticles against *Staphylococcus aureus* ATCC 9144.

| Sr. No. | Agents | MIC (μg/ml) |
|---|---|---|
| 1 | Curcumin solution in DMSO | 32 |
| 2 | Curcumin suspension in CMC | No inhibition |
| 3 | Curcumin loaded solid lipid nanoparticles | 64 |
| 4 | Blank solid lipid nanoparticles | No inhibition |

5. Antimicrobial Activity of Prepared Curcumin Loaded Solid Lipid Nanoparticles Against *Staphylococcus aureus* 9144 Biofilms.

The biofilms of *S. aureus* were studied in polystyrene microplates using the in vitro biofilm model. Each well of the microplate was inoculated with 100 μl of PBS containing $1\times10^7$ cells/ml. The plates were incubated at 37° C. for 90 min to allow the adhesion of cells on the solid surface. The non-adhered cells were removed by washing with PBS, and 200 μl of the BHI medium was added to the wells. The activity against biofilm formation was studied by the addition of free curcumin dissolved in DMSO, curcumin loaded solid lipid nanoparticles, blank nanoparticles and curcumin dispersed in 0.5% w/v CMC immediately after the adhesion. To study the effect on mature biofilms, the test molecule was added after 24 h. The microplates were incubated at 37° C. for 24 h and washed with PBS to remove the planktonic cells. Biofilm growth was analyzed using the XTT metabolic assay. The XTT solution of 1 mg/ml concentration was prepared in PBS and stored at −20° C. until use. The menadione solution, prepared in acetone, was added to the XTT solution so as to get a concentration of 4 μM. The wells containing biofilms were washed with PBS, and 100 μl of the XTT-menadione solution was added to each, followed by incubation at 37° C. for 5 h, in the dark. The intensity of the color formation by the water-soluble formazan product was measured at 450 nm using a microplate reader which indicated the metabolic activity relative to the biofilm growth (i.e., RMA). Wells without the test compounds were considered as the control, while the wells without biofilms served as the blank. The lowest concentration of the test molecule causing ≥50% reduction of the RMA was considered the MIC for the biofilm.

Antimicrobial effect of prepared curcumin loaded solid lipid nanoparticles against *Staphylococcus aureus* ATCC 9144 biofilms is given in table 18. CSLNs exhibit biofilm formation inhibition at 512 μg/ml and MIC against mature biofilm was found at 2048 μg/ml. Curcumin suspension did not any inhibition.

TABLE 18

Antimicrobial effect of prepared curcumin loaded solid lipid nanoparticles against *Staphylococcus aureus* ATCC 9144 biofilms

| Sr. No. | Agents | MIC (μg/ml) |
|---|---|---|
| | Biofilm Formation | |
| 1 | Curcumin solution in DMSO | 64 |
| 2 | Curcumin suspension in CMC | No inhibition |
| 3 | Curcumin loaded solid lipid nanoparticles | 512 |
| | Mature Biofilms | |
| 1 | Curcumin solution in DMSO | No inhibition |
| 2 | Curcumin suspension in CMC | No inhibition |
| 3 | Curcumin loaded solid lipid nanoparticles | 2048 |

6. Preparation of C-$SLN_{HG}$ and Preparation of C-$SLN_{bent}$

Briefly 1.5% w/v carbopol 934P was soaked in water overnight. For neutralising basic nature of carbopol, it was treated with 1-2 drops of triethanolamine the next day to get a uniform gel. For every 9 g of C-$SLN_{aq}$, 1 g of carbopol gel was added to get 10 g of C-$SLN_{HG}$ after thorough mixing.

Bentonite and titanium dioxide were passed through a fine sieve (no=120) before use. Known amounts of the two (15% w/w bentonite and 3% w/w of titanium dioxide) were triturated thoroughly with glycerine and sesame oil in a mortar and pestle till no lumps were observed. C-SLNs were added to this mixture to obtain a smooth paste like consistency to obtain C-$SLN_{bent}$.

Total Drug Content of the C-SLN Hydrogel (C-$SLN_{HG}$) and C-$SLN_{bent}$

TDC of C-$SLN_{HG}$ was measured by mixing its known quantity with sufficient quantity of chloroform:methanol (1:1) and vortexing for 5 min. The obtained solution was filtered and analysed spectrophotometrically at $\lambda_{max}$425 nm using respective blank.

C-$SLN_{bent}$formulation was diluted to 1000 times with chloroform:methanol (1:1). It was mixed thoroughly by vortexing for 5 min, filtered and analysed spectrophotometrically at $\lambda_{max}$425 nm using respective blank.

TDC was determined using the following equation:

$$\text{Total drug content (\%)} = \frac{\text{Observed drug content}}{\text{Actual drug content}} \times 100$$

The TDC of C-$SLN_{HG}$ was estimated to be 5.22 mg/gm.

TDC of C-$SLN_{bent}$ was estimated to be 4.35 mg/gm.

Texture Analysis of (C-$SLN_{HG}$) and C-$SLN_{bent}$

The mechanical property of developed formulation was determined using a software controlled penetrometer, texture analyser (Stable Micro systems, Surrey, UK). The formulation was transferred to a bottle and kept in a ultrasonic water bath to remove air bubbles for 20 min and the temperature was adjusted to 37° C. The probe was compressed into each formulation at a defined rate of 2 mm $s^{-1}$. Various mechanical parameters such as hardness, compressibility, adhesiveness and cohesiveness of the gel formulation were estimated.

Hardness is determined as the maximum peak force during the first compression cycle.

Compressibility is the work required to deform the product during the first compression.

Adhesiveness is calculated as the negative force area for the first compression cycle and represents the work required to overcome the attractive forces between the surface of the gel and surface of the probe.

Cohesiveness is the ratio of the area under the force-time curve produced on the second compression cycle to that produced on the first compression cycle, where successive compression are separated by a defined recovery period.

TPA (texture profile analysis) defines the mechanical parameters in terms of hardness, adhesiveness, cohesiveness, compressibility and consistency. The TPA graph and calculated mechanical properties of C-SLN$_{HG}$ and C-SLN$_{bent}$ are presented in table 19 and 20 and FIG. 24.

The hardness is defined as the maximum peak force during the first compression cycle. The hardness of C-SLN$_{HG}$ and C-SLN$_{bent}$, which determines the ease of application on the skin, was 676.445 and 17168.325 respectively, acceptable for topical gel application. Adhesiveness is defined as the negative force area for the first compression cycle. Adhesiveness is the work required to overcome the attractive forces between the surface of the sample and the surface of the probe and it is related to bioadhesion (Jones et al., 1996b.) The adhesiveness value of C-SLN$_{HG}$ and C-SLN$_{bent}$ was calculated to be0.229 and0.783 g. sec. TPA also provides the information about the cohesiveness. Cohesiveness describes the ratio of the area under the force-time curve produced on the second compression cycle to that produced on the first compression cycle. The high value of cohesiveness provides full structural recovery following gel application. In present study, cohesiveness value of C-SLN$_{HG}$ was −3109.95 g which is nominal for topical application (Karavana et al., 2009)

From the results of TPA experiments and spreadability test, it can be concluded that C-SLN$_{HG}$ and C-SLN$_{bent}$ have suitable mechanical properties for topical administration.

TABLE 19

Texture profile analysis of C-SLN$_{HG}$

| Sample | Firmness (g) | Consistency (g · sec) | Cohesiveness (g) | Index of Viscosity (g · sec) |
|---|---|---|---|---|
| C-SLN$_{HG}$ | 13789.47 | 235960.97 | −3109.95 | −10072.06 |

TABLE 20

Spreadability test of C-SLN$_{HG}$ and C-SLN$_{bent}$

| Sample | Hardness (g) | Spreadability (g · sec) | Stickiness (g) | Adhesiveness (kg · sec) |
|---|---|---|---|---|
| C-SLN$_{HG}$ | 676.445 | 899.543 | −349.451 | −0.229 |
| C-SLN$_{bent}$ | 17168.325 | 14616.906 | 8748.061 | −0.783 |

Ex-vivo release of C-SLN$_{HG}$

Jacketed franz-diffusion cells were used for determining the permeability of C-SLN$_{HG}$ through rat skin. Average area of the skin in contact with the receptor medium was 2.95 $cm^2$ (n=6) and the average receptor chamber volume was 30 ml. 6-8 week old female Wistar rats were sacrificed by cervical dislocation. A section of the dorsal skin surface was depilated and excised from the animals with surgical scissors. Adhering fat and other visceral debris were carefully removed from the underneath surface of the skin sample. Receptor media comprised of 50% ethanol in distilled water. Circular skin pieces of a size slightly greater than the external circumference of donor compartment were cut and mounted onto the diffusion cell assembly, keeping the stratum corneum side facing upwards and the dermal side in contact with the receptor fluid. The whole system was water jacketed and thermostatically controlled by an external circulating water bath at 37° C.±1° C. The receptor media was stirred throughout the experiment, using magnetic stirrer at 800 rpm. 0.5 g of the C-SLN$_{HG}$ containing 3600 μg of curcumin or free curcumin gel in carbopol was applied evenly onto the donor side of the skin surface and the donor cell was covered with paraffin film and aluminium foil to prevent degradation. Iml aliquots were withdrawn from the receptor compartment at different time interval starting at 30 min, 1 h, 2 h, 4 h, 6 h, 8 h, 10 h, 12 h, and 24 h and replaced by an equal volume of fresh receptor medium. The samples were analysed immediately. After the completion of the study, the skin was wiped with moist cotton swab several times (6 times) to remove any residual formulation sticking to the skin. The cotton swab was put into 50% ethanol in distilled water and vortexed to dissolve all the formulation from the swabs into the solvent. Absorbance of this solvent after filtration, and suitable dilution was measured to estimate the amount of curcumin left unabsorbed. To calculate the amount of curcumin retained in the skin, 1% w/v skin homogenates of mounted skin samples were prepared in 50% ethanol and were analysed spectrophotometrically at 425 nm.

50% ethanol was used as the receptor medium to increase the solubility of curcumin and maintain the skin conditions as it is practically insoluble in water and undergoes extensive degradation in the buffers of physiological pH. Specific quantity of C-SLN$_{HG}$ equivalent to 2.45 mg of curcumin and free curcumin at a similar concentration dispersed in carbopol gel (free cur carbopol gel) were loaded onto the donor compartment and samples were withdrawn from the receptor medium (with replacement) at different time intervals upto 24 h. FIG. 25 shows the cumulative amount permeated per unit area versus time data. Results very clearly depict a significantly higher permeation (1.6 times) with C-SLN$_{HG}$ ($P<0.05$). Same is depicted in figure-26 where the amount absorbed is 1.6 times and amount retained in the skin is 4.5 times higher with C-SLN$_{HG}$ than free drug (FIG. 25 and FIG. 26).

The permeation of C-SLN$_{HG}$ followed the zero order reaction i.e. independent of the concentration whereas the free curcumin permeation followed first order kinetics. Korsmeyerpeppas model was best fitted to the data for C-SLN$_{HG}$ whereas Hixon model fitted best in case free curcumin (table 21).

TABLE 21

Linear correlation coefficients obtained from various models

| Model | Formulations | |
|---|---|---|
| | C-SLN$_{HG}$ | Free cur carbopol gel |
| Zero order ($r^2$) | 0.931 | 0.936 |
| First order ($r^2$) | 0.912 | 0.947 |
| Higuch ($r^2$) | 0.773 | 0.898 |
| Korsmeyerpeppas model ($r^2$) | 0.977 | 0.898 |
| Hixon model ($r^2$) | 0.913 | 0.936 |

In Vivo Release of C-SLN$_{bent}$

Approximately 24 h before the test, hair of the animals were removed by the application of a hair removing cream from the dorsal area of the trunk of the animals (n=6). Next day, 500 mg of the C-SLN$_{bent}$ was applied on a 1 $cm^2$ area of each animal and left for 30 minutes. After 30 minutes, the animals were sacrificed by cervical dislocation and the skin was wiped with moist cotton swab several times (6 times) to remove any residual formulation sticking to the skin. The cotton swab was then put into 50% ethanol in distilled water with appropriate dilution (1000 times) and mixed using vortex shaker. To calculate the amount of curcumin absorbed in the skin, 1% skin homogenates were prepared in 50% ethanol and were analysed spectrophotometrically at 425 nm.

From in vivo permeation study for C-SLN$_{bent}$, it was observed that percent amount unabsorbed on the skin was 59.14±7.71% whereas the amount of C-SLN$_{bent}$ retained in the skin was 21.13±6.16%. These values are significantly more (2.4 times) than those observed for C-SLN$_{HG}$ in ex-vivo studies. Absorption of moisture from the atmosphere by HG may dilute the application resulting in lower concentration gradient. The C-SLN$_{bent}$ probably forms an occlusive layer (latter is the property of SLNs also) resulting in significantly better permeation.

7. Dermal Toxicity Study of C-SLN$_{HG}$ and C-SLN$_{bent}$

A. Acute dermal toxicity study (OECD guideline 407)

Preparation of Animal Species

Adult albino rabbits (weight 1-2 kg) were used for the acute studies. Approximately 24 h before the test, fur was removed by closely clipping the dorsal area of the trunk of the animals after which hair were removed completely by applying a depilatory. Care was taken to avoid abrading the skin, and only animals with healthy, intact skin were used.

Dose Level

Dose of 0.5 g of C-SLN$_{HG}$ and C-SLN$_{bent}$ was applied to the test site.

Initial Test (In Vivo Dermal Irritation Corrosion Test Using One Animal)

In the present study, the in-vivo testing was done initially using one animal. The test substance was applied to a small area (approximately 6 cm$^2$) of skin and covered with a gauze patch, which was held in place with a non-irritating tape. Access by the animal to the patch and ingestion or inhalation of the test substance was prevented by applying the patch near the neck area. The exposure period was 4 h, after which the patch was removed and animal was observed for next 72 h for any signs of redness, erythema and oedema.

Confirmatory Test

Since no corrosive effect was observed with the first animal, the negative response was confirmed using two additional animals, each with one patch, for an exposure period of 4 h.

After removal of the patch, the animals were similarly observed for upto 72 h.

Clinical Observation

After removal of the patches, all animals were examined for signs of erythema and oedema as per the grading provided in (table 22). The responses were scored at 60 minutes, 24, 48 and 72 h after removal of the patch. For the initial test in one animal, the test site was also examined immediately after the patch was removed. The animals were kept under observation for the next 14 days when they were observed every day regularly.

The responses scored at 30 minutes, 60 minutes, and then at 24, 48 and 72 h after patch removal were zero, indicating that none of the treated animals showed any signs of adverse effects or toxicity, establishing safety of both C-SLN$_{HG}$ and C-SLN$_{bent}$ formulation (table 23). FIGS. 27 and 28 showed the absence of any adverse effects on the skin.

TABLE 22

| Grading of skin reaction | |
|---|---|
| Erythema and Eschar Formation | |
| No erythema | 0 |
| Very slight erythema | 1 |
| Well defined erythema | 2 |
| Moderate to severe erythema | 3 |
| Severe erythema (beef redness) to eschar formation preventing grading of erythema | 4 |
| Oedema Formation | |
| No oedema | 0 |
| Very slight oedema (barely perceptible) | 1 |
| Slight oedema (edges of area well defined by definite raising) | 2 |
| Moderate oedema (raised approximately 1 mm) | 3 |
| Severe oedema (raised more than 1 mm and extending beyond area of exposure) | 4 |

TABLE 23

Tabulation of scores for signs of irritation after various time intervals
Test substance: C-SLN$_{HG}$ and C-SLN$_{bent}$
Test Animals: albino rabbit

| Animal code | Signs | Dose mg/kg | 0 min | 30 min | 60 min | 1 hour | 24 hours | 48 hours | 72 hours |
|---|---|---|---|---|---|---|---|---|---|
| S-1 | Redness | 500 | 0 | 0 | 0 | 0 | 0 | 0 | 0 |
| | Erythema | 500 | 0 | 0 | 0 | 0 | 0 | 0 | 0 |
| | Oedema | 500 | 0 | 0 | 0 | 0 | 0 | 0 | 0 |
| S-2 | Redness | 500 | 0 | 0 | 0 | 0 | 0 | 0 | 0 |
| | Erythema | 500 | 0 | 0 | 0 | 0 | 0 | 0 | 0 |
| | Oedema | 500 | 0 | 0 | 0 | 0 | 0 | 0 | 0 |
| S-3 | Redness | 500 | 0 | 0 | 0 | 0 | 0 | 0 | 0 |
| | Erythema | 500 | 0 | 0 | 0 | 0 | 0 | 0 | 0 |
| | Oedema | 500 | 0 | 0 | 0 | 0 | 0 | 0 | 0 |

B. Repeated Dose 28-Day Dermal Toxicity Study (OECD Guideline 410)

Grouping of Rats

Individual weight of the animals was taken before the start of the study. Ten animals (5 male and 5 female) each with healthy skin were used for each test substance i.e. C-SLN$_{HG}$ and C-SLN$_{bent}$. Another set of 10 animals (5 male and 5 female) were used as control.

Limit Test

The repeated dose 28-day dermal toxicity study was performed in accordance with the OECD guidelines (OECD TG 410) According to this, 1000 mg/kg dose can be used as the if test substance is not expected to produce any toxic effects. Hence 1000 mg/kg was used presently as curcumin is expected to be safe on topical application and SLNs are also reported as a suitable topical system. The test substance (C-SLN$_{HG}$ and C-SLN$_{bent}$) was applied uniformly over an area which was approximately 10 percent of the total body surface area (10.5 cm$^2$) and further covered with a gauze patch, which was held in place with non-irritating tape. The application was repeated every day for 28 days.

Observation

The animals were observed throughout the dosing period. General clinical observations were made each day before administering the dose. These included change in skin, fur, eyes, occurrence of secretion and excretion and autonomic activity (e.g. piloerection, unusual respiratory pattern) as well as change in gait, posture and response to handling as well as the presence of tonic or clonic movements, stereotypes (e.g. excessive grooming, repetitive circling) or bizarre behaviour (e.g. self mutilation, walking backwards). Body weights were measured weekly.

Body Weight

No significant changes were observed in body weight of animals applied with 1000 mg/kg of C-SLN$_{HG}$ and C-SLN$_{bent}$ as indicated in table24

TABLE 24

Average body weight of animals in g (n = 10)

| Groups | 0 day | 7$^{th}$ days | 14$^{th}$ days | 21$^{st}$ days | 28$^{th}$ days |
|---|---|---|---|---|---|
| C-SLN$_{HG}$ | 165 ± 35 | 165 ± 35 | 165 ± 30 | 165 ± 35 | 165 ± 35 |
| C-SLN$_{bent}$ | 170 ± 30 | 170 ± 25 | 170 ± 30 | 170 ± 20 | 170 ± 20 |
| Naive | 150 ± 45 | 150 ± 45 | 150 ± 45 | 150 ± 45 | 150 ± 45 |

Wellness Parameter

Skin, fur, eyes, mucous membrane, behavioural pattern, salivation, sleep of the treated as well as control animals were found to be normal. No convulsion, lethargy, reduced activity and diarrhoea was observed with any of the treated animals. None of treated animal showed any adverse effects on the skin.

Histopathology

From the histopathological report, it was observed that skin specimens after the application of C-SLN$_{bent}$ and C-SLN$_{HG}$ were normal. FIG. 29 showed the absence of any histopathological changes on the skin.

8. Photostability Study

The photostability evaluation of free curcumin, C-SLN, C-SLN$_{HG}$ and C-SLN$_{bent}$ were investigated according to ICH guidelines. The free drug was dispersed in carboxy methyl cellulose (1% w/v) at a concentration of 6 mg/ml. Free curcumin and C-SLNs were stored in both clear glass and amber coloured 100 ml containers while C-SLN$_{HG}$ and C-SLN$_{bent}$ were packed in aluminium tubes.

The above samples were placed in photostability chamber and exposed to light providing illumination of not less than 1.2 million lux hours for 10 days. After 10 days the containers were withdrawn and C-SLN$_{aq}$ was evaluated for total drug content, entrapment efficiency, particle size, zeta-potential and PDI. Samples of free drug, C-SLN$_{HG}$ and C-SLN$_{bent}$ were analysed for total drug content. The concentration at zero time was considered as 100%.

The present study establishes the protection offered to curcumin by the lipid matrix of SLNs. It is clearly obvious that C-SLNs offer significant protection in contrast to free curcumin. SLNs stored in amber colour and transparent containers did not show any significant degradation in terms of change in TDC and entrapment (P>0.05). PDI was also similar, however some increase in particle size was observed (table 25). On the other hand, 21.7% degradation was observed upon storage of free curcumin in even amber coloured containers while it increased to 35% in transparent containers. In contrast only a 1% degradation occurred in case of C-SLNs upon storage in transparent containers. Similarly, C-SLN$_{HG}$ and C-SLN$_{bent}$ stored in aluminium tubes were found to be stable (<2% change in TDC) (table 26).

TABLE 25

Photostability of free curcumin and C-SLNs (n = 3)

| Glass ware | Days | TDC % Free Curcumin | TDC % C-SLNs | % Entrapment C-SLNs | Particle size(nm) C-SLNs |
|---|---|---|---|---|---|
| Amber glass | 0 day | 100.00 ± 0 | 100.00 ± 0 | 100.00 ± 0 | 316.9 ± 0 |
| | 10 days | 78.31 ± 7.1 | 99.64 ± 0.025 | 99.82 ± 0.6 | 344.1 ± 7.6 |
| Transparent | 0 day | 100.00 ± 0 | 100.00 ± 0 | 100.00 ± 0 | 316.9 ± 0 |
| | 10 days | 65.51 ± 7.5 | 98.93 ± 0.05 | 99.03 ± 0.06 | 348.2 ± 5.6 |

TABLE 26

Photostability testing of C-SLN$_{HG}$ and C-SLN$_{bent}$

| Parameter | C-SLN$_{HG}$ 0 Day | C-SLN$_{HG}$ 10 Days | C-SLN$_{bent}$ 0 Day | C-SLN$_{bent}$ 10 Days |
|---|---|---|---|---|
| TDC (%) | 100.00 | 98.04 | 100.00 | 98.05 |

9. Stability Study

Stability studies were also conducted as per the ICH guidelines. C-SLN$_{aq}$ dispersion (100 ml) and free curcumin dispersed in 1% w/v carboxymethyl cellulose were placed at various temperature i.e. 4° C., 30° C., and 40° C. for evaluating long term and accelerated stability. Samples were withdrawn at 0, 1, 3, 6 and 12 months for 4° C. and 0 and 1 month for 30° C., and 40° C. and evaluated for total drug content, entrapment efficiency, particle size and PDI.

After 1 month of stability at various temperatures, the C-SLNs were found to be stable with no significant increase in TDC, PDI, and (P>0.05) except in case of EE and particle size at 40° C. when the differences though within limits are significant (p<0.001). However, both C-$SLN_{HG}$ and C-$SLN_{bent}$ showed a significant change in drug conc. by ≥10%. (Table 27)

TABLE 27

Stability Studies of C-SLNs oral formulation (n = 3)

| Temperature | Months | TDC (%) change | % Entrapment change | Particle size (nm) | PDI |
|---|---|---|---|---|---|
| 4° C. | 0 | 100 | 100 | 316.9 ± 2.60 | 0.206 |
| | 1 | 98.22 | 99.74 | 310.3 ± 1.02 | 0.213 |
| | 3 | 98.20 | 99.52 | 310.4 ± 3.50 | 0.242 |
| | 6 | 96.25 | 95.25 | 342 ± 20.00 | 0.242 |
| | 12 | 94.44 | 92.64 | 310.0 ± 7.0 | 0.278 |
| 25° C. | 0 | 100 | 100 | 316.9 ± 2.60 | 0.206 |
| | 1 | 99.11 | 99.67 | 333.2 ± 4.10 | 0.252 |
| 30° C. | 0 | 100 | 100 | 316.9 ± 2.60 | 0.206 |
| | 1 | 96.22 | 99.35 | 355.6 ± 2.69 | 0.254 |
| 40° C. | 0 | 100 | 100 | 316.9 ± 2.60 | 0.206 |
| | 1 | 95.73 | 99.29 | 358.6 ± 6.21 | 0.239 |

10. Pharmacokinetic Studies

A. Study Design

For in vivo pharmacokinetic studies, female Wistar Rats were used. The animals were divided into 3 groups (n=3). Groups 1 and 2 were administered 100 mg/kg BW of C-SLNs and CurcuwinR respectively whereas group 3 was administered 100 mg/kg BW of free curcumin dispersed in 0.5% w/v carboxymethyl cellulose. The blood samples (0.5 ml) were withdrawn from retro-orbital plexus at different time intervals and collected into microcentrifuge tubes containing EDTA. Plasma was separated by centrifuging the blood samples at 10000 rpm for 6 min at 5° C. After centrifugation, the plasma obtained was stored at −20° C. until analysis. All animal protocols were approved by the institutional animal ethics committee vide letter number 107/IAEC/18 and approval number PU/45/99/CPCSEA/IAEC/2017/89.

B. Sample Preparation (Extraction Procedure)

To 50 µl of plasma samples in an eppendorf tube, 150 µl of methanol and 300 µl of acetonitrile:water (1:1) was added. The sample was vortexed for 5 min and centrifuged at 15,000 rpm to separate precipitated proteins. Supernatant was transferred to suitably labelled tubes. The sample was filtered through 0.2 µm syringe filter and was used for analysis using the developed Ultra high pressure liquid chromatography (UPLC) method.

C. Data Analysis

The pharmacokinetic parameters were calculated using non-compartmental model. The area under the concentration-time curve from time zero to time t (AUCo-t) was calculated using the trapezoidal method. Peak concentration (Cmax) and the time at which the peak concentration is achieved (Tmax), were obtained directly from the individual concentration-time profiles. All values were corrected for the spiked concentration. The area under the concentration-time curve from time zero to infinity was calculated by: AUCo-x=AUCo-+Ct/Ke, where Ct is the drug concentration observed at the last time and Ke is the apparent elimination rate constant obtained from the terminal slope of the individual concentration-time curves after logarithmic transformation of the concentration values and application of linear regression. AUMC was determined by plotting concentration*time (ct) versus time (t) using trapezoidal method. Mean residence time (MRT) was calculated by: MRT=AUMC/AUC.

Observation

Plasma concentration after oral administration of 100 mg/kg doses of C-SLNs and CurcuwinR were compared with 100 mg/kg dose of free curcumin, and plotted against time (FIG. 30). Area under the curve was calculated using trapezoidal method.

The relevant parameters including Cmax, Tmax, AUCo-x and clearance are listed in the table 28 below.

TABLE 28

Various pharmacokinetic parameters obtained after single oral dose of free curcumin, Curcuwin ® and C-SLNs administered to rats (n = 3)

| Formulation | Dose (mg/kg) | $AUC_{0-\infty}$(h*ng/ml) | Cmax (ng/ml) | Tmax (h) | $AUMC_{0-\infty}$($h^2$*ng/ml) | MRT (h) | Clearance (l/h/kg) | Relative bioavailabilty w.r.t. Free curcumin |
|---|---|---|---|---|---|---|---|---|
| Free curcumin | 100 | 2.69 | 1.79 | 2 | 5.38 | 2 | 37167.34 | 1 |
| C-SLN | 100 | 110.59 | 49.27 | 1 | 287.68 | 2.6 | 904.25 | 41.11 |
| Curcuwin | 100 | 10.29 | 3.42 | 1 | 12.22 | 1.87 | 9718.13 | 3.83 |

The studies revealed that relative bioavailability with respect to free curcumin was increased by 41 times in case of C-SLNs whereas it was increased by only 3.83 times in CurcuwinR. This makes C-SLNs 10 times more bioavailable than the marketed formulation Curcuwin®.Clearance was found to decrease by 41 times and 3.8 times in case of C-SLNs and Curcuwin®, respectively as compared to free curcumin. In a pharmacokinetic study performed on human volunteers, Curcuwin® showed 136 times higher bioavailability than free curcumin (Jäger et al., 2014). From this, it can be inferred that C-SLNs will also show 5 a bioavailability higher than 136 times, when determined in humans.

(The bioanalytical methods were validated in terms of accuracy, linearity and precision. All the values conform to the ICH guidelines limits.)

11. Comparison with Existing Prior Arts

The solid lipid nanoparticles of curcumin of the present invention were compared with the solid lipid nanoparticles of the prior art and the attributes are tabulated in Table 29 below.

TABLE 29

| Comparison of the present invention with the prior arts | | | | | |
|---|---|---|---|---|---|
| Reference | Method of preparation | Organic solvent | Composition | | Technical advantage of the present formulation |
| (Nayak et al., 2010) | Nanoemulsion technique employing high-speed homogenizer and ultrasonic probe | Not used | Aqueous phase Polaxamer, Tween 80 Lipid Phase Soya lecithin PC, Trimyristin or Tristearin or Glyceryl monostearate | DL: 0.2% w/w DC: 0.3% w/w PS: 109-203 nm PDI: 0.167-0.210 | Drug loading as well as drug content is higher |
| (Shelat et al., 2015) | High pressure homogenization followed by ultracentrifugation | Not used | Aqueous Phase Propylene glycol Lipid Phase Compritol 888 ATO or Precirol ATO 5, Lipoid S 75 | DL: 5% w/w DC: 1% w/w PS: 200-300 nm | Drug loading is higher |
| (Beloqui et al., 2016) | High pressure homogenization method | Not used | Aqueous Phase Tween 80 and Kolliphor ® P188 Lipid Phase Precirol ATO ® 5, Miglyol 812N/F | DL: 3% w/w DC: 0.3% w/w PS: 280 nm PDI: 0.4 | Drug loading as well as drug content is higher |
| (Hazzah et al., 2016) | High speed homogenisation | Not added | Aqueous phase Polaxamer 407 Lipid phase Gelucire 50/13 | DL: 12% w/w DC: 0.6% w/w | Drug loading is higher |
| (Wang et al., 2015) | Emulsification and low temperature solidification method | Chloroform | Lipid Phase Stearic acid, lecithin Aqueous phase Myrj52 | DL: 36% w/w PS: 40-80 nm | Chloroform has been used in formulation of reported literature where as no organic solvent has been used in present formulation |
| (Gaur et al., 2016) | Modified emulsion/ solvent evaporation | Ethanol | Aqueous Phase Tween 80 Lipid Phase Glyceryl monostearate/ stearic acid/ ceramide | DL: 14% w/w PS: 102-156 nm PDI: 0.187-0.428 DC | Organic solvent is used in the cited research article Drug loading is higher in present |
| (Sutaria et al., 2012) | Hot melt oil-in-water (o/w) emulsion technique | Dicholoromethane | Lipid Phase Stearic acid Aqueous phase Ploxamer | PS: 250 nm EE: 69% | Organic solvent is used in the cited research article. Entrapment efficiency is high where as entrapment efficiency of the cited literature is very less |
| (Aditya et al., 2013) | Nanoemulsion technique employing high-speed homogenizer and ultrasonic probe | Not used | Aqueous phase Tween 80 Lipid phase Glyceryl monostearate, Oleic acid, lecithin | DL: 1.5% w/w DC: 0.006 w/v PS: 108 nm PDI: 0.28 EE: 78% | Drug loading as well as drug content is higher |
| (Puglia et al., 2012) | High speed homogenization followed by ultrasonicationand | Not used | Aqueous Phase Lutrol F68, Tween 80 Lipid Phase | DL = 5.88% w/w PS = 162.4 ± 10.5 nm EE = 87% | Drug loading is higher |

TABLE 29-continued

Comparison of the present invention with the prior arts

| Reference | Method of preparation | Organic solvent | Composition | | Technical advantage of the present formulation |
|---|---|---|---|---|---|
| | low temperature solidification method | | PrecirolATO 5 Miglyol 812 | | |
| (Sandhir et al., 2014) | High speed homogenization followed by low temperature solidification method | Not used | Aqueous Phase Taurocholate Lipid Phase Stearic acid Lecithin | DL: 1.1% w/w PS: 148 nm | Drug loading is higher |
| (Madane and Mahajan, 2016) | Hot high pressure homogenization | Not used | Aqueous phase Tween 80 and soya lecithin Lipid phase Precirol ATO ®5 and capmul MCM | PS: 146 PDI: 0.189 EE: 90.86% | Higher concentration of lipid is used in cited literature |
| (Sun et al., 2013) | Hot high pressure homogenization | Ethanol | Aqueous phase Pluronic F-68 Lipid phase Dynasan 114 ® and Sefsol-218 | DL: 0.74% w/w DC: 8 mg/100ml PS: 145 nm PDI: 0.213 EE: 92.34% | Drug loading as well as drug content is higher |
| (Ji et al., 2016) | Emulsification and low temperature solidification method | Ethylacetate and ethanol | Aqueous phase Brij78 and TPGS Lipid phase Glyceryl monostearate and soya lecithin | DL: 15% w/w DC: 0.1% w/v PS: 135.3 nm | Drug loading as well as drug content is higher. Organic solvents not used in our formulation |
| (Pedro et al., 2016) | Particles Generated from Gas Saturated Solution technique | Dimethylsulphoxide | Lipid phase Tris tearin and soya PC | | Supercritical fluid technology used in cited study results in high cost of production |
| (Esposito et al., 2014) | Emulsification followed by high speed homogenization | Not used | Aqueous phase Poloxamer Lipid phase Monolein Sodium cholate | DL: 0.33% w/w DC: 0.015% w/w | Drug loading as well as drug content is higher |
| (Wang et al., 2012) | Solvent injection method | Chloroform | Aqueous phase Myrj 52 Lipid phase Stearic acid and lecithin | DL: 28% PS: 190.4 nm PDI: 0.286 EE: 75% | Chloroform is used in the cited research article |
| (Righeschi et al., 2016) | Hot high shear homogenization process followed by ultrasonication | | | DL: 1-2% w/w DC = 0.054-1% w/w PS: PDI: EE: | Drug loading as well as drug content is higher |
| Ramalingam and Ko 2015 | | | | DL = 4.5% w/w DC = 1% w/v | Drug loading is higher |
| Tiyaboonchai et al., 2007 | | | | DL = 2% w/w DC = 0.1% w/v | Drug loading as well as drug content is higher Particle size of the cited study: 450 nmwhere as particle size of present formulation is less than 250 nm. |

TABLE 29-continued

Comparison of the present invention with the prior arts

| Reference | Method of preparation | Organic solvent | Composition | | Technical advantage of the present formulation |
|---|---|---|---|---|---|
| Chirio et al., | | | | DL = 5% w/w<br>DC = 0.05% w/v | Drug loading as well as drug content is higher |
| Noack et al., 2012 | | | | DL = 1% w/w<br>DC = 0.1% w/w | Drug loading as well as drug content is higher |
| Li et al., 2011 | | | | DL = 9.37% w/w | Drug loading is higher<br>PDI of the cited study is =0.41 where as PDI of present formulation is less than 0.3<br>Further no organic solvents has been used in present formulation |
| Chen et al., 2015 | | | | DC = 0.26% w/v | Drug content is higher |
| Kim et al., 2014 | | | | DL = 1% w/w | Drug loading is higher |
| Rahman et al., 2014 | | | | | PDI of cited literature is 0.451 which is higher than present formulation |
| Guri et al., 2013 | | | | DC = 0.05 mg/ml | Drug content is higher |
| Ambarsari at al., 2012 | | | | DL = 10% w/w<br>DC = 0.1% w/w | Drug loading as well as drug content is higher |
| Wang et al., 2013 | | | | | Solvent evaporation method used on the cited study which is difficult to scale up. Further, the method used in the cited literature is lengthy |
| Manduware et al., 2015 | | | | DL = 5% w/w | Drug loading higher |
| Kakkar et al., 2011a, Kakkar et al., 2011b, Kakkar et al., 2013 | | | | DC = 0.4% w/w<br>DL = 10% | Drug loading as well as drug content is higher<br>Surfactant concentration used in the cited literature is high |

The invention claimed is:

1. Solid lipid nanoparticles of curcumin, comprising a. a lipid phase comprising of curcumin, lipid or mixture of lipids selected from group consisting of glycerides and fatty acids, and a co-solvent,
   wherein curcumin is entrapped in the lipid phase in a soluble/amorphous form;

b. an aqueous phase comprising water, curcumin, surfactant, and co-surfactant,
   wherein curcumin in the aqueous phase is in a solubilized form to prevent crystallization, wherein the co-solvent is selected from polyethylene glycol, PVP, PVA, glycerol,-diethylene glycol monoethyl ether, glycerol monocaprylocaprate, polyethylene glycol monostearate, hydrogenated vegetable glycerides, glyceryl citrate, glyceryl lactate, glyceryl lincolate, glyceryl oleate, polyglyceryl-4-cocoate, polyglyceryl-3-carprate and derivatives thereof, polyglyceryl-3-capoylate and derivatives thereof.

2. The solid lipid nanoparticles of curcumin as claimed in claim 1, wherein the solid lipid nanoparticles of curcumin have a particle size in the range of 20-800 nm.

3. The solid lipid nanoparticles of curcumin as claimed in claim 1, wherein the solid lipid nanoparticles of curcumin have a spherical, ellipsoid, oblong, anisotropic, or rod shape.

4. The solid lipid nanoparticles of curcumin as claimed in claim 1, wherein the solid lipid nanoparticles of curcumin increase the relative bioavailability of curcumin by 5 to 250 times with respect to free curcumin.

5. The solid lipid nanoparticles of curcumin as claimed in claim 1, wherein the solid lipid nanoparticles show controlled release of curcumin up to 5 day or up to 9 days.

6. The solid lipid nanoparticles of curcumin as claimed in claim 1, wherein the solid lipid nanoparticles offer photostability and protection to incorporated curcumin against pH degradation at pH 1.2, 6.8, 7.4, and 9 with increase in tin of curcumin by 2 to 20 times as compared to free curcumin.

7. The solid lipid nanoparticles of curcumin as claimed in claim 1, wherein the solid lipid nanoparticles of curcumin show stability at 25° C. up to 6 months and 4° C. for more than one year.

8. The solid lipid nanoparticles of curcumin as claimed in claim 1, wherein the aqueous solid lipid nanoparticles of curcumin are spray dried or lyophilised in 2 to 25% w/v of at least one of mannitol, trehalose, sucrose, lactose, and lactulose.

9. The solid lipid nanoparticles of curcumin as claimed in claim 1, wherein the co-solvent is polyethylene glycol 600.

10. A process for preparing solid lipid nanoparticles of curcumin of claim 1, the process comprising the steps of:

a. dissolving curcumin in a co-solvent to obtain a solution and maintaining the solution at temperature 10° C. above lipid melting point temperature;

b. adding melted lipid or mixture of lipids selected from group consisting of glycerides and fatty acids to the solution obtained in step (a) to obtain a hot lipid phase;

c. preparing an aqueous surfactant phase comprising water, surfactant and co surfactant and maintaining the aqueous surfactant phase at a temperature 10° C. above lipid melting temperature;

d. adding the hot lipid phase of step (b) to the aqueous surfactant phase of step (c), or vice-versa, and mixing at high speed of 4000-15000 rpm for 5-10 min to obtain a primary coarse emulsion; and e. subjecting the primary coarse emulsion of step (d) to two to six cycles of homogenization at 500 to 1200 bars to obtain solid lipid nanoparticles of curcumin.

11. The process as claimed in claim 10, wherein the concentration of co-solvent in the solid lipid nanoparticle formulation is 5% to 8% w/w and the concentration of the surfactant in the solid lipid nanoparticle formulation is in the range of 8% to 12% w/w.

12. The process as claimed in claim 10, wherein the mixture of the hot lipid phase of step (b) and the aqueous surfactant phase of step (c) is homogenized at 8000 rpm for 8 min to obtain a primary coarse emulsion.

13. The process as claimed in claim 10, wherein step (e) comprises three cycles.

14. The process as claimed in claim 10, wherein the glyceride is selected from the group consisting of glyceryl behenate tricaprin, trilaurin, trimyristin, tripalmitin, tristearin, 1,2-dioctanoyl-sn-glycerol, 1,2-didecanoyl-sn-glycerol, 1,2-dilauroyl-sn-glycerol, 1,2-dimyristoyl-sn-glycerol, 1,2-dipalmitoyl-sn-glycerol, 1-palmitoyl-2-oleoyl-sn-glycerol, 1-stearoyl-2-linoleoyl-sn-glycerol, 1-stearoyl-2-arachidonoyl-sn-glycerol, 1-stearoyl-2-docosahexaenoyl-sn-glycerol, 1-oleoyl-2-acetyl-sn-glycerol, 1,2-di-O-phytanyl-sn-glycerol, 1,2-dipalmitoyl ethylene glycol, 1-2-dioleoyl ethylene glycol, glyceryl monostearate, behenoyl polyoxyl-8 glycerides, glyceryl palmitostearate, 1-O-hexadecyl-sn-glycerol, 1-O-hexadecyl-2-acetyl-sn-glycerol, 1-O-hexadecyl-2-O-methyl-sn-glycerol, 1,2-diacyl-3-O-(α-D-glucopyranosyl)-sn-glycerol, stearoylmacrogol-32 glycerides, stearoyl polyoxyl-32 glycerides, lauroyl macrogol-32 glycerides, lauroyl polyoxyl-32 glycerides, lauroyl macrogol-6 glycerides, lauroylpolyoxyl-6 glycerides, oleoyl macrogol-6 glycerides, oleoyl polyoxyl-6 glycerides, linoleoyl macrogol-6 glycerides, polyglyceryl-3 dioleate, glycerol monolinoleate, glyceryl monolinoleate, glycerol monooleates, diethylene glycol monoethyl ether, glyceryl dibehenate, glycerol distearate, glyceryl distearate, glyceryl dipalmitostearate, linoleoyl polyoxyl-6 glyceride, behenyl alcohol, cetyl alcohol, and potassium cetyl alcohol.

15. The process as claimed in claim 10, wherein the fatty acid is selected from the group consisting of saturated C4-C28 fatty acids and unsaturated C4-C28 fatty acids.

16. The process as claimed in claim 15, wherein the fatty acid is stearic acid.

17. The process as claimed in claim 10, wherein the surfactant is selected from the group consisting of ethylene oxide copolymers, propylene oxide copolymers, poloxamers, sorbitan ethylene oxide/propylene oxide copolymers, polysorbate 20, polysorbate 60, polysorbate 80, sorbitan esters, span 20, span 40, span 60, span 80, alkyllaryl polyether alcohol polymers, tyloxapol, bile salts, cholate, glycocholate, taurocholate, taurodeoxycholate, gemini surfactants, alcohols, diethylene glycol monoethyl ether, propanediol, capryl glucoside, decy glucoside, kolliwax, and mixtures thereof.

18. The process as claimed in claim 10, wherein the co-surfactant is selected from the group consisting of soy lecithin, egg lecithin, phosphatidylcholine, cholate, glycocholate, taurocholate, taurodeoxycholate, and mixtures thereof.

19. The process for preparing solid lipid nanoparticles of curcumin as claimed in claim 10, wherein curcumin content in the solid lipid nanoparticles is in the range of 0.5 to 10% w/v of the aqueous SLN dispersion and up to 50% w/w with respect to the lipid matrix.

20. The process for preparing solid lipid nanoparticles of curcumin as claimed in claim 10, wherein entrapment efficiency of curcumin in the solid lipid nanoparticles is in the range of 50-100% in terms of actual curcumin content of the formulation.

* * * * *